US011273056B2

(12) United States Patent
Chataigner et al.

(10) Patent No.: US 11,273,056 B2
(45) Date of Patent: Mar. 15, 2022

(54) ANCHORING DEVICE AND SYSTEM FOR AN INTERVERTEBRAL IMPLANT, INTERVERTEBRAL IMPLANT AND IMPLANTATION INSTRUMENT

(71) Applicant: LDR MEDICAL, Rosieres Pres Troyes (FR)

(72) Inventors: Herve Chataigner, Bussieres (FR); Craig Chebuhar, Marietta, GA (US); Herve Dinville, St. Parres Aux Tertres (FR); Emmanuel Bougere, Bordeaux (FR)

(73) Assignee: LDR Medical, Rosieres Pres Troyes (FR)

( * ) Notice: Subject to any disclaimer, the term of this patent is extended or adjusted under 35 U.S.C. 154(b) by 183 days.

(21) Appl. No.: 16/429,968

(22) Filed: Jun. 3, 2019

(65) Prior Publication Data
US 2019/0388237 A1 Dec. 26, 2019

Related U.S. Application Data

(63) Continuation of application No. 14/721,818, filed on May 26, 2015, now Pat. No. 10,350,083, which is a (Continued)

(30) Foreign Application Priority Data

Feb. 24, 2012 (FR) ...................................... 1251733

(51) Int. Cl.
A61F 2/46 (2006.01)
A61F 2/44 (2006.01)
(Continued)

(52) U.S. Cl.
CPC ............ A61F 2/4611 (2013.01); A61F 2/442 (2013.01); A61F 2/447 (2013.01); A61F 2/4455 (2013.01);
(Continued)

(58) Field of Classification Search
CPC .................. A61F 2/4611; A61F 2/4455–2/447
See application file for complete search history.

(56) References Cited

U.S. PATENT DOCUMENTS 3,374,786 A 3/1968 Callender, Jr.
3,791,380 A 2/1974 Dawidowski
(Continued)

FOREIGN PATENT DOCUMENTS

AU 2013224006 A1 7/2014
AU 2013224006 B2 2/2017
(Continued)

OTHER PUBLICATIONS

"U.S. Appl. No. 10/276,712, Advisory Action dated Feb. 8, 2006", 3 pgs.
(Continued)

Primary Examiner — Julianna N Harvey
(74) Attorney, Agent, or Firm — Schwegman Lundberg & Woessner, P.A.

(57) ABSTRACT

Various embodiments of intervertebral implants, anchoring devices for intervertebral implants, and implantation instrumentation are provided, along with various embodiments of methods for using one or more of the devices. Some embodiments of an anchoring device have a body comprising at least one curve and a rigid plate elongated along a longitudinal axis so that its front end enters at least one vertebra while its rear end remains in the passage of an implant. In some embodiments, the plate comprises at least one longitudinal slot separating at least one posterior portion (Continued)

of the plate into two branches, with at least one branch comprising at least one withdrawal stop configured to retain the device in the implant.

9 Claims, 9 Drawing Sheets

Related U.S. Application Data continuation of application No. 13/774,547, filed on Feb. 22, 2013, now Pat. No. 9,039,774.

(51) Int. Cl.
*A61F 2/30* (2006.01)
*A61B 17/80* (2006.01)

(52) U.S. Cl.
CPC ....... *A61B 17/809* (2013.01); *A61F 2002/305* (2013.01); *A61F 2002/30306* (2013.01); *A61F 2002/30331* (2013.01); *A61F 2002/30401* (2013.01); *A61F 2002/30403* (2013.01); *A61F 2002/30428* (2013.01); *A61F 2002/30433* (2013.01); *A61F 2002/30515* (2013.01); *A61F 2002/30576* (2013.01); *A61F 2002/30578* (2013.01); *A61F 2002/30579* (2013.01); *A61F 2002/30593* (2013.01); *A61F 2002/30594* (2013.01); *A61F 2002/30604* (2013.01); *A61F 2002/30777* (2013.01); *A61F 2002/30782* (2013.01); *A61F 2002/30785* (2013.01); *A61F 2002/30787* (2013.01); *A61F 2002/30841* (2013.01); *A61F 2002/30879* (2013.01); *A61F 2002/30889* (2013.01); *A61F 2002/30904* (2013.01); *A61F 2002/4627* (2013.01); *A61F 2220/0016* (2013.01)

(56) References Cited

U.S. PATENT DOCUMENTS

| | | |
|---|---|---|
| 3,892,232 A | 7/1975 | Neufeld |
| 4,009,712 A | 3/1977 | Burstein et al. |
| 4,135,506 A | 1/1979 | Ulrich |
| 4,175,555 A | 11/1979 | Herbert |
| 4,237,875 A | 12/1980 | Termanini |
| 4,379,451 A | 4/1983 | Getscher |
| 4,409,974 A | 10/1983 | Freedland et al. |
| 4,432,358 A | 2/1984 | Fixel |
| 4,488,543 A | 12/1984 | Tornier |
| 4,494,535 A | 1/1985 | Haig |
| 4,519,100 A | 5/1985 | Wills et al. |
| 4,561,432 A | 12/1985 | Mazor |
| 4,599,086 A | 7/1986 | Doty |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,657,001 A | 4/1987 | Fixel |
| 4,714,469 A | 12/1987 | Kenna |
| 4,721,103 A | 1/1988 | Freedland |
| 4,759,352 A | 7/1988 | Lozier |
| 4,787,378 A | 11/1988 | Sodhi |
| 4,790,303 A | 12/1988 | Steffee |
| 4,791,918 A | 12/1988 | Von Hasselbach |
| 4,892,545 A | 1/1990 | Day et al. |
| 4,898,156 A | 2/1990 | Gatturna et al. |
| 4,904,261 A | 2/1990 | Dove et al. |
| 4,946,468 A | 8/1990 | Li |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,046,513 A | 9/1991 | Gatturna et al. |
| 5,057,103 A | 10/1991 | Davis |
| 5,062,851 A | 11/1991 | Branemark |
| 5,087,266 A | 2/1992 | Connell et al. |
| 5,098,433 A | 3/1992 | Freedland |
| 5,116,336 A | 5/1992 | Frigg |
| 5,129,901 A | 7/1992 | Decoste |
| 5,176,681 A | 1/1993 | Lawes et al. |
| 5,192,303 A | 3/1993 | Gatturna et al. |
| 5,192,327 A | 3/1993 | Brantigan |
| 5,207,679 A | 5/1993 | Li |
| 5,217,486 A | 6/1993 | Rice et al. |
| 5,242,448 A | 9/1993 | Pettine et al. |
| 5,246,458 A | 9/1993 | Graham |
| 5,300,074 A | 4/1994 | Frigg |
| 5,306,307 A | 4/1994 | Senter et al. |
| 5,306,309 A | 4/1994 | Wagner et al. |
| 5,324,292 A | 6/1994 | Meyers |
| 5,342,394 A | 8/1994 | Matsuno et al. |
| 5,356,410 A | 10/1994 | Pennig |
| 5,356,413 A | 10/1994 | Martins et al. |
| 5,372,599 A | 12/1994 | Martins |
| 5,397,364 A | 3/1995 | Kozak et al. |
| 5,417,692 A | 5/1995 | Goble et al. |
| 5,417,712 A | 5/1995 | Whittaker et al. |
| 5,425,772 A | 6/1995 | Brantigan |
| 5,429,641 A | 7/1995 | Gotfried |
| 5,437,674 A | 8/1995 | Worcel |
| 5,443,514 A | 8/1995 | Steffee |
| 5,456,721 A | 10/1995 | Legrand |
| 5,458,601 A | 10/1995 | Young, Jr. et al. |
| 5,458,638 A | 10/1995 | Kuslich et al. |
| 5,472,452 A | 12/1995 | Trott |
| 5,478,342 A | 12/1995 | Kohrs |
| 5,489,210 A | 2/1996 | Hanosh |
| 5,507,754 A | 4/1996 | Green et al. |
| 5,522,845 A | 6/1996 | Wenstrom, Jr. |
| 5,522,899 A | 6/1996 | Michelson |
| 5,531,792 A | 7/1996 | Huene |
| 5,534,004 A | 7/1996 | Santangelo |
| 5,534,029 A | 7/1996 | Shima |
| 5,549,617 A | 8/1996 | Green et al. |
| 5,554,191 A | 9/1996 | Lahille et al. |
| 5,562,689 A | 10/1996 | Green et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,635 A | 3/1997 | Michelson |
| 5,609,636 A | 3/1997 | Kohrs et al. |
| 5,613,974 A | 3/1997 | Andreas et al. |
| 5,620,012 A | 4/1997 | Benderev et al. |
| 5,643,321 A | 7/1997 | Mcdevitt |
| 5,702,449 A | 12/1997 | Mckay |
| 5,713,899 A | 2/1998 | Marnay et al. |
| 5,741,253 A | 4/1998 | Michelson |
| 5,755,798 A | 5/1998 | Papavero et al. |
| 5,766,252 A | 6/1998 | Henry et al. |
| 5,766,253 A | 6/1998 | Brosnahan, III |
| 5,772,661 A | 6/1998 | Michelson |
| 5,776,199 A | 7/1998 | Michelson |
| 5,782,830 A | 7/1998 | Farris |
| 5,782,919 A | 7/1998 | Zdeblick et al. |
| 5,797,909 A | 8/1998 | Michelson |
| 5,800,547 A | 9/1998 | Schafer et al. |
| 5,800,550 A | 9/1998 | Sertich |
| 5,860,973 A | 1/1999 | Michelson |
| 5,865,845 A | 2/1999 | Thalgott |
| 5,888,222 A | 3/1999 | Coates et al. |
| 5,888,223 A | 3/1999 | Bray, Jr. |
| 5,888,224 A | 3/1999 | Beckers et al. |

(56) References Cited

U.S. PATENT DOCUMENTS

| | | |
|---|---|---|
| 5,888,227 A | 3/1999 | Cottle |
| 5,895,427 A | 4/1999 | Kuslich et al. |
| 5,968,098 A | 10/1999 | Winslow |
| 5,980,522 A | 11/1999 | Koros et al. |
| 5,984,967 A | 11/1999 | Zdeblick et al. |
| 5,989,289 A | 11/1999 | Coates et al. |
| 6,001,130 A | 12/1999 | Bryan et al. |
| 6,033,438 A | 3/2000 | Bianchi et al. |
| 6,045,579 A | 4/2000 | Hochshuler et al. |
| 6,059,787 A | 5/2000 | Allen |
| 6,063,121 A | 5/2000 | Xavier et al. |
| 6,066,174 A | 5/2000 | Farris |
| 6,066,175 A | 5/2000 | Henderson et al. |
| 6,080,158 A | 6/2000 | Lin |
| 6,080,193 A | 6/2000 | Hochshuler et al. |
| 6,093,205 A | 7/2000 | Mcleod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,111,164 A | 8/2000 | Rainey et al. |
| 6,113,637 A | 9/2000 | Gill et al. |
| 6,113,638 A | 9/2000 | Williams et al. |
| 6,120,502 A | 9/2000 | Michelson |
| 6,123,705 A | 9/2000 | Michelson |
| 6,129,763 A | 10/2000 | Chauvin et al. |
| 6,136,031 A | 10/2000 | Middleton |
| 6,143,032 A | 11/2000 | Schafer et al. |
| 6,146,421 A | 11/2000 | Gordon et al. |
| 6,149,650 A | 11/2000 | Michelson |
| 6,156,067 A | 12/2000 | Bryan et al. |
| 6,174,311 B1 | 1/2001 | Branch et al. |
| 6,179,873 B1 | 1/2001 | Zientek |
| 6,179,875 B1 | 1/2001 | Von Strempel |
| 6,193,757 B1 | 2/2001 | Foley et al. |
| 6,206,922 B1 | 3/2001 | Zdeblick et al. |
| 6,206,923 B1 | 3/2001 | Boyd et al. |
| 6,210,412 B1 | 4/2001 | Michelson |
| 6,214,050 B1 | 4/2001 | Huene |
| 6,224,595 B1 | 5/2001 | Michelson |
| 6,235,059 B1 | 5/2001 | Benezech et al. |
| 6,241,733 B1 | 6/2001 | Nicholson et al. |
| 6,241,769 B1 | 6/2001 | Nicholson et al. |
| 6,241,770 B1 | 6/2001 | Michelson |
| 6,245,072 B1 | 6/2001 | Zdeblick et al. |
| 6,245,108 B1 | 6/2001 | Biscup |
| 6,251,140 B1 | 6/2001 | Marino et al. |
| 6,258,094 B1 | 7/2001 | Nicholson et al. |
| 6,258,125 B1 | 7/2001 | Paul et al. |
| 6,261,293 B1 | 7/2001 | Nicholson et al. |
| 6,261,295 B1 | 7/2001 | Nicholson et al. |
| 6,264,656 B1 | 7/2001 | Michelson |
| 6,267,764 B1 | 7/2001 | Elberg |
| 6,270,498 B1 | 8/2001 | Michelson et al. |
| 6,277,149 B1 | 8/2001 | Boyle et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,342,074 B1 | 1/2002 | Simpson |
| 6,348,071 B1 | 2/2002 | Steffee et al. |
| 6,350,283 B1 | 2/2002 | Michelson |
| 6,364,880 B1 | 4/2002 | Michelson |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,395,031 B1 | 5/2002 | Foley et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,703 B1 | 7/2002 | Fallin et al. |
| 6,419,704 B1 | 7/2002 | Ferree |
| 6,423,063 B1 | 7/2002 | Bonutti |
| 6,423,095 B1 | 7/2002 | Van Hoeck et al. |
| 6,432,106 B1 | 8/2002 | Fraser |
| 6,432,107 B1 | 8/2002 | Ferree |
| 6,447,512 B1 | 9/2002 | Landry et al. |
| 6,447,544 B1 | 9/2002 | Michelson |
| 6,447,546 B1 | 9/2002 | Bramlet et al. |
| 6,447,547 B1 | 9/2002 | Michelson |
| 6,454,769 B2 | 9/2002 | Wagner et al. |
| 6,458,159 B1 | 10/2002 | Thalgott |
| 6,461,359 B1 | 10/2002 | Tribus |
| 6,468,310 B1 | 10/2002 | Ralph et al. |
| 6,471,724 B2 | 10/2002 | Zdeblick et al. |
| 6,478,823 B1 | 11/2002 | Michelson |
| 6,482,233 B1 | 11/2002 | Aebi et al. |
| 6,482,584 B1 | 11/2002 | Mills et al. |
| 6,485,517 B1 | 11/2002 | Michelson |
| 6,497,726 B1 | 12/2002 | Carter et al. |
| 6,500,205 B1 | 12/2002 | Michelson |
| 6,524,312 B2 | 2/2003 | Landry et al. |
| 6,527,806 B2 | 3/2003 | Ralph et al. |
| 6,540,753 B2 | 4/2003 | Cohen |
| 6,540,785 B1 | 4/2003 | Gill et al. |
| 6,554,863 B2 | 4/2003 | Paul et al. |
| 6,558,423 B1 | 5/2003 | Michelson |
| 6,565,605 B2 | 5/2003 | Goble et al. |
| 6,576,016 B1 | 6/2003 | Hochshuler et al. |
| 6,579,291 B1 | 6/2003 | Keith et al. |
| 6,582,468 B1 | 6/2003 | Gauchet |
| 6,592,624 B1 | 7/2003 | Fraser et al. |
| 6,599,320 B1 | 7/2003 | Kuslich |
| 6,605,089 B1 | 8/2003 | Michelson |
| 6,607,530 B1 | 8/2003 | Carl et al. |
| 6,610,065 B1 | 8/2003 | Branch et al. |
| 6,610,089 B1 | 8/2003 | Liu et al. |
| 6,610,092 B2 | 8/2003 | Ralph et al. |
| 6,613,091 B1 | 9/2003 | Zdeblick et al. |
| 6,613,278 B1 | 9/2003 | Mills et al. |
| 6,616,671 B2 | 9/2003 | Landry et al. |
| 6,635,086 B2 | 10/2003 | Lin |
| 6,635,087 B2 | 10/2003 | Angelucci et al. |
| 6,645,206 B1 | 11/2003 | Zdeblick et al. |
| 6,645,249 B2 | 11/2003 | Ralph et al. |
| 6,648,893 B2 | 11/2003 | Dudasik |
| 6,652,584 B2 | 11/2003 | Michelson |
| 6,652,818 B1 | 11/2003 | Mills et al. |
| 6,660,038 B2 | 12/2003 | Boyer, II et al. |
| 6,666,890 B2 | 12/2003 | Michelson |
| 6,669,730 B2 | 12/2003 | Ralph et al. |
| 6,669,731 B2 | 12/2003 | Ralph et al. |
| 6,673,113 B2 | 1/2004 | Ralph et al. |
| 6,676,703 B2 | 1/2004 | Biscup |
| 6,679,887 B2 | 1/2004 | Nicholson et al. |
| 6,679,915 B1 | 1/2004 | Cauthen |
| 6,695,851 B2 | 2/2004 | Zdeblick et al. |
| 6,695,882 B2 | 2/2004 | Bianchi et al. |
| 6,706,067 B2 | 3/2004 | Shimp et al. |
| 6,709,458 B2 | 3/2004 | Michelson |
| 6,716,247 B2 | 4/2004 | Michelson |
| 6,719,794 B2 | 4/2004 | Gerber et al. |
| 6,723,128 B2 | 4/2004 | Uk |
| 6,733,504 B2 | 5/2004 | Lin et al. |
| 6,733,531 B1 | 5/2004 | Trieu |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,743,255 B2 | 6/2004 | Ferree |
| 6,743,256 B2 | 6/2004 | Mason |
| 6,743,257 B2 | 6/2004 | Castro |
| 6,749,636 B2 | 6/2004 | Michelson |
| 6,758,849 B1 | 7/2004 | Michelson |
| 6,767,367 B1 | 7/2004 | Michelson |
| 6,770,074 B2 | 8/2004 | Michelson |
| 6,770,096 B2 | 8/2004 | Bolger et al. |
| 6,793,679 B2 | 9/2004 | Michelson |
| RE38,614 E | 10/2004 | Paul et al. |
| 6,800,092 B1 | 10/2004 | Williams et al. |
| 6,800,093 B2 | 10/2004 | Nicholson et al. |
| 6,805,713 B1 | 10/2004 | Carter et al. |
| 6,805,714 B2 | 10/2004 | Sutcliffe |

(56) References Cited

U.S. PATENT DOCUMENTS

| | | |
|---|---|---|
| 6,808,537 B2 | 10/2004 | Michelson |
| 6,835,206 B2 | 12/2004 | Jackson |
| 6,849,093 B2 | 2/2005 | Michelson |
| 6,890,355 B2 | 5/2005 | Michelson |
| 6,902,580 B2 | 6/2005 | Fallin et al. |
| 6,923,811 B1 | 8/2005 | Carl et al. |
| 6,923,830 B2 | 8/2005 | Michelson |
| 6,955,691 B2 | 10/2005 | Chae et al. |
| 6,962,606 B2 | 11/2005 | Michelson |
| 6,964,687 B1 | 11/2005 | Bernard et al. |
| 6,972,019 B2 | 12/2005 | Michelson |
| 6,972,035 B2 | 12/2005 | Michelson |
| 6,981,975 B2 | 1/2006 | Michelson |
| 6,984,234 B2 | 1/2006 | Bray |
| 6,994,727 B2 | 2/2006 | Khandkar et al. |
| 7,001,385 B2 | 2/2006 | Bonutti |
| 7,008,453 B1 | 3/2006 | Michelson |
| 7,018,412 B2 | 3/2006 | Ferreira et al. |
| 7,033,394 B2 | 4/2006 | Michelson |
| 7,041,135 B2 | 5/2006 | Michelson |
| 7,041,136 B2 | 5/2006 | Goble et al. |
| 7,048,762 B1 | 5/2006 | Sander et al. |
| 7,048,765 B1 | 5/2006 | Grooms et al. |
| 7,060,097 B2 | 6/2006 | Fraser et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,112,206 B2 | 9/2006 | Michelson |
| 7,118,579 B2 | 10/2006 | Michelson |
| 7,118,598 B2 | 10/2006 | Michelson |
| 7,128,760 B2 | 10/2006 | Michelson |
| 7,128,761 B2 | 10/2006 | Kuras et al. |
| 7,153,325 B2 | 12/2006 | Kim et al. |
| 7,163,561 B2 | 1/2007 | Michelson |
| 7,211,112 B2 | 5/2007 | Baynham et al. |
| 7,217,291 B2 | 5/2007 | Zucherman et al. |
| 7,217,293 B2 | 5/2007 | Branch |
| 7,223,289 B2 | 5/2007 | Trieu et al. |
| 7,232,463 B2 | 6/2007 | Falahee |
| 7,232,464 B2 | 6/2007 | Mathieu |
| 7,235,082 B2 | 6/2007 | Bartish et al. |
| 7,276,081 B1 | 10/2007 | Coates et al. |
| 7,291,170 B2 | 11/2007 | Huppert |
| 7,326,248 B2 | 2/2008 | Michelson |
| 7,361,196 B2 | 4/2008 | Fallin et al. |
| 7,410,501 B2 | 8/2008 | Michelson |
| 7,431,735 B2 | 10/2008 | Liu et al. |
| 7,435,262 B2 | 10/2008 | Michelson |
| 7,442,209 B2 | 10/2008 | Michelson |
| 7,445,636 B2 | 10/2008 | Liu et al. |
| 7,445,635 B2 | 11/2008 | Fallin et al. |
| 7,455,692 B2 | 11/2008 | Michelson |
| 7,465,317 B2 | 12/2008 | Malberg et al. |
| 7,479,160 B2 | 1/2009 | Branch et al. |
| 7,503,933 B2 | 3/2009 | Michelson |
| 7,540,882 B2 | 6/2009 | Michelson |
| 7,566,345 B1 | 7/2009 | Fallin et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,604,654 B2 | 10/2009 | Fallin et al. |
| 7,608,107 B2 | 10/2009 | Michelson |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,958 B2 | 11/2009 | Zdeblick et al. |
| 7,625,393 B2 | 12/2009 | Fallin et al. |
| 7,637,951 B2 | 12/2009 | Michelson |
| 7,637,953 B2 | 12/2009 | Branch et al. |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 | 4/2010 | Zeegers |
| 7,695,517 B2 | 4/2010 | Benzel et al. |
| 7,727,280 B2 | 6/2010 | McLuen |
| 7,744,602 B2 | 6/2010 | Teeny et al. |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,097,034 B2 | 1/2012 | Michelson |
| 8,114,082 B2 | 2/2012 | Boyajian et al. |
| 8,118,873 B2 | 2/2012 | Humphreys et al. |
| 8,137,405 B2 | 3/2012 | Kostuik et al. |
| 8,147,556 B2 | 4/2012 | Louis et al. |
| 8,167,946 B2 | 5/2012 | Michelson |
| 8,167,949 B2 | 5/2012 | Tyber et al. |
| 8,167,950 B2 | 5/2012 | Aferzon et al. |
| 8,182,539 B2 | 5/2012 | Tyber et al. |
| 8,187,329 B2 | 5/2012 | Theofilos |
| 8,187,332 B2 | 5/2012 | Mcluen |
| 8,216,312 B2 | 7/2012 | Gray |
| 8,241,359 B2 | 8/2012 | Davis et al. |

(56) References Cited

U.S. PATENT DOCUMENTS

| | | |
|---|---|---|
| 8,267,999 B2 | 9/2012 | Beaurain et al. |
| 8,313,528 B1 | 11/2012 | Wensel |
| 8,343,219 B2 | 1/2013 | Allain et al. |
| 8,349,015 B2 | 1/2013 | Bae et al. |
| 8,696,681 B2 | 4/2014 | Harris et al. |
| 9,039,774 B2 | 5/2015 | Chataigner et al. |
| 9,044,337 B2 | 6/2015 | Dinville et al. |
| 10,245,156 B2 | 4/2019 | Chataigner et al. |
| 10,350,083 B2 | 7/2019 | Chataigner et al. |
| 2001/0018614 A1 | 8/2001 | Bianchi |
| 2001/0020185 A1 | 9/2001 | Ray |
| 2001/0031254 A1 | 10/2001 | Bianchi et al. |
| 2001/0031967 A1 | 10/2001 | Nicholson et al. |
| 2002/0016592 A1 | 2/2002 | Branch et al. |
| 2002/0026243 A1 | 2/2002 | Lin |
| 2002/0032483 A1 | 3/2002 | Nicholson et al. |
| 2002/0040243 A1 | 4/2002 | Attali et al. |
| 2002/0070565 A1 | 6/2002 | Szapucki et al. |
| 2002/0072806 A1 | 6/2002 | Buskirk et al. |
| 2002/0082597 A1 | 6/2002 | Fraser |
| 2002/0082700 A1 | 6/2002 | Bianchi et al. |
| 2002/0106393 A1 | 8/2002 | Bianchi et al. |
| 2002/0107572 A1 | 8/2002 | Foley et al. |
| 2002/0119437 A1 | 8/2002 | Grroms et al. |
| 2002/0138143 A1 | 9/2002 | Grooms et al. |
| 2002/0151893 A1 | 10/2002 | Santilli |
| 2002/0161444 A1 | 10/2002 | Choi |
| 2002/0165612 A1 | 11/2002 | Gerber et al. |
| 2002/0165613 A1 | 11/2002 | Lin et al. |
| 2002/0193880 A1 | 12/2002 | Fraser |
| 2003/0023304 A1 | 1/2003 | Carter et al. |
| 2003/0027125 A1 | 2/2003 | Mills et al. |
| 2003/0028249 A1 | 2/2003 | Baccelli et al. |
| 2003/0060886 A1 | 3/2003 | Van Hoeck et al. |
| 2003/0069640 A1 | 4/2003 | Ferreira et al. |
| 2003/0074075 A1 | 4/2003 | James, Jr. et al. |
| 2003/0097179 A1 | 5/2003 | Carter et al. |
| 2003/0100950 A1 | 5/2003 | Moret |
| 2003/0109928 A1 | 6/2003 | Pasquet et al. |
| 2003/0135279 A1 | 7/2003 | Michelson |
| 2003/0139815 A1 | 7/2003 | Grooms et al. |
| 2003/0149438 A1 | 8/2003 | Nichols et al. |
| 2003/0167091 A1 | 9/2003 | Scharf |
| 2003/0187436 A1 | 10/2003 | Bolger et al. |
| 2003/0195514 A1 | 10/2003 | Trieu et al. |
| 2003/0195626 A1 | 10/2003 | Huppert |
| 2003/0195629 A1 | 10/2003 | Pafford et al. |
| 2003/0195632 A1 | 10/2003 | Foley et al. |
| 2003/0204260 A1 | 10/2003 | Ferree |
| 2003/0233147 A1 | 12/2003 | Nicholson et al. |
| 2004/0010312 A1 | 1/2004 | Enayati |
| 2004/0030387 A1 | 2/2004 | Landry et al. |
| 2004/0073307 A1 | 4/2004 | Keller |
| 2004/0073309 A1 | 4/2004 | Bianchi et al. |
| 2004/0073313 A1 | 4/2004 | Link et al. |
| 2004/0093083 A1 | 5/2004 | Branch et al. |
| 2004/0097929 A1 | 5/2004 | Branch et al. |
| 2004/0115172 A1 | 6/2004 | Bianchi et al. |
| 2004/0117022 A1 | 6/2004 | Marnay et al. |
| 2004/0127990 A1 | 7/2004 | Charles, Jr. et al. |
| 2004/0127993 A1 | 7/2004 | Kast et al. |
| 2004/0127994 A1 | 7/2004 | Kast et al. |
| 2004/0148029 A1 | 7/2004 | Bianchi et al. |
| 2004/0162617 A1 | 8/2004 | Zucherman et al. |
| 2004/0172130 A1 | 9/2004 | Nakahara et al. |
| 2004/0199254 A1 | 10/2004 | Louis et al. |
| 2004/0210219 A1 | 10/2004 | Bray |
| 2004/0210308 A1 | 10/2004 | Carter et al. |
| 2004/0210313 A1 | 10/2004 | Michelson |
| 2004/0230306 A1 | 11/2004 | Hoeck et al. |
| 2004/0243238 A1 | 12/2004 | Arnin et al. |
| 2004/0243240 A1 | 12/2004 | Beaurain et al. |
| 2004/0254643 A1 | 12/2004 | Jackson |
| 2005/0004672 A1 | 1/2005 | Pafford et al. |
| 2005/0015149 A1 | 1/2005 | Michelson |
| 2005/0027359 A1 | 2/2005 | Mashburn |
| 2005/0027360 A1 | 2/2005 | Webb et al. |
| 2005/0038511 A1 | 2/2005 | Martz et al. |
| 2005/0038512 A1 | 2/2005 | Michelson |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0085917 A1 | 4/2005 | Marnay et al. |
| 2005/0096742 A1 | 5/2005 | Mills et al. |
| 2005/0096745 A1 | 5/2005 | Andre et al. |
| 2005/0100862 A1 | 5/2005 | Mills et al. |
| 2005/0101957 A1 | 5/2005 | Buskirk et al. |
| 2005/0119744 A1 | 6/2005 | Buskirk et al. |
| 2005/0119747 A1 | 6/2005 | Fabris Monterumici et al. |
| 2005/0143733 A1 | 6/2005 | Petit |
| 2005/0143825 A1 | 6/2005 | Enayati |
| 2005/0149189 A1 | 7/2005 | Mokhtar et al. |
| 2005/0165483 A1 | 7/2005 | Ray, III et al. |
| 2005/0171554 A1 | 8/2005 | Estes et al. |
| 2005/0288788 A1 | 12/2005 | Dougherty-Shah |
| 2006/0058878 A1 | 3/2006 | Michelson |
| 2006/0069437 A1 | 3/2006 | Weber |
| 2006/0085076 A1 | 4/2006 | Krishna et al. |
| 2006/0089717 A1 | 4/2006 | Krishna et al. |
| 2006/0095136 A1 | 5/2006 | Mcluen |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0155377 A1 | 7/2006 | Beaurain et al. |
| 2006/0206208 A1 | 9/2006 | Michelson |
| 2006/0235426 A1 | 10/2006 | Lim et al. |
| 2006/0241761 A1 | 10/2006 | Gately |
| 2006/0241764 A1 | 10/2006 | Michelson |
| 2006/0253201 A1 | 11/2006 | Mcluen |
| 2007/0016297 A1 | 1/2007 | Johnson |
| 2007/0032871 A1 | 2/2007 | Michelson |
| 2007/0073404 A1 | 3/2007 | Rashbaum et al. |
| 2007/0093850 A1 | 4/2007 | Harris et al. |
| 2007/0142843 A1 | 6/2007 | Dye |
| 2007/0162128 A1 | 7/2007 | DeRidder et al. |
| 2007/0179623 A1 | 8/2007 | Trieu et al. |
| 2007/0250167 A1 | 10/2007 | Bray et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2008/0021562 A1 | 1/2008 | Huppert |
| 2008/0027547 A1 | 1/2008 | Yu et al. |
| 2008/0027550 A1 | 1/2008 | Link et al. |
| 2008/0033562 A1 | 2/2008 | Krishna et al. |
| 2008/0051887 A1 | 2/2008 | Carter et al. |
| 2008/0109083 A1 | 5/2008 | Van Hoeck et al. |
| 2008/0125865 A1 | 5/2008 | Abdelgany |
| 2008/0161933 A1 | 7/2008 | Grotz et al. |
| 2008/0195211 A1 | 8/2008 | Lin et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0062921 A1* | 3/2009 | Michelson ............ A61F 2/4455 623/17.16 |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1* | 4/2009 | Allain ................ A61F 2/30749 623/17.16 |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |

(56) References Cited

U.S. PATENT DOCUMENTS

| | | |
|---|---|---|
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0002221 A1 | 9/2009 | Cipoletti et al. |
| 2009/0222092 A1 | 9/2009 | Davis et al. |
| 2009/0234455 A1 | 9/2009 | Moskowitz et al. |
| 2009/0265007 A1 | 10/2009 | Colleran |
| 2009/0270990 A1 | 10/2009 | Louis et al. |
| 2010/0004664 A1 | 1/2010 | Boyajian et al. |
| 2010/0049259 A1 | 2/2010 | Lambrecht et al. |
| 2010/0057206 A1 | 3/2010 | Duffield et al. |
| 2010/0057207 A1 | 3/2010 | Ray, III et al. |
| 2010/0063554 A1 | 3/2010 | Branch et al. |
| 2010/0070037 A1 | 3/2010 | Parry et al. |
| 2010/0082104 A1 | 4/2010 | Carter et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | Mcdonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0217396 A1 | 8/2010 | Bianchi et al. |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0268349 A1 | 10/2010 | Bianchi et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0000431 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1* | 4/2011 | Donner ............ A61F 2/4611 606/264 |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0160866 A1* | 6/2011 | Laurence ............ A61F 2/442 623/17.16 |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301707 A1 | 12/2011 | Buskirk et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0004660 A1 | 1/2012 | Grooms et al. |
| 2012/0078371 A1* | 3/2012 | Gamache ............ A61B 17/0682 623/17.16 |
| 2012/0078373 A1 | 3/2012 | Gamache et al. |
| 2012/0116466 A1 | 5/2012 | Dinville et al. |
| 2012/0191196 A1 | 7/2012 | Louis et al. |
| 2012/0283837 A1* | 11/2012 | Bae ............ A61F 2/447 623/17.16 |
| 2013/0150968 A1 | 6/2013 | Dinville et al. |
| 2013/0166029 A1 | 6/2013 | Dinville et al. |
| 2013/0226300 A1 | 8/2013 | Chataigner et al. |
| 2014/0336771 A1 | 11/2014 | Zambiasi et al. |
| 2015/0051702 A1 | 2/2015 | Chataigner et al. |
| 2015/0250605 A1 | 9/2015 | Chataigner et al. |

FOREIGN PATENT DOCUMENTS

| | | |
|---|---|---|
| DE | 3741493 A1 | 6/1989 |
| DE | 20320454 U1 | 10/2004 |
| DE | 10323363 A1 | 12/2004 |
| EP | 0637439 A1 | 2/1995 |
| EP | 0697200 A1 | 2/1996 |
| EP | 0951879 A2 | 10/1999 |
| EP | 0965313 A1 | 12/1999 |
| EP | 2113228 A1 | 11/2009 |
| EP | 2327375 A1 | 6/2011 |
| EP | 2340788 A1 | 7/2011 |
| EP | 2363080 A1 | 9/2011 |
| EP | 2816977 A1 | 12/2014 |
| FR | 2703580 A1 | 10/1994 |
| FR | 2733413 A1 | 10/1996 |
| FR | 2747034 A1 | 10/1997 |
| FR | 2808995 A1 | 11/2001 |
| FR | 2823095 A1 | 10/2002 |
| FR | 2827156 A1 | 1/2003 |
| FR | 2846550 A1 | 5/2004 |
| FR | 2861582 A1 | 5/2005 |
| FR | 2879436 A1 | 6/2006 |
| FR | 2880795 A1 | 7/2006 |
| FR | 2891135 A1 | 3/2007 |
| FR | 2897259 A1 | 8/2007 |
| FR | 2916956 A1 | 12/2008 |
| FR | 2987256 A1 | 8/2013 |
| WO | WO-9508306 A1 | 3/1995 |
| WO | WO-9715248 A1 | 5/1997 |
| WO | WO-9801091 A1 | 1/1998 |
| WO | WO-9855052 A1 | 12/1998 |
| WO | WO-9909914 A1 | 3/1999 |
| WO | WO-9956676 A1 | 11/1999 |
| WO | WO-9963914 A1 | 12/1999 |
| WO | WO-0024327 A2 | 5/2000 |
| WO | WO-0170141 A1 | 9/2001 |
| WO | WO-0187194 A1 | 11/2001 |
| WO | WO-0213732 A2 | 2/2002 |
| WO | WO-02058599 A2 | 8/2002 |
| WO | WO-02089701 A2 | 11/2002 |
| WO | WO-03005939 A2 | 1/2003 |
| WO | WO-2004034935 A1 | 4/2004 |
| WO | WO-2004041129 A1 | 5/2004 |
| WO | WO-2004089256 A1 | 10/2004 |
| WO | WO-2006047587 A2 | 5/2006 |
| WO | WO-2006120505 A1 | 11/2006 |
| WO | WO-2007078978 A2 | 7/2007 |
| WO | WO-2007093900 A2 | 8/2007 |
| WO | WO-2008149223 A2 | 12/2008 |

(56) References Cited

FOREIGN PATENT DOCUMENTS

| WO | WO-2009033100 A1 | 3/2009 |
|---|---|---|
| WO | WO-2010090801 A2 | 8/2010 |
| WO | WO-201 1080535 A1 | 7/2011 |
| WO | WO-201 1129973 A1 | 10/2011 |
| WO | WO-201 3124453 A1 | 8/2013 |

OTHER PUBLICATIONS

"U.S. Appl. No. 10/276,712, Final Office Action dated Nov. 14, 2005", 7 pgs.
"U.S. Appl. No. 10/276,712, Final Office Action dated Dec. 20, 2006", 7 pgs.
"U.S. Appl. No. 10/276,712, Final Office Action dated Dec. 23, 2004", 6 pgs.
"U.S. Appl. No. 10/276,712, Non Final Office Action dated May 27, 2005", 7 pgs.
"U.S. Appl. No. 10/276,712, Non Final Office Action dated Jun. 7, 2006", 7 pgs.
"U.S. Appl. No. 10/276,712, Non Final Office Action dated Jun. 30, 2004", 9 pgs.
"U.S. Appl. No. 10/276,712, Notice of Allowance dated Jul. 30, 2007", 4 pgs.
"U.S. Appl. No. 10/276,712, Response filed Jan. 17, 2006 to Final Office Action dated Nov. 14, 2005", 9 pgs.
"U.S. Appl. No. 10/276,712, Response filed Mar. 1, 2005 to Final Office Action dated Dec. 23, 2004", 10 pgs.
"U.S. Appl. No. 10/276,712, Response filed Mar. 14, 2006 to Advisory Action dated Feb. 8, 2006", 8 pgs.
"U.S. Appl. No. 10/276,712, Response filed Jun. 19, 2007 to Final Office Action dated Dec. 20, 2006", 10 pgs.
"U.S. Appl. No. 10/276,712, Response filed Aug. 29, 2005 to Non Final Office Action dated May 27, 2005", 12 pgs.
"U.S. Appl. No. 10/276,712, Response filed Sep. 27, 2004 to Non Final Office Action dated Jun. 30, 2004", 12 pgs.
"U.S. Appl. No. 10/276,712, Response filed Oct. 6, 2006 to Non Final Office Action dated Jun. 7, 2006", 12 pgs.
"U.S. Appl. No. 10/483,563, Corrected Notice of Allowance dated Jun. 19, 2009", 4 pgs.
"U.S. Appl. No. 10/483,563, Final Office Action dated Oct. 28, 2008", 9 pgs.
"U.S. Appl. No. 10/483,563, Non Final Office Action dated Jan. 31, 2008", 8 pgs.
"U.S. Appl. No. 10/483,563, Non Final Office Action dated Feb. 21, 2007", 6 pgs.
"U.S. Appl. No. 10/483,563, Non Final Office Action dated Oct. 30, 2007", 6 pgs.
"U.S. Appl. No. 10/483,563, Notice of Allowance dated Jun. 5, 2009", 4 pgs.
"U.S. Appl. No. 10/483,563, Response filed Apr. 28, 2009 to Final Office Action dated Oct. 28, 2008", 8 pgs.
"U.S. Appl. No. 10/483,563, Response filed Jul. 31, 2008 to Non Final Office Action dated Jan. 31, 2008", 13 pgs.
"U.S. Appl. No. 10/483,563, Response filed Aug. 21, 2007 to Non Final Office Action dated Feb. 21, 2007", 12 pgs.
"U.S. Appl. No. 10/483,563, Response filed Nov. 19, 2007 to Non Final Office Action dated Oct. 30, 2007", 4 pgs.
"U.S. Appl. No. 10/533,846, Final Office Action dated Oct. 15, 2008", 13 pgs.
"U.S. Appl. No. 10/533,846, Non Final Office Action dated Apr. 18, 2007", 11 pgs.
"U.S. Appl. No. 10/533,846, Non Final Office Action dated Dec. 26, 2007", 14 pgs.
"U.S. Appl. No. 10/533,846, Notice of Allowance dated Nov. 4, 2009", 4 pgs.
"U.S. Appl. No. 10/533,846, Response filed Apr. 15, 2009 to Final Office Action dated Oct. 15, 2008", 13 pgs.
"U.S. Appl. No. 10/533,846, Response filed Jun. 25, 2008 to Non Final Office Action dated Dec. 26, 2007", 18 pgs.
"U.S. Appl. No. 10/533,846, Response filed Oct. 16, 2007 to Non Final Office Action dated Apr. 18, 2007", 16 pgs.
"U.S. Appl. No. 11/109,276, Final Office Action dated Jul. 24, 2008", 12 pgs.
"U.S. Appl. No. 11/109,276, Non Final Office Action dated Feb. 6, 2007", 12 pgs.
"U.S. Appl. No. 11/109,276, Non Final Office Action dated Feb. 13, 2009", 5 pgs.
"U.S. Appl. No. 11/109,276, Non Final Office Action dated Oct. 16, 2007", 12 pgs.
"U.S. Appl. No. 11/109,276, Notice of Allowance dated Dec. 8, 2009", 8 pgs.
"U.S. Appl. No. 11/109,276, Response filed Jan. 26, 2009 to Final Office Action dated Jul. 24, 2008", 9 pgs.
"U.S. Appl. No. 11/109,276, Response filed Apr. 16, 2008 to Non Final Office Action dated Oct. 16, 2007", 16 pgs.
"U.S. Appl. No. 11/109,276, Response filed Aug. 4, 2009 to Non Final Office Action dated Feb. 13, 2009", 8 pgs.
"U.S. Appl. No. 11/109,276, Response filed Aug. 6, 2007 to Non Final Office Action dated Feb. 6, 2007", 39 pgs.
"U.S. Appl. No. 11/378,165, Advisory Action dated Aug. 11, 2009", 3 pgs.
"U.S. Appl. No. 11/378,165, Applicant's Summary of Examiner Interview filed Feb. 26, 2013", 3 pgs.
"U.S. Appl. No. 11/378,165, Applicant's Summary of Examiner Interview filed Jun. 18, 2010", 1 pg.
"U.S. Appl. No. 11/378,165, Examiner Interview Summary dated May 20, 2010", 3 pgs.
"U.S. Appl. No. 11/378,165, Final Office Action dated Feb. 17, 2009", 16 pgs.
"U.S. Appl. No. 11/378,165, Final Office Action dated Sep. 24, 2010", 18 pgs.
"U.S. Appl. No. 11/378,165, Non Final Office Action dated May 27, 2008", 15 pgs.
"U.S. Appl. No. 11/378,165, Non Final Office Action dated Jun. 4, 2012", 27 pgs.
"U.S. Appl. No. 11/378,165, Non Final Office Action dated Oct. 26, 2009", 24 pgs.
"U.S. Appl. No. 11/378,165, Notice of Allowance dated Nov. 26, 2012", 10 pgs.
"U.S. Appl. No. 11/378,165, Response filed Feb. 28, 2008 to Restriction Requirement dated Sep. 28, 2007", 12 pgs.
"U.S. Appl. No. 11/378,165, Response filed Mar. 24, 2011 to Final Office Action dated Sep. 24, 2010", 15 pgs.
"U.S. Appl. No. 11/378,165, Response filed Apr. 26, 2010 to Non Final Office Action dated Oct. 26, 2009", 12 pgs.
"U.S. Appl. No. 11/378,165, Response filed Aug. 4, 2009 to Final Office Action dated Feb. 17, 2009", 14 pgs.
"U.S. Appl. No. 11/378,165, Response filed Nov. 5, 2012 to Non Final Office Action dated Jun. 4, 2012", 14 pgs.
"U.S. Appl. No. 11/378,165, Response filed Nov. 26, 2008 to Non Final Office Action dated May 27, 2008", 5 pgs.
"U.S. Appl. No. 11/378,165, Restriction Requirement dated Sep. 28, 2007", 9 pgs.
"U.S. Appl. No. 11/767,386, Final Office Action dated Mar. 24, 2011", 11 pgs.
"U.S. Appl. No. 11/767,386, Non Final Office Action dated Apr. 24, 2013", 10 pgs.
"U.S. Appl. No. 11/767,386, Non Final Office Action dated Jul. 21, 2010", 10 pgs.
"U.S. Appl. No. 11/767,386, Notice of Allowance dated Aug. 30, 2013", 6 pgs.
"U.S. Appl. No. 11/767,386, Response filed Jan. 21, 2011 to Non Final Office Action dated Jul. 21, 2010", 21 pgs.
"U.S. Appl. No. 11/767,386, Response filed Apr. 26, 2010 to Restriction Requirement dated Dec. 24, 2009", 9 pgs.
"U.S. Appl. No. 11/767,386, Response filed Jul. 24, 2013 to Non Final Office Action dated Apr. 24, 2013", 14 pgs.
"U.S. Appl. No. 11/767,386, Response filed Sep. 26, 2011 to Final Office Action dated Mar. 24, 2011", 18 pgs.
"U.S. Appl. No. 11/767,386, Response to Statement of Reasons for Allowance filed Dec. 3, 2013", 2 pgs.
"U.S. Appl. No. 11/767,386, Restriction Requirement dated Dec. 24, 2009", 5 pgs.

(56) References Cited

OTHER PUBLICATIONS

"U.S. Appl. No. 12/134,884, Non Final Office Action dated Jan. 31, 2012", 7 pgs.
"U.S. Appl. No. 12/134,884, Notice of Allowance dated Nov. 1, 2012", 7 pgs.
"U.S. Appl. No. 12/134,884, Response filed Jul. 31, 2012 to Non Final Office Action dated Jan. 31, 2012", 20 pgs.
"U.S. Appl. No. 12/279,664, Non Final Office Action dated Sep. 14, 2011", 13 pgs.
"U.S. Appl. No. 12/279,664, Notice of Allowance dated Apr. 11, 2012", 11 pgs.
"U.S. Appl. No. 12/279,664, Notice of Allowance dated May 29, 2012", 4 pgs.
"U.S. Appl. No. 12/279,664, Response filed Mar. 14, 2012 to Non Final Office Action dated Sep. 14, 2011", 21 pgs.
"U.S. Appl. No. 12/360,050, Non Final Office Action dated Sep. 6, 2011", 11 pgs.
"U.S. Appl. No. 12/360,050, Non Final Office Action dated Dec. 17, 2010", 14 pgs.
"U.S. Appl. No. 12/360,050, Notice of Allowance dated Mar. 26, 2012", 5 pgs.
"U.S. Appl. No. 12/360,050, Notice of Allowance dated May 18, 2012", 4 pgs.
"U.S. Appl. No. 12/360,050, Notice of Allowance dated Jul. 6, 2012", 5 pgs.
"U.S. Appl. No. 12/360,050, Notice of Allowance dated Aug. 2, 2012", 2 pgs.
"U.S. Appl. No. 12/360,050, Response filed Mar. 6, 2012 to Non Final Office Action dated Sep. 6, 2011", 14 pgs.
"U.S. Appl. No. 12/360,050, Response filed Jun. 16, 2011 to Non Final Office Action dated Dec. 17, 2010", 34 pgs.
"U.S. Appl. No. 12/424,364, Applicant's Summary of Examiner Interview filed May 22, 2012", 3 pgs.
"U.S. Appl. No. 12/424,364, Non Final Office Action dated Jan. 26, 2012", 10 pgs.
"U.S. Appl. No. 12/424,364, Non Final Office Action dated May 18, 2011", 10 pgs.
"U.S. Appl. No. 12/424,364, Non Final Office Action dated May 23, 2012", 6 pgs.
"U.S. Appl. No. 12/424,364, Notice of Allowance dated Jul. 24, 2012", 5 pgs.
"U.S. Appl. No. 12/424,364, Notice of Allowance dated Aug. 2, 2012", 2 pgs.
"U.S. Appl. No. 12/424,364, Response filed Feb. 27, 2012 to Non Final Office Action dated Jan. 26, 2012", 6 pgs.
"U.S. Appl. No. 12/424,364, Response filed Jul. 6, 2012 to Non Final Office Action dated May 23, 2012", 4 pgs.
"U.S. Appl. No. 12/424,364, Response filed Nov. 18, 2011 to Non Final Office Action dated May 18, 2011", 13 pgs.
"U.S. Appl. No. 12/430,768, Corrected Notice of Allowance dated Jan. 19, 2012", 2 pgs.
"U.S. Appl. No. 12/430,768, Non Final Office Action dated Jun. 14, 2011", 7 pgs.
"U.S. Appl. No. 12/430,768, Notice of Allowance dated Jan. 11, 2012", 5 pgs.
"U.S. Appl. No. 12/430,768, Response filed Dec. 14, 2011 to Non Final Office Action dated Jun. 14, 2011", 7 pgs.
"U.S. Appl. No. 13/158,761, Examiner Interview Summary dated Aug. 1, 2013", 3 pgs.
"U.S. Appl. No. 13/158,761, Examiner Interview Summary dated Oct. 31, 2012", 3 pgs.
"U.S. Appl. No. 13/158,761, Final Office Action dated Aug. 14, 2013", 11 pgs.
"U.S. Appl. No. 13/158,761, Final Office Action dated Oct. 22, 2014", 12 pgs.
"U.S. Appl. No. 13/158,761, Non Final Office Action dated Feb. 28, 2013", 10 pgs.
"U.S. Appl. No. 13/158,761, Response filed Jul. 29, 2013 to Non Final Office Action dated Feb. 28, 2013", 12 pgs.
"U.S. Appl. No. 13/158,761, Response filed Nov. 14, 2013 to Final Office Action dated Aug. 14, 2013", 12 pgs.
"U.S. Appl. No. 13/158,761, Response filed Nov. 19, 2012 to Restriction Requirement dated Oct. 17, 2012", 8 pgs.
"U.S. Appl. No. 13/158,761, Restriction Requirement dated Oct. 17, 2012", 6 pgs.
"U.S. Appl. No. 13/438,352, Non Final Office Action dated Aug. 14, 2014", 8 pgs.
"U.S. Appl. No. 13/520,041, Final Office Action dated Oct. 6, 2014", 10 pgs.
"U.S. Appl. No. 13/520,041, Non Final Office Action dated Mar. 20, 2014", 9 pgs.
"U.S. Appl. No. 13/520,041, Response filed Sep. 19, 2014 to Non Final Office Action dated Mar. 20, 2014", 5 pgs.
"U.S. Appl. No. 13/538,078, Non Final Office Action dated May 12, 2014", 12 pgs.
"U.S. Appl. No. 13/538,078, Notice of Allowance dated Oct. 20, 2014", 5 pgs.
"U.S. Appl. No. 13/538,078, Response filed Oct. 14, 2014 to Non Final Office Action dated May 12, 2014", 10 pgs.
"U.S. Appl. No. 13/585,063, Restriction Requirement dated Nov. 6, 2014", 8 pgs.
"U.S. Appl. No. 13/603,043, Final Office Action dated Jul. 24, 2014", 11 pgs.
"U.S. Appl. No. 13/603,043, Non Final Office Action dated Apr. 9, 2013", 13 pgs.
"U.S. Appl. No. 13/603,043, Non Final Office Action dated Nov. 21, 2013", 11 pgs.
"U.S. Appl. No. 13/603,043, Response filed May 21, 2014 to Non Final Office Action dated Nov. 21, 2013", 13 pgs.
"U.S. Appl. No. 13/603,043, Response filed Oct. 9, 2013 to Non Final Office Action dated Apr. 9, 2013", 37 pgs.
"U.S. Appl. No. 13/616,448, Non Final Office Action dated Aug. 22, 2013", 6 pgs.
"U.S. Appl. No. 13/616,448, Notice of Allowance dated Feb. 7, 2014", 5 pgs.
"U.S. Appl. No. 13/732,244, Non Final Office Action dated Sep. 19, 2014", 4 pgs.
"U.S. Appl. No. 13/732,244, Response filed Jul. 30, 2014 to Restriction Requirement dated Apr. 30, 2014", 4 pgs.
"U.S. Appl. No. 13/732,244, Restriction Requirement dated Apr. 30, 2014", 5 pgs.
"U.S. Appl. No. 13/774,547, Notice of Allowance dated Feb. 2, 2015", 5 pgs.
"U.S. Appl. No. 13/774,547, Notice of Allowance dated Jul. 3, 2014", 12 pgs.
"U.S. Appl. No. 13/774,547, Notice of Allowance dated Oct. 16, 2014", 8 pgs.
"U.S. Appl. No. 13/774,547, Preliminary Amendment filed Feb. 22, 2013", 8 pgs.
"U.S. Appl. No. 13/774,547, Preliminary Amendment filed May 1, 2013", 8 pgs.
"U.S. Appl. No. 13/854,808, Non Final Office Action dated Jul. 7, 2014", 12 pgs.
"U.S. Appl. No. 13/854,808, Response filed Jun. 18, 2014 to Restriction Requirement dated Apr. 18, 2014", 9 pgs.
"U.S. Appl. No. 13/854,808, Restriction Requirement dated Apr. 18, 2014", 9 pgs.
"U.S. Appl. No. 14/306,785, Non Final Office Action dated Oct. 22, 2014", 6 pgs.
"U.S. Appl. No. 14/380,714, Examiner Interview Summary dated Aug. 28, 2017", 2 pgs.
"U.S. Appl. No. 14/380,714, Final Office Action dated Aug. 7, 2017", 26 pgs.
"U.S. Appl. No. 14/380,714, Non Final Office Action dated Mar. 3, 2017", 25 pgs.
"U.S. Appl. No. 14/380,714, Notice of Allowance dated May 15, 2018", 6 pgs.
"U.S. Appl. No. 14/380,714, Notice of Allowance dated Nov. 9, 2018", 6 pgs.
"U.S. Appl. No. 14/380,714, Preliminary Amendment filed Aug. 23, 2014", 7 pgs.

(56) References Cited

OTHER PUBLICATIONS

"U.S. Appl. No. 14/380,714, Response filed Jan. 23, 2017 to Restriction Requirement dated Nov. 21, 2016", 10 pgs.
"U.S. Appl. No. 14/380,714, Response filed Jun. 5, 2017 to Non Final Office Action dated Mar. 3, 2017", 20 pgs.
"U.S. Appl. No. 14/380,714, Response filed Nov. 7, 2017 to Final Office Action dated Aug. 7, 2017", 22 pgs.
"U.S. Appl. No. 14/380,714, Restriction Requirement dated Nov. 21, 2016", 7 pgs.
"U.S. Appl. No. 14/380,714, Supplemental Amendment filed Feb. 7, 2018", 24 pgs.
"U.S. Appl. No. 14/721,818, Advisory Action dated Jun. 1, 2016", 3 pgs.
"U.S. Appl. No. 14/721,818, Appeal Brief filed Aug. 2, 2016", 22 pgs.
"U.S. Appl. No. 14/721,818, Appeal Decision dated Oct. 1, 2018", 11 pgs.
"U.S. Appl. No. 14/721,818, Examiner's Answer dated Mar. 30, 2017", 21 pgs.
"U.S. Appl. No. 14/721,818, Final Office Action dated Feb. 1, 2016", 19 pgs.
"U.S. Appl. No. 14/721,818, Non Final Office Action dated Sep. 24, 2015", 21 pgs.
"U.S. Appl. No. 14/721,818, Notice of Allowability dated May 7, 2019", 2 pgs.
"U.S. Appl. No. 14/721,818, Notice of Allowance dated Mar. 1, 2019", 7 pgs.
"U.S. Appl. No. 14/721,818, Notice of Allowance dated Oct. 11, 2018", 7 pgs.
"U.S. Appl. No. 14/721,818, Preliminary Amendment filed May 26, 2015", 8 pgs.
"U.S. Appl. No. 14/721,818, Reply Brief filed May 30, 2017", 8 pgs.
"U.S. Appl. No. 14/721,818, Response filed May 2, 2016 to Final Office Action dated Feb. 1, 2016", 13 pgs.
"U.S. Appl. No. 14/721,818, Response filed Dec. 28, 2015 to Non Final Office Action dated Sep. 24, 2015", 15 pgs.
"Australian Application Serial No. 2013224006, First Examination Report dated Oct. 17, 2016", 2 pgs.
"Australian Application Serial No. 2013224006, Response filed Jan. 24, 2017 to First Examination Report dated Oct. 17, 2016", 18 pgs.
"Canadian Application Serial No. 2,861,579, Office Action dated Dec. 20, 2018", 5 pgs.
"European Application Serial No. 02784881.1, Intention to Grant dated Aug. 26, 2010", 24 pgs.
"European Application Serial No. 02784881.1, Office Action dated Mar. 13, 2009", 2 pgs.
"European Application Serial No. 02784881.1, Office Action dated Aug. 4, 2009", 3 pgs.
"European Application Serial No. 02784881.1, Response filed Jul. 22, 2009 to Office Action dated Mar. 13, 2009", 21 pgs.
"European Application Serial No. 02784881.1, Response filed Oct. 14, 2009 to Office Action dated Aug. 4, 2009", 20 pgs.
"European Application Serial No. 05857774.3, Communication Pursuant to Article 94(3) EPC dated Apr. 11, 2011", 4 pgs.
"European Application Serial No. 05857774.3, Communication Pursuant to Article 94(3) EPC dated May 6, 2009", 3 pgs.
"European Application Serial No. 05857774.3, Response filed Oct. 11, 2011 to Communication Pursuant to Article 94(3) EPC dated Apr. 11, 2011", 20 pgs.
"European Application Serial No. 05857774.3, Response filed Nov. 13, 2009 to Communication Pursuant to Article 94(3) EPC dated May 6, 2009", 22 pgs.
"European Application Serial No. 07733892.9, Response filed Nov. 26, 2008 to Communication pursuant to Rules 161(1) and 162 EPC dated Oct. 27, 2008", 16 pgs.
"European Application Serial No. 08762820.2, Amendment filed Jan. 6, 2010", 23 pgs.
"European Application Serial No. 08762820.2, Communication Pursuant to Article 94(3) EPC dated Jan. 17, 2012", 4 pgs.
"European Application Serial No. 08762820.2, Response filed Jul. 27, 2012 to Communication Pursuant to Article 94(3) EPC dated Jan. 17, 2012", 23 pgs.
"European Application Serial No. 09009533.2, Extended European Search Report dated Oct. 6, 2009", 4 pgs.
"European Application Serial No. 09009533.2, Response filed Apr. 26, 2010 to Extended European Search Report dated Oct. 6, 2009", 10 pgs.
"European Application Serial No. 10185004.8, Extended European Search Report dated Apr. 6, 2011", 6 pgs.
"European Application Serial No. 11157596.5, Extended European Search Report dated Jun. 8, 2011", 5 pgs.
"European Application Serial No. 11165170.9, Extended European Search Report dated Jul. 21, 2011", 7 pgs.
"European Application Serial No. 11165170.9, Response filed Mar. 6, 2012 to Extended European Search Report dated Jul. 21, 2011", 17 pgs.
"European Application Serial No. 13170071.8, Extended European Search Report dated Oct. 1, 2013", 6 pgs.
"European Application Serial No. 13709337.3, Communication Pursuant to Article 94(3) EPC dated Feb. 18, 2016", 4 pgs.
"European Application Serial No. 13709337.3, Communication Pursuant to Article 94(3) EPC dated Dec. 11, 2018", 4 pgs.
"European Application Serial No. 13709337.3, Response filed Apr. 17, 2019 to Communication Pursuant to Article 94(3) EPC dated Dec. 11, 2018", 25 pgs.
"European Application Serial No. 13709337.3, Response filed Jun. 15, 2016 to Communication Pursuant to Article 94(3) EPC dated Feb. 18, 2016", 24 pgs.
"France Application Serial No. 0006351, Search Report dated Jan. 29, 2001", 1 pg.
"France Application Serial No. 0109381, Search Report dated Apr. 5, 2002", 2 pgs.
"France Application Serial No. 0213833, Preliminary Search Report dated Jul. 10, 2003", 2 pgs.
"France Application Serial No. 0413728, Preliminary Search Report dated Aug. 11, 2005", 2 pgs.
"France Application Serial No. 0601315, Search Report dated Oct. 11, 2006", 2 pgs.
"France Application Serial No. 0704155, Preliminary Search Report dated Jan. 30, 2008", 3 pgs.
"International Application Serial No. PCT/EP2013/053622, International Preliminary Report on Patentability dated Jul. 11, 2014", 4 pgs.
"International Application Serial No. PCT/EP2013/053622, International Search Report dated May 29, 2013", 3 pgs.
"International Application Serial No. PCT/EP2013/053622, Written Opinion dated May 29, 2013", 3 pgs.
"International Application Serial No. PCT/FR2001/001545, International Preliminary Examination Report dated Aug. 30, 2002", 16 pgs.
"International Application Serial No. PCT/FR2001/001545, International Search Report dated Sep. 5, 2001", 3 pgs.
"International Application Serial No. PCT/IB2002/003390, International Preliminary Examination Report dated Nov. 6, 2003", 4 pgs.
"International Application Serial No. PCT/IB2002/003390, International Search Report dated Mar. 3, 2003", 2 pgs.
"International Application Serial No. PCT/IB2003/004872, International Preliminary Examination Report dated Mar. 1, 2005", 6 pgs.
"International Application Serial No. PCT/IB2003/004872, International Search Report dated Mar. 3, 2004", 3 pgs.
"International Application Serial No. PCT/IB2005/004093, International Preliminary Report on Patentability dated Feb. 22, 2007", 8 pgs.
"International Application Serial No. PCT/IB2005/004093, International Search Report dated Aug. 31, 2006", 3 pgs.
"International Application Serial No. PCT/IB2005/004093, Written Opinion dated Aug. 31, 2006", 5 pgs.
"International Application Serial No. PCT/IB2007/000367, International Preliminary Report on Patentability dated Feb. 5, 2008", 9 pgs.

(56) References Cited

OTHER PUBLICATIONS

"International Application Serial No. PCT/IB2007/000367, International Search Report dated Oct. 22, 2007", 5 pgs.
"International Application Serial No. PCT/IB2007/000367, Written Opinion dated Oct. 22, 2007", 9 pgs.
"International Application Serial No. PCT/IB2008/001484, Amendment filed May 13, 2009", 33 pgs.
"International Application Serial No. PCT/IB2008/001484, International Preliminary Report on Patentability dated Aug. 5, 2009", 6 pgs.
"International Application Serial No. PCT/IB2008/001484, International Search Report dated Feb. 16, 2009", 5 pgs.
"International Application Serial No. PCT/IB2008/001484, Written Opinion dated Feb. 16, 2009", 8 pgs.
"International Application Serial No. PCT/IB2009/008048, Amendment filed Apr. 2, 2012", 24 pgs.
"International Application Serial No. PCT/IB2009/008048, International Preliminary Report on Patentability dated Apr. 18, 2012", 20 pgs.
"International Application Serial No. PCT/IB2009/008048, International Search Report dated Feb. 2, 2011", 6 pgs.
"International Application Serial No. PCT/IB2009/008048, Written Opinion dated Feb. 2, 2011", 15 pgs.
"LDR Medical, by its attorneys; Chapter II amendments for PCT Pub'n No. WO2006120505", App. No. PCT/IB2005/004093; dated Oct. 30, 2006; WIPO, 14 pgs.
"LDR Medical; Greffe et fusion", LDR Medical; France, (Sep. 19, 2004), 1 pg.
"LDR Medical; ROI Privilegier la greffe en creant la chambre de fusion", LDR Medical, (Sep. 19, 2004), 1 pg.
"Mc+ Le choix de l'ancrage", LDR Medical, (Sep. 19, 2004), 1 pg.
"European Application Serial No. 20163743.6, Extended European Search Report dated Apr. 14, 2021", 12 pgs.

* cited by examiner

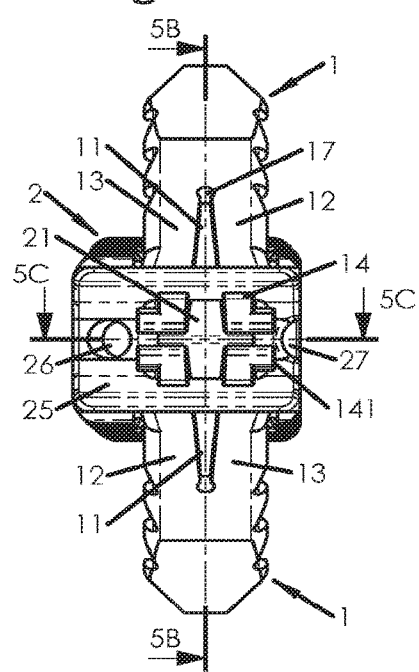
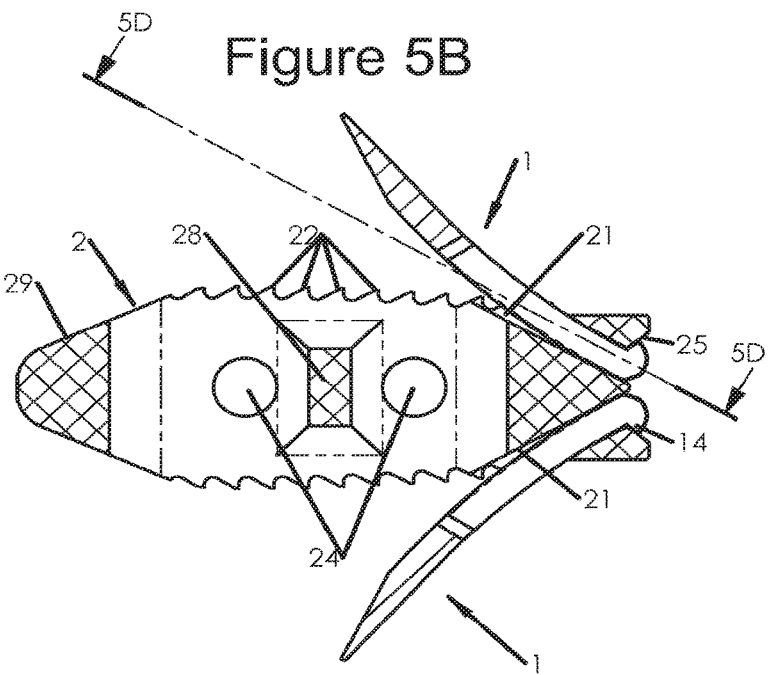
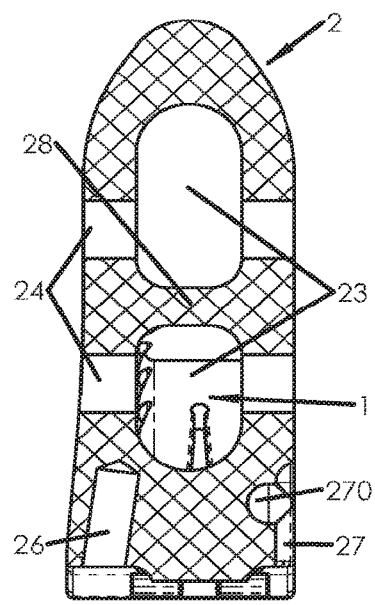
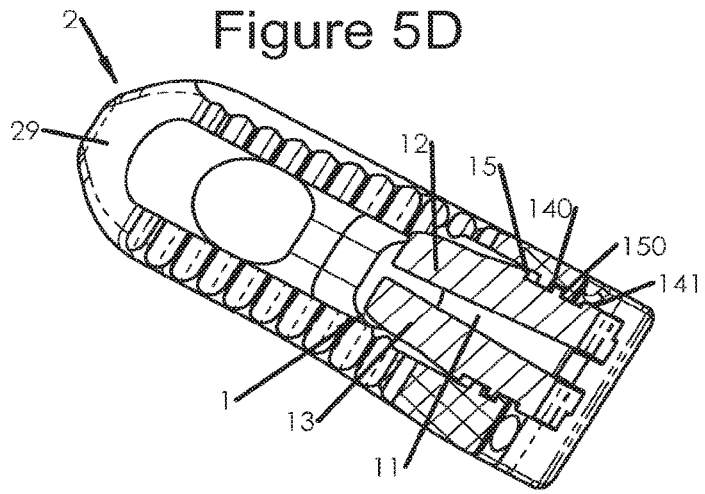

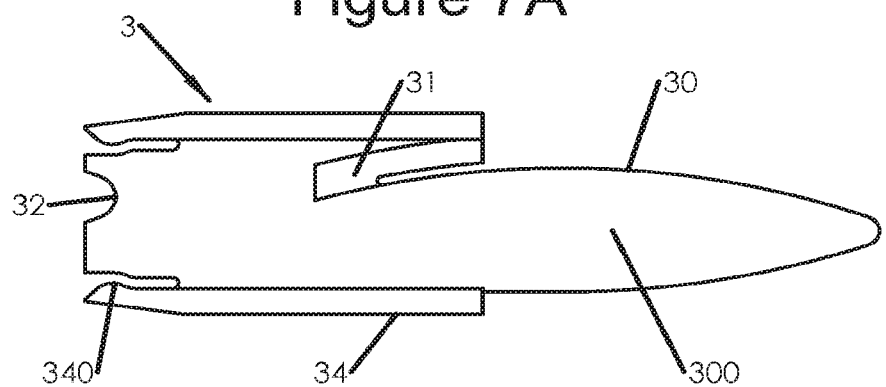
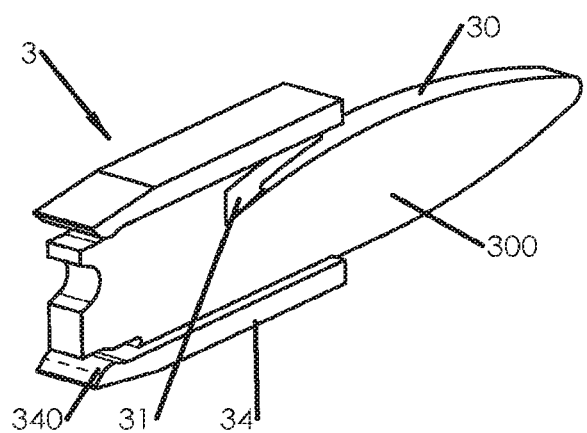
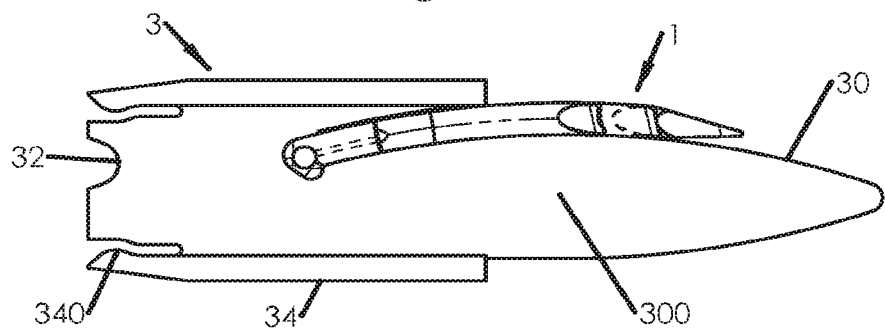

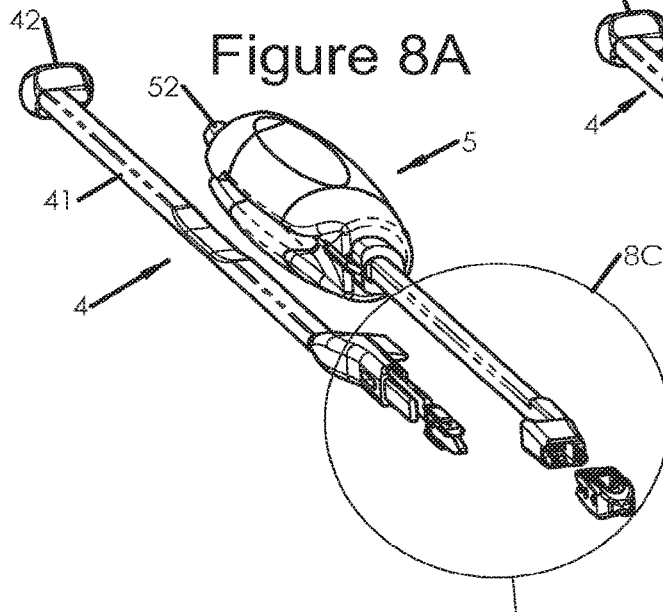
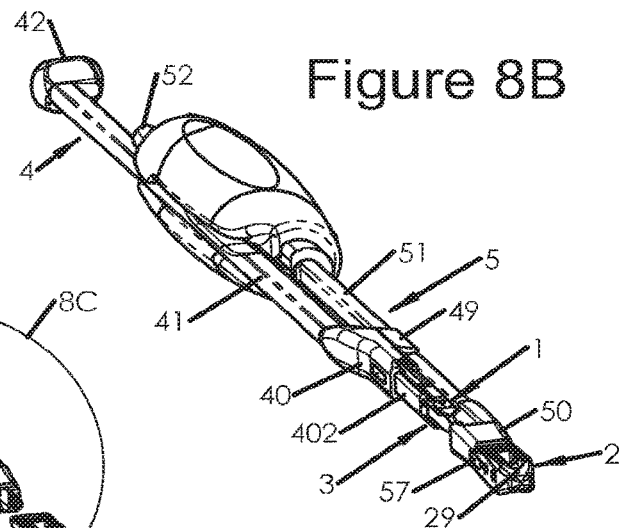
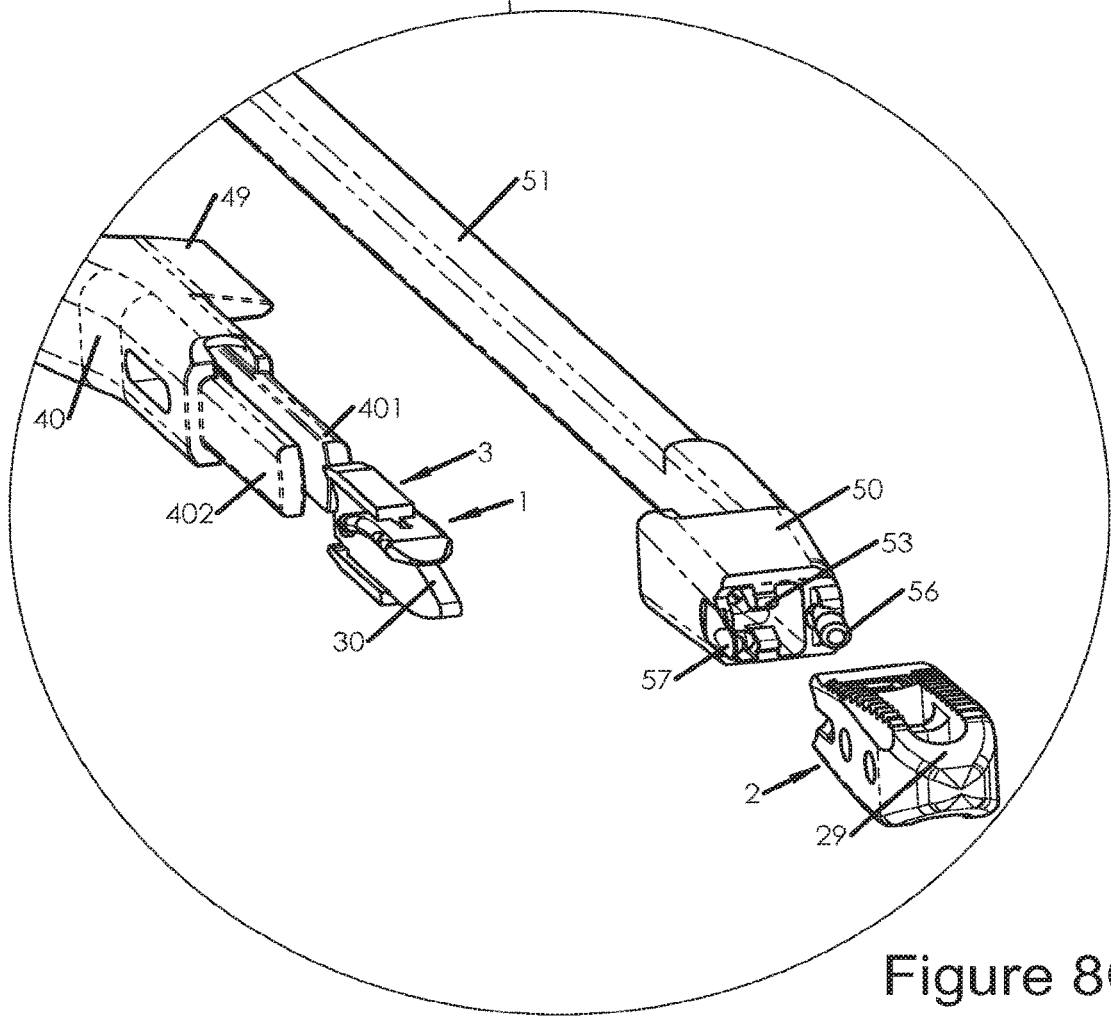

ANCHORING DEVICE AND SYSTEM FOR AN INTERVERTEBRAL IMPLANT, INTERVERTEBRAL IMPLANT AND IMPLANTATION INSTRUMENT

CROSS-REFERENCE TO RELATED APPLICATION

This application claims priority under 35 U.S.C. § 119 to French Patent Application No. 12/51733 filed in FRANCE on Feb. 24, 2012, which is incorporated herein by reference.

BACKGROUND

The present invention concerns orthopedic implants, including in particular spinal implants such as intersomatic (or interbody) cages, for example. Intersomatic cages may be implanted between two adjacent vertebrae for placement and growth of bone tissue grafts (or a substitute) in the disc space and to obtain an arthrodesis (the fusion of the two vertebrae). For example, after the cage is positioned, the intervertebral space may be filled with autologous spongy bone or suitable bone substitutes, which may also (or in the alternative) be placed in a cavity in the cage, prior to its positioning in the intervertebral space. In particular, the invention concerns intervertebral implants, implant anchors, the fixation of implants to vertebrae by anchors, and implantation of implants in the disc space by an implantation instrument.

One problem in this field concerns the stability of spinal implants in the disc space once they have been implanted, particularly when an arthrodesis is desired, for example using intersomatic cages or other implants allowing an arthrodesis (which may, for example, be deployed with auxiliary stabilizing structures such as osteosynthesis bars). For example, there is a risk that the implant will shift in the intervertebral space due to forces imposed when the patient moves, even when the implant is provided with notches or teeth on its vertebral contact surfaces. Therefore it is often necessary to affix the spinal implant to the adjacent vertebrae between which it is implanted. Osteosynthesis bars also are often provided for immobilizing the vertebrae, preferably with a lordosis, to prevent the cage from moving from the intervertebral space. Solutions are known in the prior art that provide the spinal implant with a bone anchoring device that allows solidly attaching the implant into the vertebral endplates of the vertebrae between which the implant is designed to be implanted.

Another problem in the field concerns the invasiveness and in particular the access to the intervertebral spaces (disc spaces) which is often particularly delicate due to the dimensions involved, particularly due to the presence of blood vessels and nerves in the approach to the intervertebral space. Bone anchoring devices must penetrate into the vertebrae with sufficient depth to ensure a good fixation, and must also have a small size and allow affixing the implant without endangering the surrounding blood vessels and nerves (for example, by not requiring more space in the approach to the intervertebral space than necessary for implantation of the spinal implant itself). In particular, some interbody cages are designed to be implanted with a posterior (from behind the patient) or transforaminal (through the foramen) approach (i.e., pathway). The posterior approach usually requires partial resection of the articular processes (joints) and passes between the dura and the articular processes (two cages disposed substantially parallel to the sagittal plane are generally provided). This approach thus uses a pathway which is very close to the spinal cord and requires cages of smaller size. The transforaminal approach use a pathway which is oblique to the sagittal plane and requires cages with dimensions that are reduced but with a sufficient length to be disposed obliquely or perpendicularly to the sagittal plane. The smallest possible access pathways are generally sought so as to limit the invasiveness of the surgical implantation. Moreover, in this spirit of limiting the invasiveness, one eventually tries to avoid having to install posterior material such as osteosynthesis bars (generally with pedicle screws). The use of anchoring means for attaching the cages could solve this problem if the anchoring means are reliable. The cages are usually placed between the vertebrae in an anterior position on the endplates, for allowing to impose a lordosis. Osteosynthesis bars can be used to maintain the lordosis which prevents the cage from sliding back, but anchoring means will be preferred instead if the fixation and stability of the implant obtained are reliable. Such anchoring means preferably also address the problem of limited invasiveness. Moreover, it is generally desired to be able to remove the bone anchoring means and the implant. This requires that the anchoring means be retained in bone implant stably but that they can also be removed as easily as possible with as little as possible invasiveness.

In the prior art, notably from published applications WO 2008/149223 and WO2011/080535 filed by the assignee of the present application, which are incorporated herein by reference and to which the reader can refer to examine various problems resolved and various advantages provided by this type of solution, an anchoring device is known, suitable to be implanted solidly and with sufficient depth in the vertebral endplates to ensure that the implant is held tight against these vertebrae, but along an axis of approach for insertion generally in the plane of the intervertebral space. This type of solution typically comprises at least one anchor formed of a curved and rigid plate, arranged so as to penetrate into the endplate of a vertebra through an implant and provided with at least one stop to hold this implant against this vertebra. The rigidity of this type of anchor is an important feature to allow effective fixation, notably more effective than staples or other thin and/or relatively flexible and often fragile devices. These types of anchoring devices (or "anchors") comprising a curved plate may pose a problem of the risk of splitting the vertebra during the impaction of the anchors into the vertebra, or due to forces imposed on the implant and/or the anchor once it is implanted in the vertebra. These types of anchors also may present a risk of making a cut that is too large during the impaction of the anchors into the vertebra, allowing the possibility of undesirable play of the anchor, which makes the implant fixation weak and/or unreliable. Application WO2011/080535 aims at solving to this type of problem. It should be noted that the term in impaction is used here to designate the fact that the anchoring device is driven into the vertebra. It will also be noted that the present application describes an impactor, which is a device for impaction of the anchor because it is arranged to help driving an anchoring device into a vertebra. Furthermore, another potential problem of these types of anchors having a curved plate concerns its rigidity. In some circumstances, it is important that the anchor is rigid enough that it will not deform and/or have much play under the effects of the forces that are exerted on it, so that it will not gradually come out of the vertebra in which it is embedded. In addition, passage of the anchor through the implant and maintenance of the stability of such anchor within the implant (subject to an eventual desired play, for instance minimum play) is also an aspect that is important to ensure reliable mounting in some circumstances. The application WO2011/080535 also aims at solving this type of stability problem. These anchoring devices provide a good anchoring solution with limited invasiveness, but they still require a substantial size to ensure a good stability in some cases and thus can be improved to limit the invasiveness even more, in particular for implantations through the posterior and/or transforaminal pathways. In addition, the withdrawal of this type of anchoring device is often problematic, in particular if an easy withdrawal is desired while preserving a limited invasiveness.

SUMMARY

Certain embodiments incorporating various technical features described the present application therefore aim to alleviate one or more of these and/or other disadvantages of the prior art by proposing an anchoring device for intervertebral implants that can be (more) compact (with lesser encumbrance) and (more) easily implantable, especially along an axis substantially perpendicular to the axis of the spine, and that can be rigid and allow (more) reliable fixation with reduced risk of damaging the vertebrae, in particular for implantations through the posterior and/or transforaminal pathways.

This goal is attained, for example, by a device for anchoring intervertebral implant in the vertebrae according to claim 1 of French Patent Application No. 12/51733.

Other features and advantages are presented in the claims of French Patent Application No. 12/51733 dependent from claim 1 of that application.

Another goal of certain embodiments incorporating various technical features described in the present application is to alleviate one or more of said (and/or other) disadvantages of the prior art by proposing an intervertebral implant that can be implanted substantially in the plane of the intervertebral space, which can be attached solidly to the vertebrae by means of an anchoring device that can be implanted substantially in the plane of the intervertebral space.

This goal is attained, for example, by an Intervertebral implant according to claim 19 of French Patent Application No. 12/51733.

Other features and advantages are presented in the claims of French Patent Application No. 12/51733 dependent from claim 19 of that application.

Another goal of certain embodiments incorporating various technical features described in the present application is to alleviate one or more of said (and/or other) disadvantages of the prior art by proposing an instrument for implanting intervertebral implants between vertebrae and implanting an anchoring device in at least one of these vertebrae, which allows implanting the implants substantially in the plane of the intervertebral space and implanting an anchoring device along an axis of approach substantially in the plane of the intervertebral space.

This goal is attained, for example, by an instrumentation for implanting intervertebral implant between the vertebrae and implanting at least one anchoring device in at least one of these vertebrae, according to claim 28 of French Patent Application No. 12/51733.

Other features and advantages are presented in the claims of French Patent Application No. 12/51733 dependent from claim 28 of that application.

BRIEF DESCRIPTION OF THE SEVERAL VIEWS OF THE DRAWING

Other features and advantages of various embodiments of the present invention will appear more clearly upon reading the description below, made in reference to the attached drawings, in which:

FIG. 5A shows a rear view of some embodiments of a cage that has two means of anchors and 5B and 5C show sectional views along the planes, respectively, 5B and 5C-5B-5C FIG. 5A and FIG. 5D shows a cross-section in the plane-5D 5D 5B;

FIGS. 7A and 7B are respectively a side view and a perspective view of some embodiments of a holder for an anchoring device and FIG. 7C shows a side view of a holder with a device anchor according to some embodiments;

FIGS. 8A and 8B are perspective views, respectively, exploded and assembled, certain embodiments of instrumentation for implantation of interbody cages and anchoring devices, equipped with one embodiment of the cage, holder for anchoring device and an anchoring device, FIG. 8C representing an enlargement of the portion 8C of FIG. 8A;

DETAILED DESCRIPTIONS

Figure 1A:
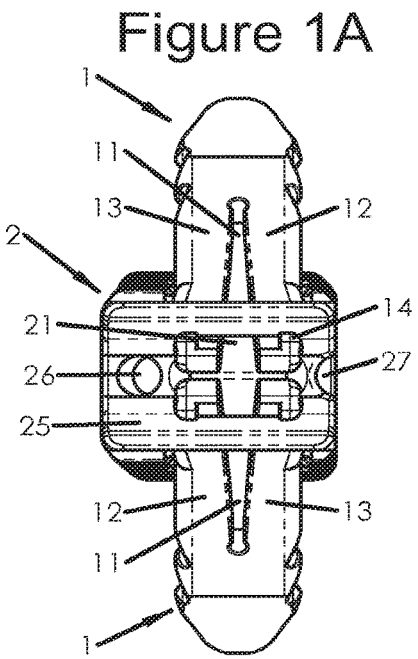
FIGS. 1A and 1B are respectively a rear view and a perspective view of some embodiments of a cage that has two means of anchors and FIGS. 1C, 1D and 1E represent, respectively, for a above, a profile view and a perspective view of an anchoring device according to these embodiments.

Various embodiments of the invention will now be described in reference to the figures of the present application. The invention simultaneously concerns three groups of objects:

anchoring devices (1) (or "anchors"), and/or anchoring systems comprising plural anchoring devices (1) that may be identical, different, or complementary;

intervertebral implants (2) configured for receiving one or more of such anchoring devices (1) or systems, including but not limited to interbody cages configured for an implantation through the posterior or transforaminal pathway; and instruments (3, 4, 5) for implanting implants (2) between the vertebrae and fixing implants with one or more anchoring devices (1) or anchoring systems.

Each group of objects may comprise various possible embodiments, relating to a given object. Each object comprises various elements (generally constituent of the object)

characterized by at least one technical feature. Each object (of a given group) concerned by at least one technical feature might be associated with at least one other object (of the same or another group), for example with respect to at least one complementary technical feature, such that the groups of objects share a common inventive concept. The invention may thus also concern an ensemble comprising at least two of these objects, as well as each object individually. The elements (for example a plate, a stop, a slit, a chamfer or bevel, etc.) and their technical features (for example a curvature, an orientation, a length, width, height, etc.) are described in more detail hereafter in the present application. At least one technical feature corresponding to an element of a given object solves at least one technical problem, in particular among those mentioned in the preamble of the present application. The present application thus describes various embodiments and configurations for each object or group of objects, by specifying at least one technical feature of at least one element. It will be understood from reading the present application that the various technical features of each element described in at least one embodiment or configuration may be isolated from other technical features of the object concerned by (or the objects concerned by and/or associated with) said embodiment or configuration (and thus concerning the same or another element) and/or may be combined with any other technical feature described herein, in various embodiments or configurations, unless explicitly stated otherwise, or unless these features are incompatible and/or their combination is not functional, in particular because the structural adaptations that may be required by such isolation or combination of features are directly derivable from the appreciation of the functional considerations provided by the present disclosure. Similarly, although some technical features are discussed herein in reference to the anchor device, they may be incorporated in various embodiments of the anchoring systems. Generally speaking, the specific technical feature(s) concerning a given element shouldn't be considered as exclusive from those concerning another element, nor from other technical features concerning the same element, except if it clearly appears that the combination of these technical features is impossible or nonfunctional. Although the present application details various embodiments or configurations of the invention (including preferred embodiments), its spirit and scope shouldn't be restricted to the examples given.

Various embodiments of anchoring devices (1) in accordance with the present invention are usable with intervertebral implants (2), such as, for example, intersomatic cages or intervertebral disc prostheses. Intervertebral implants are designed to be implanted between two adjacent vertebrae of the vertebral column (spine) or to provide a junction between two vertebrae, at their periphery in the case of osteosynthesis plates (which can be used alone or in combination with an intersomatic cage). Anchoring device (1) is designed to be anchored in one of the vertebrae so as to attach the implant to this vertebra. Various embodiments of anchoring devices (1) according to the invention comprise at least one curved and rigid plate, configured for penetration into a vertebra through an implant and comprise at least one stop to hold this implant against this vertebra. The technical features of "curvature" and "rigidity" concerning the "plate" element of the "anchor" object are described in detail below. Device (1) for anchoring intervertebral implant (2) in the vertebrae will also be referred to in the present application by the term "anchor" (1), without introducing any limitation whatsoever. This type of anchor has been described in publications WO 2008/149223 and WO2011/080535 of applications filed by the assignee of the present application, herein incorporated by reference in their entirety, but the present application concerns improvements in various structures and methods that may be used in various deployments to reduce the invasiveness of the surgical procedures necessary for the implantation of the implant and anchor. In various embodiments, anchor (1) comprises a body including at least one rigid curved plate (10) elongated along a longitudinal axis (L, FIGS. 1C and 2B). This longitudinal axis (L) of anchor (1) extends between a first end, which will be referred to as the anterior end, designed to penetrate into a vertebra, and a second end, which will be referred to as the posterior end. Note that the designations of the "posterior" and "anterior" ends of anchor (1), implant (2), and instrument (3, 4, 5) are used in the present application in reference to the direction in which anchor (1) will be inserted. Thus for anchor (1), the first end (referred to as the anterior end) is the one designed to be inserted first and designed to penetrate into a vertebra to affix an implant. Concerning the implant, its wall or end denoted as "posterior" is the one comprising an opening of a passage for the insertion of the anchor, whether this wall is really posterior to the implant or not during deployment. In the case of the interbody cages (2) described in the present application, this posterior end is generally disposed indeed at the rear of the patient since these cages are essentially intended for an implantation through the posterior or transforaminal pathway. Concerning the instrument, the anterior end is the one intended to be abutted on (or at least the closest to) the implant during implantation. Certain embodiments of implants (2), including some described in detail in this disclosure and concerning an intersomatic cage, are made for transforaminal insertion into the disc space, and accordingly the posterior end will be positioned on a lateral and rear side of the vertebrae, while the anterior end wilt be positioned near the front and opposite lateral slide. Nevertheless, the terms "anterior" and "posterior" will still be used since they are easier to understand from the point of view of implantation and may be commonly and conveniently used with reference to anchor (1), implant (2), and instrument (3, 4, 5) regardless of the implantation approach (implantation path) chosen. Accordingly, the terms "anterior" and posterior" are not intended to refer simply with respect to a patient or an anatomical feature of a patient. Furthermore, the terms "height" and "thickness" are used here to designate the dimensions of elements according to an orientation parallel to the axis of the spine (when implanted therein) and the terms "superior" and "inferior" are generally also defined according to this orientation (vertical when the patient is standing upright). Furthermore, the terms "width" and "length" here designate dimensions along a plane perpendicular to the axis of the spine (a transverse plane), with the width being generally in the medio-lateral direction while the length is in the antero-posterior direction. It will be noted as well that reference is made herein to a longitudinal axis (L) between these two ends and that this longitudinal axis (L) therefore corresponds to a anteroposterior axis of anchor (1) but that this definition is here extended to the implant (2) and instrument (3, 4, 5), still in reference to the direction of insertion of the anchor (1). It will also be noted that the term "substantially" is used several times in the present description, in particular concerning a technical feature such as an orientation or a direction, so as to indicate that the feature concerned may in fact be slightly different and not exactly as stated (for example, the expression "substantially perpendicular" should be interpreted as "at least approximately perpendicular" because it may be possible to choose an orientation which is not exactly perpendicular for allowing however to serve substantially the same function). Furthermore, the term "substantially" used in the present application may also be interpreted as defining that the technical feature may "in general" ("generally"), and often "preferably", as stated, but that other embodiments or configurations may be within the scope of the present invention.

In various embodiments, a bone anchoring device (1) for an intervertebral implant (2) is intended to be inserted, from the periphery of the spine, through a passage (21) passing through at least a portion of the implant (2). The device (1) in some embodiments comprises a body comprising at least one curved, rigid plate (10) elongated along a longitudinal axis (L) extending between a front end and a rear end. The anchoring device (1) (i.e., an anchor) may generally be formed by the plate (10), without comprising other structures extending beyond the plate and the elements that the latter comprises. Thus, the anchor may be constituted by at least one plate or may consist of at least one plate in some embodiments. The plate (10) in some embodiments is configured so that its front end enters at least one vertebra while its rear end remains in the passage (21) of the implant (2) or against the edge of the implant (2), thus pressing said implant (2) against said vertebra with at least one stop (e.g., retaining stops 14, 140) oriented angularly (i.e., not parallel) to the longitudinal axis (L) of the plate (10) and pressing against a complementary surface (25) of the implant (2) (e.g., on an edge or in the passage (21) of the implant). The plate (10) of the anchor (1) of various embodiments generally comprises at least one slot, (slit, gap, cutout, trim, etc.) (11), oriented substantially parallel to its longitudinal axis (L) and separating at least a rear portion of the plate (10) into two branches (12, 13). Thus, an anchor is obtained in some embodiments which can remain rigid, at least in some directions, but the slot allows the two branches (12, 13) to be moved bringing the two branches (12, 13) closer together. Such movement can be obtained by using a material for the branches (12, 13) having suitable deformation characteristics (e.g., compromise between rigidity and elasticity), or by use of structures of the plate such as a hinge, for example a specific region of each branch (12, 13) having suitable deformation characteristics. Generally, the length and/or width and/or shape of said slot (11) is (or are) configured to allow approximation of the two branches (12, 13) from each other, when a pressure is exerted thereon. Preferably, the plate will generally be metallic (biocompatible) to provide sufficient rigidity while allowing the elastic effect aimed by the slot. However, other materials are possible, such as PEEK or other materials suitable for implantation in the body and for the characteristics necessary for the implementation of the present invention.

Generally, the anchor (1), comprises, preferably on at least one of these branches (12, 13), at least one stop configured for retaining or locking the anchor (1) in the implant (2). Such retaining or locking of the anchor (1) in the implant (2) may be obtained in various embodiments by different types of latch, lock, stop, etc. In various advantageous embodiments, this retaining or locking is obtained by at least one withdrawal stop (15, 150), which can be oriented at an angle (i.e., not parallel) to the longitudinal axis (L) of the plate (10) and configured to cooperate with a complementary surface of the implant (2) and to retain the anchor (1) in the implant (2). Some embodiments of such withdrawal stop (15, 150) take advantage of the slot (11), as detailed below. In some embodiments, at least one withdrawal stop (15, 150) protrudes or projects from at least one of the branches (12, 13) of the device (1), on the side of the branch opposite the side adjacent to the slot (11). In some embodiments, at least one withdrawal stop (15) or at least one of the withdrawal stops (15, 150), disposed on one branch (12, 13) on the side opposite the slot, comprises at least one beveled surface, oriented generally facing the anterior end of the device (1), so as to form a slope facilitating insertion of the device (1) in the implant (2) and allowing the branches (12, 13) of the device (1) to be gradually brought closer to each other by the contact of this beveled or tapered surface with a wall of the passage (21) in the implant (2). Thus, with at least one withdrawal stop (e.g., 15, 150) on at least one of the branches (12, 13), the anchor will be retained from spontaneous and unexpected extraction from the implant. In some embodiments with a beveled or tapered surface, the slot (11) can allow the branches to squeeze together when inserting the anchor into the implant, with the branches restoring to their rest configuration when the device reaches a position within the implant where at least one withdrawal stop cooperates with a complementary surface of the implant, such as a housing in the passage receiving a protruding withdrawal stop for example (note that these stops are preferably positioned to be within the passage or near the passage, rather than the outside of the passage, after its outlet, where this spontaneous deployment of the withdrawal stop may be impeded by osseous tissue). In addition, the slit or slot facilitates voluntary withdrawal of the anchor by allowing the two branches to be brought closer to each other and, therefore, the withdrawal stop (15, 150) to disengage from its complementary locking surface of the implant. This arrangement has the advantage that the withdrawal stop (15, 150) may be smaller than alternative arrangements of flexible tabs or other structures, and may avoid the use of highly flexible structures that can be fragile. Moreover, locking configurations can be deployed that do not require too much room around the anchor to permit its removal (e.g., by disengaging the withdrawal stops). Indeed, these types of arrangements may avoid the need for channels in the implant (2) to access the withdrawal stops (15, 150) of the anchor (1) and therefore may permit reducing the size of the implant (2) (in addition to avoiding weakening that may result from using additional channels). It is therefore understood that these advantages of such arrangements generally address the problem of stability of fixation of the anchor and, therefore of the implant, and also address the problem of invasiveness due to reduced dimensional constraints.

Figure 1B:
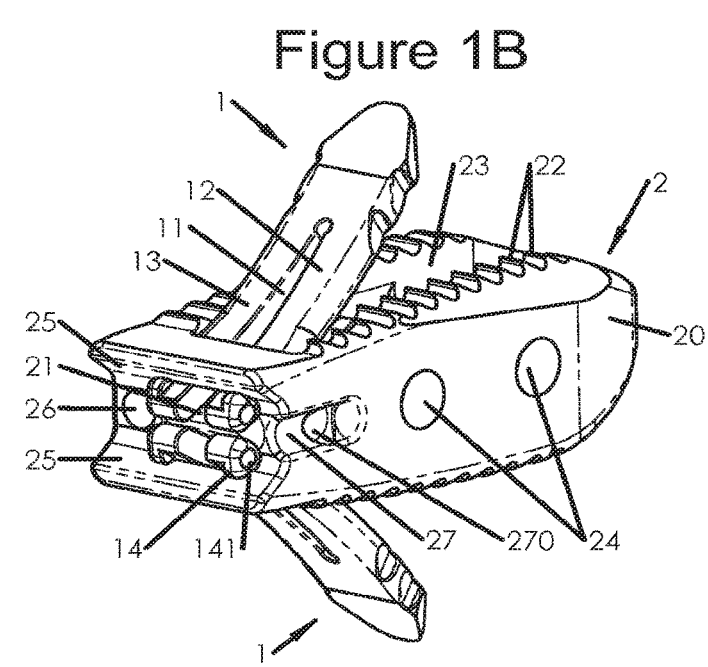
Figure 1D:
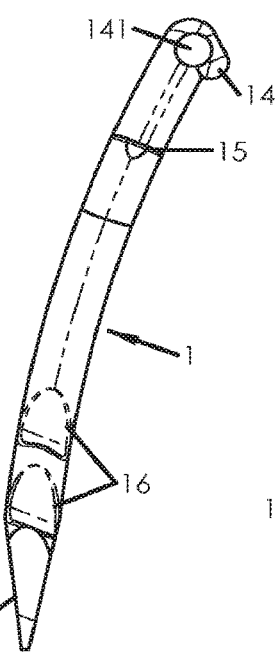
Figure 1E:
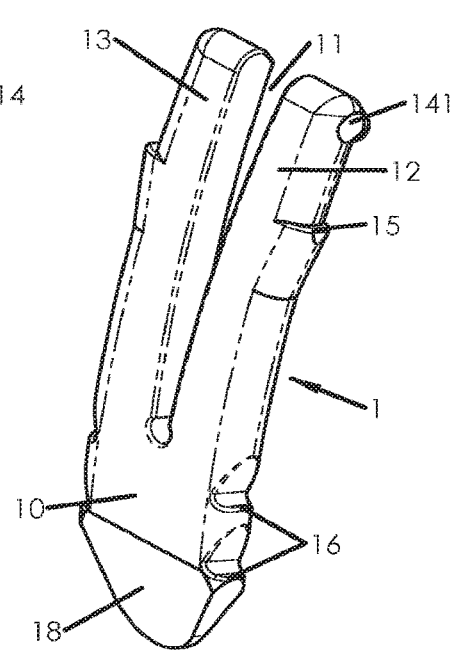
Figure 2A:
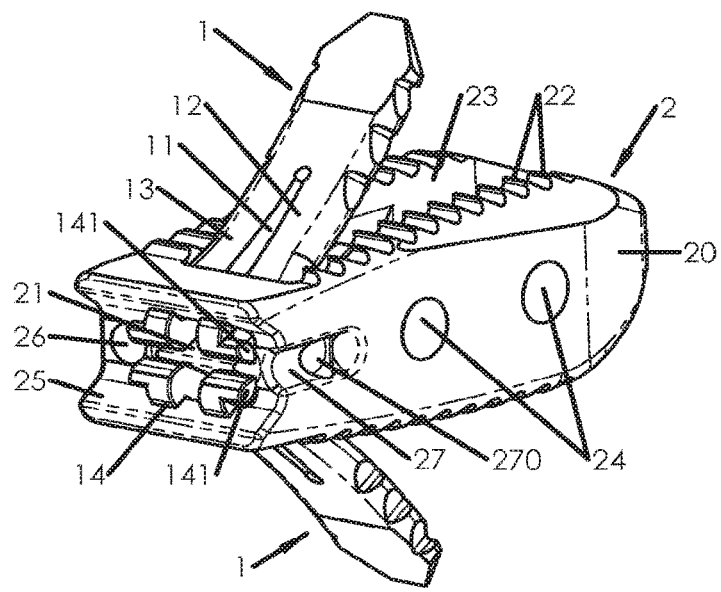
FIG. 2A shows a perspective view of some embodiments of a cage that has two means of anchors, 2B and 2C are respectively a top view and a perspective view of a device anchor according to these embodiments, FIGS. 2D and 2E representing respectively a perspective view and a side view of other embodiments of the anchor.
Figure 2B:
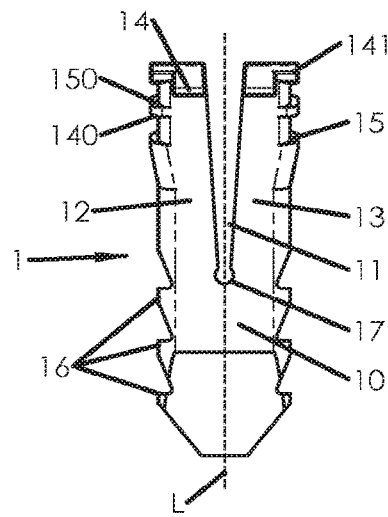
Figure 2C:
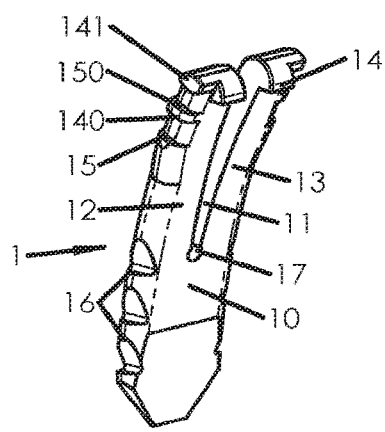

In some embodiments, the anchor (1) comprises at least one grip resource (141) on at least one of the branches (12, 13), configured to engage a tool for removing the anchoring device by squeezing the two branches (12, 13) closer to each other to disengage one or more withdrawal stops (15, 150). Engagement of a grip resource with a tool allows, while bringing the branches closer to each other for releasing the withdrawal stop(s) (15, 150), to pull the anchor and extract it from the implant (for example by pulling on the grip resource). A grip resource can thus enhance removal of the device (1) made possible by the slot (11). Such a grip resource may be formed simply by a housing in the rear end of the anchor, such as at a retaining stop as shown for example in FIGS. 1D and 1E. Other grip resources may be used, however, such as a lug or tab (141) projecting from the anchor or a portion of a retaining stop which is arranged to not be in contact with the implant and thus provide a housing for the insertion of a tool for pulling on the anchor. For example, FIGS. 2B and 2C show an anchor having a projecting tab (141) on the side edges of each leg (12, 13) of the anchor. As shown for example in FIG. 2A, this tab (141) does not form a retaining stop as it is not in contact with the surface (25) around the passage (21) of the implant, but another lug or tab (14) is forming a retaining stop. Note that, in other embodiments, such a tab (141) forming a grip resource can also form a retaining stop if it has a contact surface with the surface (25) around the passage (21) of the implant (while maintaining a surface without contact with the implant and substantially facing the implant to allow pulling on the anchor and thus form a grip resource).

In some embodiments, the curvature of the plate (10) extends along the thickness of the plate, that is to say that the curvature of the plate (10) defines a concave face (with the inside of the bend extending along the upper or lower face of the plate) and a convex face (with the outside of the bend extending along the opposite face of the plate) of the anchor (1), with the two sides (or edges) side of the anchor (1) joining the concave face and the convex face.

In some embodiments, at least one retaining stop (14, 140) comprises at least one stop surface oriented substantially facing the front end, intended to cooperate with at least one stop surface (25) on the implant (2) that the device (1) is intended to fix, so as to retain and press the implant (2) against the vertebra wherein the device (1) is designed to be anchored. For example, the retaining stop (14, 140) may comprise at least one projecting tab on at least one side and/or at least one edge of the plate (10). Note that the orientations of stops are often defined in this application as "angular to" and/or "not parallel to" the longitudinal axes as it is possible to provide for different orientations and because the least functional orientation would be parallel to the longitudinal axis as it would not form an abutment sufficiently effective to restrain movement along the longitudinal axis of the anchor. All other orientations are thus possible but it is generally preferred an orientation approximately perpendicular to the longitudinal axis for greater efficiency. In some embodiments, a single stop (14 or 140) for retaining may be provided, for example at the rear end of one branch (12, 13) of the plate (10). The retaining stops (14, 140) may be disposed anywhere on the plate in a position that results in contact with a surface (not parallel to the longitudinal axis of the anchor) of the implant (2) so as to press the implant (2) against the vertebra (i.e., anywhere along passage (21) before its outlet on the upper or lower surface of the implant). FIGS. 1A, 1B, 1C, 1D and 1E show illustrative and non-restrictive examples in which each branch has a retaining stop (14). Preferably, at least one stop is disposed at the rear end of the anchor so as to avoid the need for providing a complementary surface for receiving the stop that is within the passage of the implant. These stops can be formed, for example, by lugs, tabs, studs or other forms of projections extending from a face or edge of the plate. In these examples of FIG. 1, these stops are formed by a small projecting lug (14) on the concave face of the anchor, but it could be the convex face although the concave face is generally preferred so as not to hinder the impaction of a second anchor and/or so as to leave room for the stops of a second anchor fixing the implant to the other vertebra. In addition, provision may be made for at least one retaining stop (140) on at least one (or more) lateral edge(s) of the anchor rather than on one (or more) face(s). Both layouts or arrangements can also be provided at the same time. For example, in FIGS. 2B and 2C, a first type of retaining stop (14) is arranged on one side of the anchor (on each of two branches in these non-limiting examples) and a second type of retaining stop (140) is obtained by a structure projecting on at least one lateral edge of the plate (on a side edge of each of the two branches in these non-limiting examples).

Figure 6A:
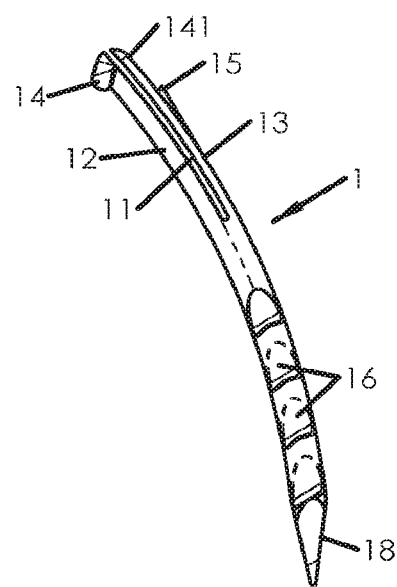
FIGS. 6A and 6B are respectively a side view and a perspective view of some embodiments of an anchoring device and FIGS. 6C and 6D show respectively a side view and a perspective view other embodiments of the anchor.
Figure 6B:
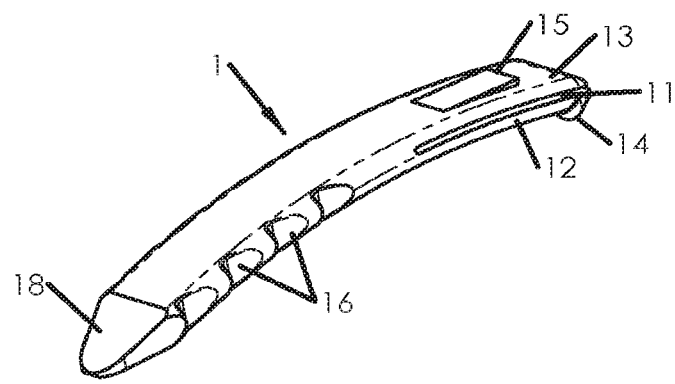
Figure 6C:
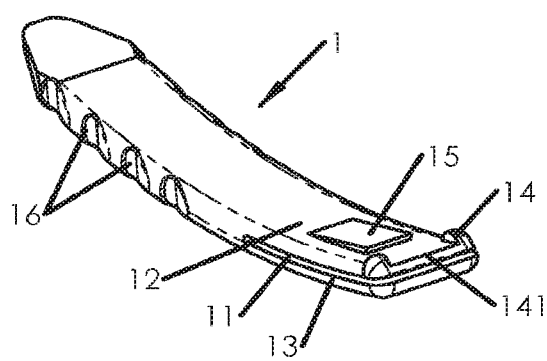
Figure 6D:
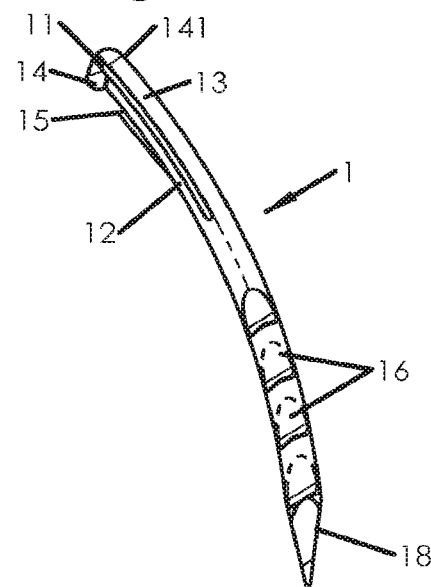

In some embodiments, illustrative and not limiting examples of which are shown in FIGS. 6A, 6B, 6C and 6D, a slot (11) separates the plate (10) in its thickness. This produces a slotted plate (10) with a branch (12) on the concave face and a branch (13) on the convex face. In some of these embodiments, one of the two branches (12, 13) comprises at least one withdrawal stop (15, 150) while in other embodiments each of the two branches may comprise at least one withdrawal stop (15). In some embodiments having a withdrawal stop (15) on a single face, it is the branch (13) of the convex face which comprises at least one withdrawal stop (15), such as shown in FIGS. 6A and 6B, while in other embodiments it is the branch (12) of the concave face which comprises at least one withdrawal stop (15), such as shown in FIGS. 6C and 6D.

Figure 2D:
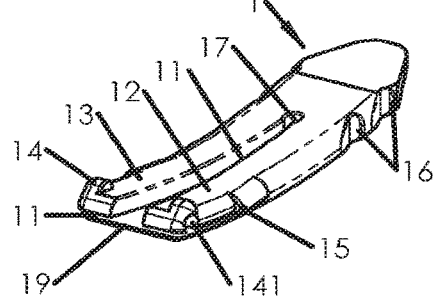
Figure 2E:
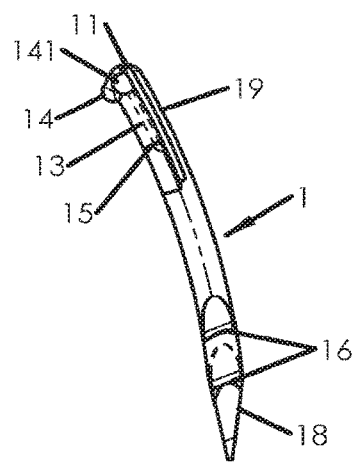

In some embodiments, at least one slot (11) separates a plate (10) in its width. This gives a branch (12, 13) on each of two lateral faces of the plate (10). In some embodiments, there is provided a combination of these two possible orientations of the slot. In such embodiments, a longitudinal slot separates the plate in its width, but not over its entire thickness and a longitudinal slot separates a rear portion of the plate in its thickness. One thus obtains a portion of the anchor split in its width where one plate (19) stiffens the rear of the anchor, for example as shown in FIGS. 2D and 2E. Preferably, in these embodiments with at least one slot splitting the plate in its width, each of the two branches comprises at least one withdrawal stop (15, 150), such as shown in most of the figures showing anchors with two lateral branches. In some embodiments, each branch may comprise several withdrawal stops (15, 150), preferably with at least one beveled surface on the one (or those) which is (are) the closest to the front end. For example, FIGS. 2B and 2C show a non-limiting illustrative example of such an anchor that includes a first withdrawal stop (15) and a second withdrawal stop (150) disposed a little more posterior than the first. The implant then preferably has a second surface complementary to this second stop and oriented to prevent the backing out of the anchor from the implant (i.e., with an orientation angular (not parallel) to the longitudinal axis of the anchor and preferably perpendicular), for example as shown in FIG. 5D. Note that the second withdrawal stop (150) may be obtained by a structure (a bulge for example) which may also from a retaining stop (140), as defined in this application by reference to the retaining stops (14, 140) since its anterior surface (according to naming convention defined in the this application) has a surface angular (not parallel) to the longitudinal axis and located on the side towards the front end (preferably substantially facing the front end) of the plate and adapted to oppose the advance of the anchor in the implant if it has a complementary surface to receive or abut it, for example as shown in FIG. 5D. This second withdrawal stop (150), cooperating with such a complementary surface of the implant is able to hold the implant in the same way (achieve substantially the same function) as the retaining stops (14, 140) defined in this application. However, some embodiments of the retaining stops (14, 140) defined in this application are disposed closer to the posterior end of the anchor and thus have the advantage of providing a retaining stop without the need for complementary surface within the passage (21) of the implant (2) (i.e., without the need for housing along the walls of the passage to allow accommodation of a bearing surface for the stop, which is relatively difficult to manufacture). Also, some embodiments of the retaining stops (14, 140) defined in this application are disposed on the face rather than the edge of the anchor and thus have the advantage of providing a retaining stop (14) which stops the anchor even though its branches are close to each other. It is therefore generally preferred to provide at least one retaining stop (14, 140) for the anchor, although it may contain several withdrawal stops (15, 150) with at least one (150) being capable of forming a retaining stop by the fact that it comprises an abutment surface towards the front end. Note that providing retaining stops (14) on the concave and/or convex face of the anchor split in its width (or conversely a stop on an edge of an anchor split in its thickness) allow to stop the anchor even if its branches (12, 13) are moved towards one another, which would not necessarily be the case for withdrawal stops (140) on the side edges that are eventually, depending on their length, capable of forming a retaining stop only if the branches are in the rest position, that is to say at a distance from each other (and pose a risk that the anchor penetrates too far into the implant and is stuck with its branches close to each other and their side stops inside the passage). However, the implantation generally uses an instrumentation preventing the anchor from penetrating too deep in the implant (and preventing the retaining stop to be inserted in the passage in various configurations). Indeed, the impactor described hereafter is generally configured with a stop surface preventing from pushing the anchor too deep and adjusted or adjustable as a function of the shape and/or dimensions of the anchor and/or implant. Furthermore, preference may also be for the lateral retaining stops (140) because they may reduce the space needed above and below the anchors unlike the stops (14) arranged on at least one face (concave and/or convex), in particular because it is sometimes possible to provide lateral retaining stops (140) which are long enough to function even when the branches are moved towards each other (to prevent the anchor from penetrating too far into the implant). In other configurations, for example those of the interbody cages intended for implantation through the posterior or transforaminal pathway, the approach imposes constraints on the width of the implant and therefore the retaining stops (e.g. 14, 140) are preferably protruding from the faces (convex and/or concave) of the anchor, so as not to require enlarging the width, in particular when at least one grip resource (26, 27) is provided near the passage (in the vicinity or on the lateral faces of the implant). Depending on the configuration and direction in which congestion is the most troublesome, it is possible to choose the most suitable locations and/or shapes stops to minimize the size (in height and/or in width) of the elements (components) and the objects (and thus the invasiveness), while ensuring a reliable device.

Using at least one plate (10) allows anchor (1) to ensure a good hold, at least in a direction substantially perpendicular to the plate, since the width of the plate offers a surface opposing movement of the anchor and thus of the implant (perpendicularly to this surface) in the bone tissue in which it is implanted, it will be noted that when the plate is curved, this hold is created along at least one direction substantially radial to the radius of curvature of the plate. In fact, various embodiments of the present invention, like various embodiments of the one described in the applications cited above, have the advantage of a having curvature that allows it to be implanted in the vertebral endplate of a vertebra along an approach axis substantially perpendicular to the axis of the spine at the level of the vertebrae between which the implant is implanted (or in the plane of the intervertebral space), which may facilitate implantation and allow avoiding some of the disadvantages linked to the encumbrance (dimensions) of the approach to the vertebrae by minimizing the invasiveness of the surgical approach to the intervertebral space needed to implant the anchor. Thus, the curved plate (10) of the body preferably describes at least one circular or elliptic arc having dimensions and at least one radius of curvature arranged such that the anchoring device (1) can be implanted in an endplate along an approach axis forming an angle of approximately 90° with the axis of the spine, by presenting the anchor's longitudinal axis (L) substantially in the plane of the intervertebral space. It is understood that various embodiments of the anchor are designed to penetrate from the periphery of the disc space into the vertebrae, preferably into the inferior vertebral endplate of the upper vertebra or into the superior vertebral endplate of the lower vertebra, in particular in the case of implants such as intersomatic cages or intervertebral disc prosthesis. Also, other embodiments of the anchor may be configured for implantation preferably into the periphery of the vertebral body near the intervertebral space, especially in the case of intervertebral implants such as osteosynthesis plates. When an anchor is intended for implantation into the vertebral plate, for example through implants such as intersomatic cages or intervertebral disc prosthesis, the curvature of the anchor is preferably configured so that, once embedded in a vertebra, the axis of the spine is substantially tangential to a substantial part of its anterior extremity, or at least that this part of the anterior end forms a small (or slight) angle with the vertical axis of the spine.

In various embodiments the anchor advantageously has the shape of a plate which may be relatively thin, facilitating the penetration of anchor (1) into the bone tissue. This thinness of plate (10) may pose a problem of stability of anchor (1) in the vertebra, to the extent that the plate might form a sort of blade that can split the vertebra in a direction along the width of the plate (transversely to longitudinal axis (L) of various embodiments), notably during its impaction in the vertebra, or later, due to the significant stress applied thereon when the patient moves, for example. Furthermore, this thinness may diminish the rigidity of the plate. In some applications rigidity may be an important feature for effective fixation, resulting in embodiments particularly more effective than staples or other thin and/or relatively flexible, often fragile, devices, which do not allow a good hold due to their flexibility and/or thinness and/or their fragility. Therefore, rigid anchors are preferred for many embodiments (curved anchors being also preferred, but for facilitating the approach to vertebrae) instead of deformable anchors. Rigid anchors penetrate into the vertebrae through a passage (21) crossing at least a part of the implant without being deformed in this passage (21). For these rigid embodiments, inner walls of this passage (21) in the implant preferably have shapes and dimensions that allow the anchor to pass: either by a curvature complementary to that of the anchor, or by an uncurved shape with a height slightly greater than that of the anchor to permit its passage despite its curvature and rigidity (thus avoiding machining a curved passage in the implant, which may be complex and costly).

Various embodiments of the present invention resolve problems of stability and rigidity of anchor (1) by using at least one longitudinal rib over at least one part of at least one of the faces of the body of anchor (1). This longitudinal rib preferably is orientated in the direction of the length of plate (10), substantially parallel to longitudinal axis (L) in various embodiments, for example such as described in application WO2011/080535 owned by the assignee of the present application. However, as the anchor is provided with a slot

(11) on at least a rear portion, the rib will be preferably on a portion of the anchor which is not split, thus on a front portion of the anchor.

Moreover, it is generally preferred to solve, in various embodiments of the present invention, any eventual stability problems by means, resources, arrangements or configurations other than a rib, because a rib generally will impose size constraints on the implant (which typically will have a groove to accommodate the rib), while many of the present embodiments generally aim to minimize the invasiveness and thus the size of elements (items) and objects of the invention. Some of these other configurations to solve the problem of potential instability of the anchor may for example include a bone growth through the anchor to stabilize it (although it requires time for growth to take place) and/or provide an anchor of sufficient thickness and with lateral edges soft enough (i.e., not sharp) to avoid splitting the vertebrae. In addition, using a sufficiently rigid material may provide good stability despite the absence of rib and the presence of a slot, while maintaining a size which still limits the invasiveness. Indeed, using appropriate configurations of a slot can allow making the posterior portion of the anchor flexible enough for the release of the withdrawal stops, but allow keeping the anchor very rigid overall, because the stops can be configured very small in size relative to the rest of the anchor. In addition, the compromise between the flexibility of the two branches and the overall rigidity of the anchor may be controlled with appropriate configurations of the shapes and dimensions of the slot and/or the branches.

In some embodiments, the plate (10) defines, by its curvature, an average arc (AM, FIGS. 3D and 3E) between its front and rear ends, and has two arms (12, 13) which are offset with respect to each other on opposite sides of the average arc (AM). FIGS. 3A, 3B, 3C, 3D, 3E and 3F show illustrative and not limiting examples of such a configuration of the branches of the anchors (and associated examples of embodiments of implants in FIGS. 3A and 3B). In these embodiments, the two arms are offset and can be brought closer to each other so that one comes one above the other. This arrangement reduces the width of the slot required for the approximation of the branches and may limit the overall width of the anchor. On the other hand, this arrangement, by providing branches which are offset, provides a larger contact surface of the anchor, laterally to the plate, with the bone of the vertebra, and therefore a greater resistance allowing to reduce the risk of cutting the bone by a lateral movement of the anchor in the bone. This type of arrangement of anchor (1) with offset branches usually requires adapting the shape and dimensions of the passage (21) in the implant, as detailed below. Indeed, such anchors with offset branches often require that the passage is enlarged. However, in some embodiments, which FIGS. 3A, 3B, 3C, 3D, 3E and 3F illustrate non-limiting examples, the anchor (1) is arranged so that it is not necessary to enlarge passage (21) of the implant (2) too much to allow the insertion of the anchor (1). Indeed, in these embodiments, the anterior portion of the anchor which is not split comprises two portions, each in the extension of one of the branches, which are also offset with respect to each other (in the same direction as the branches). This offset provides the anterior part of the anchor (1) a form adapted to the shape of the passage (21) of the implant (2) which is necessary to retain the posterior part of the anchor (1). Thus, the passage (21) may be adjusted to the posterior part of the anchor (1) and the front part adapted to the passage (21). Note that the passage preferably still has a central portion adapted to pass the part forming the offset between the two anterior sections. Other simpler solutions are possible even if they do not usually allow obtaining a passage as well adjusted (and retaining the anchor as best as possible). For example, it is possible to thin-down an anterior portion of the anchor for it to pass more easily through the passage without enlarging the passage too much, but the passage should then still contain a portion adapted to pass an anterior portion of the anchor shaped as a plate substantially tangent (or parallel) to the average arc (AM), while the branches are offset with respect to this average arc. Note that the offset of the branches and of the anterior portions is more important toward their posterior end than toward the anterior end. Therefore, in such embodiments, at least one of the branches preferably comprises, on the edge adjacent the slot, preferably at least near the front end of the slot, at least one bevel surface or chamfer to avoid an eventual friction of the two branches when they are brought closer together. Alternatively or additionally, it is possible to widen the slot at its front end to prevent contact between the branches.

Figure 4A:
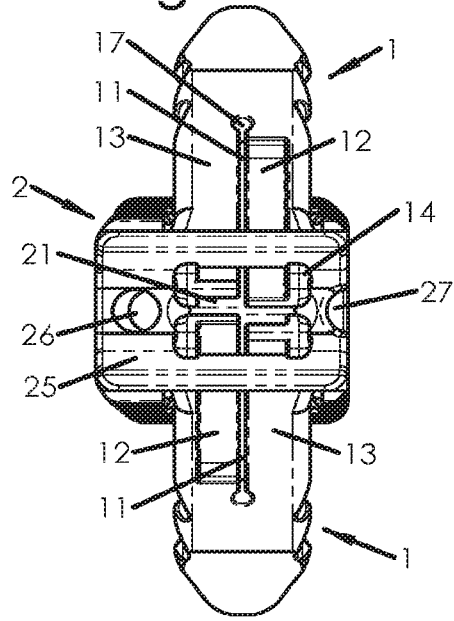
FIGS. 4A and 4C are views back to different embodiments of interbody cages equipped with two anchoring devices and 4B and 4D are perspective views of various embodiments of anchoring devices.
Figure 4B:
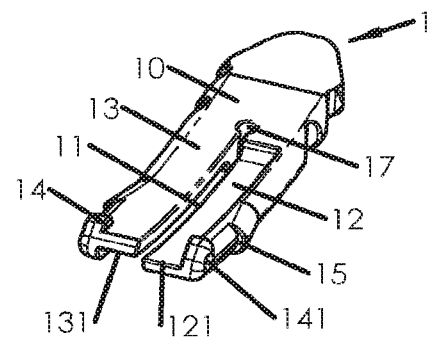

In some embodiments, the two arms (12, 13) have shapes that are complementary to one another, configured so that at least one rear portion of one of the branches (e.g., 12, 13) can cover at least one rear portion of another of the branches (e.g., 12, 13), at least partially, without increasing the total thickness of the device, when the two branches are brought close to each other. FIGS. 4A and 4B show illustrative and not limiting examples of such a configuration of the branches of the anchors (and associated exemplary embodiments of implants in FIG. 4A). This arrangement reduces the width of the slot required for the approximation of the branches and may limit the overall width of the anchor. In some embodiments the branches may actually at least partially overlap at rest, which allows to reduce the overall width of the anchor. Furthermore, some of these arrangement, by providing for branches that are not symmetrical but complementary, may provide for bone ingrowth, for example thanks to housing provided by the complementarity of shape of the branches, and which may quickly provide a way to limit the risk of cutting the bone by a lateral displacement of the anchor in the bone.

Figure 4C:
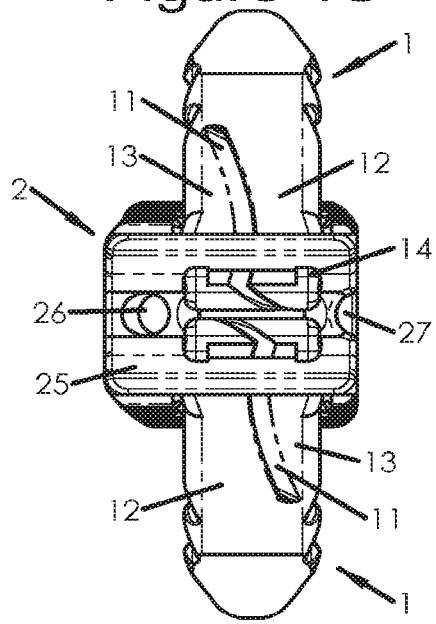
Figure 4D:
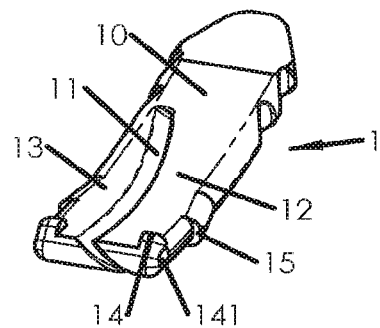

In some embodiments, at least one slot (11) may be formed in the thickness of the plate (10) but not in a plane perpendicular to the width of the plate (10). In some embodiments, a slot (11) may deviate partially or totally from the longitudinal axis describing a curvature. FIGS. 4C and 4D show illustrative and not limiting examples of a combination of these independently deployable aspects of embodiments of slots (11) of an anchor (and an exemplary embodiment of an associated implant in FIG. 4C). Indeed, in these figures, the slot has an oblique orientation in the thickness of the plate (it does not cross perpendicularly). Furthermore, the slot is curved in the length of the plate. Although presented in combination in this figure, it will be understood that one can separate these two features and provide an anchor such as in FIG. 4B, but with an oblique slot facilitating the approximation of two branches in an extreme position. In addition, in these examples, the curvature of the slot deviates from the longitudinal axis (L) towards a lateral edge of the anchor. In other examples, the slot may describe a curvature substantially centered on the longitudinal axis (L). Using a curvature deviating toward an edge of the anchor, one obtains an anchor with a branch (13) more flexible than the other branch (12), which may be advantageous in some configurations. For example, the withdrawal stop(s) (15) may then be provided only on this branch (13) more flexible than the other, so as to facilitate the disengagement of the withdrawal stop(s) (15) when the anchor is desired to be removed. Furthermore, the branch (12) which is less flexible than the other may provide for a better overall rigidity of the anchor.

Figure 1C:
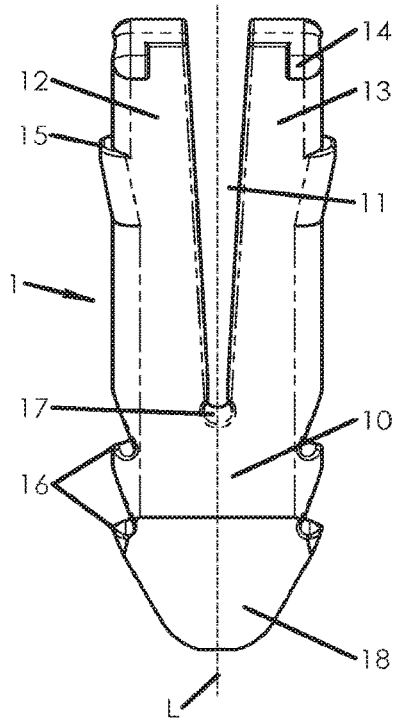

Various embodiments of anchors with regard to the length of the anchor itself and/or the length of the slot (11) are possible. Indeed, anchors of different lengths (and different curvatures) may be provided for a more or less deep anchoring depending on the application. In addition, as mentioned above, the length and/or width and/or shape of said slot (11) is (or are) configured to allow approximation of the two branches (12, 13) together, when pressure is exerted thereon. In some embodiments, the length of slot (11) is preferably at least greater than the width (or to a quarter of the length) of the device (1). It is even generally preferred that the length of the slot (11) is greater than the third of the length, or even half of the plate (10) to facilitate the approximation of two branches. However, a compromise is generally reached between the various parameters which may impact on the risks of weakening the anchor or making it too flexible, such as for example the length of the slot (which may not depend on the length of the plate), the width of the slot, the section of the plate (dimensions in height and/or thickness), the size of the anterior end not split, etc. Also, the width of the slot may vary depending on the application, and embodiments may be used where the width of said slot (11) varies along the longitudinal axis (L) of the plate (10). For example, FIG. 1C shows a slot whose width is greater at the rear end than at the front end. It is not necessary, indeed, that the slot is very wide at its front end as the approximation of the branches typically is desired mostly at the posterior end of the anchor. In some embodiments, for example if the plate has a width such that it is not possible (or too difficult) to obtain an approximation of the branches with a single longitudinal slot, the slot may have a more complex shape, adapted to allow the approximation of the branches (for example a T-shape or any other suitable configuration). It is also possible to arrange a plurality of slots (11), of various shapes, in the plate (10) if necessary. In addition, the slot can optionally allow bone growth through the plate (10), which stabilizes the anchor (and therefore the implant). Embodiments are therefore provided for where the slot is wide or flared (e.g., portion 17) at its front end, to facilitate bone growth through the anchor. One can also provide, in addition to the slat, at least one hole passing through the thickness of the plate (10) to allow bone growth through the device (1) once implanted.

In various embodiments, the front end of the slot (11) is provided with a portion (17) configured to prevent the plate from splitting in the extension of the slot under the effect of stress on the anchor. Such a portion (17) may for example be rounded such as shown in FIG. 1C, but it is sufficient to provide a surface may not parallel to the longitudinal axis (preferably perpendicular) to reduce the possibility of shear or splitting.

The present invention is not limited regarding the number or positions of the anchors deployed, although certain configurations are particularly advantageous, notably in terms of resistance or size of the implant, for example, in the case of the cervical implant, where the small size places strong constraints on the size and where the strength of the materials requires that the implants not be made excessively fragile by passages (21), especially in the case of intersomatic cages made of PEEK (polyether ether ketone).

In various anchor and anchor system embodiments of the invention, plate (10) can be substantially rectangular, as is shown in many of the figures, but can, of course, have various other shapes without departing from the spirit of the invention. Preferably, whatever the shape of the periphery of the plate, it presents at least one surface of sufficient dimension for efficiently apposing its movements in the vertebra, contrarily to staples, nails or other known devices. For example, most of the plates shown in the figures have a substantially rectangular periphery, but have variations in shape described in detail in the present application. Moreover, anchor (1) can comprise several plates, and/or a single plate of the body can have various shapes without departing from the spirit of the invention. In fact, to the extent that the desired hold can be obtained by at least one plate offering at least one surface sufficient in the dimension described here as the width of the plate, the anchor can comprise plates having a substantially trapezoidal or triangular periphery or having diverse shape variations. For example, in certain variants of anchor (1) (not shown), the body of anchoring device (1) may have two plates substantially parallel to one another and/or with substantially the same curvature) and connected together at the posterior end, for example, such as described in publications FR 2,827,156 (and WO 03/005939 and US 2004/0199254) and FR 2,879,436 (and WO 2006/120505 and US 2006/0136063), each of which is incorporated herein by reference, which may form a stop holding anchor (1) on the implant and thus holding the implant against the vertebra. In addition, various embodiments of anchors (1) may comprise at least one straight plate, for example such as described in these publications, or comprise 2 straight plates connected by a link able to, or configured to, form a stop allowing to affix the implant. Generally, various anchor embodiments of the invention may use a slot (11) to allow bringing the branches close to each other and this slot may achieve its function even if the branches in fact form the rear end of double plate.

Various embodiments of the invention strive to reduce the size of the devices and associated instruments, so as to allow implanting the anchoring device along an axis substantially in the plane of the intervertebral space (disc space). As described in publications of applications WO 2008/149223 and WO2011/080535 cited above and incorporated herein by reference, curved plate (10) describes, along the longitudinal axis, at least one arc of a circle and/or at least one arc of an ellipse whose dimensions and radii of curvature are created so that anchoring device (1) can be implanted in the vertebral endplate of a vertebra by having its perpendicular axis substantially in the plane of the intervertebral space, i.e., along an axis of approach substantially perpendicular to the axis of the spine (i.e., said plane or said approach axis being substantially tangential to at least part of the anterior end when the anchor approaches the vertebrae). Similarly to the above cited applications, various embodiments of the various objects of the present invention concern the technical feature of the radius (or radii) of curvature of anchoring device (1). Various embodiments of anchoring device (1) in fact have a different radius of curvature from one anchor to another, and/or several different radii of curvature on different portions of the body of a given anchor (1). Thus, for example, the body of anchor (1) may have an arc of a circle or arc of an ellipse shape, but it may also describe a more complex curvature, as if several arc(s) of a circle, having a same radius of curvature or different radii of curvature, were placed end to end or if several arc(s) of an ellipse, having a same radius of curvature or different radii of curvature, were placed end to end, or any combination of arcs of a circle or ellipse or even a radius of curvature that varies along the body. In the present description, the terms "arc of a circle" or "radius of curvature" encompass all these different possibilities. Thus, various embodiments of the present invention provide different variants concerning the radius of curvature and certain related aspects of anchoring device (1), as well as implants (2) and instruments (3, 4) that may be associated with it. In fact, for example, depending on the use of device (1) and in particular its intended implantation location along the spine, it may be preferable to have a larger or smaller radius of curvature. Depending on the radius of curvature of anchoring device (1), the axes passing, respectively, through the penetration end and the stop end of device (1) form an angle, typically comprised between approximately 90° and 180°, although it may also be chosen to be less than 90°. Preferably, this angle will be comprised between 110° and 160°, which, in many circumstances, will facilitate implanting the device better than an angle outside these values. According to the fixation that one wishes to obtain by means of anchoring device (1), the angle will be selected to be more or less open. If one wishes, for example, to promote tight affixation of the cage or the prosthesis against the vertebral endplate, an angle comprised between 120° and 180° may be preferred, while if one wishes rather to prevent the implant from moving in the plane of the disc space, an angle comprised between 90° and 150° may be preferred. Although these angle variations are not shown in the figures, different angles for anchoring device (1) permit covering the different desirable types of anchoring in order to assure a fixation of the implants that is adapted to the case. A device (1) whose angle is at an optimal value, for example near 135°, can also be provided in one of the preferred embodiments for fixation of the device both by pressing the implant tight against the vertebral endplates and preventing it from moving in the plane of the disc space. Moreover, according to the various embodiments of implant (2), different angles can be chosen for the device, particularly to permit a good fixation despite possible lordosis, kyphosis, or even scoliosis, whether it be natural, pathological, or imposed by the implant. Thus, various embodiments of anchoring device (1) and of implant (2), by means of its radius of curvature and the orientation of passage (21) into which it will be inserted, can be implanted along an axis of approach substantially in the plane of the intervertebral space, i.e., the plane in which implant (2) is implanted, which facilitates the approach of all the elements of the implant and the device to the intervertebral space. In one embodiment, the arc (or arcs) described by the body of anchor (1) has (or have) dimensions and at least one radius of curvature so that anchoring device (1) can be implanted in a vertebral endplate along an axis of approach forming an angle comprised between 40° and 140° with the vertical axis of the spine and, preferably, an approximately 90° angle. This angle can vary for a same anchoring device (1) depending on the dimensions of the approaches to the vertebra and can also vary from one anchoring device (1) to the other depending on the radius of curvature of device (1) used (and therefore the angle formed between its anterior and posterior ends). Furthermore, various embodiments provide for an anchor (1) comprising at least one straight (uncurved) plate (10). Note that in the case of straight anchors (1) (i.e., comprising at least one straight plate), the approach axis may preferably not be substantially in the plane of the disc space but may be oblique. This type of oblique axis is not generally preferred because of the encumbrance of the access to vertebrae but it is still possible to use in some circumstances. The implants (2) used with such straight anchors (1) preferably comprise at least one straight passage (21), oriented toward at least one vertebra, along an oblique path (not perpendicular to the axis of the spine) between the periphery of the spine and the vertebrae. The instrumentation used with such implants (2) with straight passages and such straight anchors (1) preferably will have a contact surface with the implant, at the anterior end, inclined with respect to its longitudinal axis (antero-posterior according to the convention used in the present application), so as to allow an oblique approach axis relative to the vertebrae. Furthermore, various embodiments of anchor (1) may also have a body comprising at least two straight plates (10) (or plate portions) forming an angle between each other. These straight plates (10) (or plate portions) may for example be linked by at least one connective portion forming such angle (for example thanks to a curvature of this connective portion). These various embodiments may for example be used in association with implants (2) comprising a curved passage (21), for example so as to facilitate the passage of anchor (1) and/or assure a minimum play of anchor (1) within the implant (2), thanks to contact of various parts or portions of the anchor (1) with various parts or portions of inner walls of the passage (21). Various embodiments of anchor (1) may also have a body comprising at least one straight plate (10) (or plate portion) and at least one curved plate (10) (or plate portion). These various configurations of the body of anchor (1) allow providing various embodiments of potential objects of the invention, concerning anchors comprising various portions. These particular objects can be configured to solve the problem(s) of facilitating the passage of anchor (1) through the implant (2) and/or to improve the stability of anchor (1) within the implant (2) and/or limit the invasiveness. Anchoring systems (and associated implants and instrument) are also provided for, in which various embodiments of the anchors and features described herein and in applications et WO2008/19223 and WO2011/080535 may be combined. These particular objects (e.g., any of these embodiments comprising at least one straight and/or curved plate (or plate portion) in their body) may also comprise or not, according to various embodiments, any technical feature (or combination of technical features) described for any element (or combination of elements) of any object (or combination of objects) disclosed in this application, as long as they are not incompatible, in particular because the structural adaptations that may be required by such isolation or combination of features are directly derivable from the appreciation of the present disclosure.

Anchoring device (1) generally cooperates with at least one passage (21) crossing through a portion of the implant that it is intended to affix. Such a passage can be a conduit or a channel, for example, of shapes and sizes arranged for the passage of the anchoring device, particularly in cross-section (for example, a substantially rectangular cross-section with rounded angles). Preferably, passage (21) is straight, so as to facilitate its machining, and its dimensions are arranged for the passage of a curved and rigid anchoring device (1) without requiring deformation of this device regardless of its radius of curvature. In various embodiments in which anchor (1) is curved, the height (of the opening) of the passage is therefore preferably slightly greater than the thickness of anchoring device (1), sufficiently to allow the passage of this device inside passage (21), without deformation regardless of its curvature and its rigidity, but sufficiently small to assure a good retention of implant (2) by anchoring device (1), without too much play of the device inside passage (21). In certain embodiments of the invention, the width of passage (21) can be substantially equal to the width of device (1) so that this device has little or no lateral play once it is inserted into passage (21). The length of anchoring device (1) may be adapted to the length of passage (21) to be crossed and the depth to which it must penetrate in the vertebral endplates.

In some configurations, the anterior end of anchor (1) is designed to penetrate into a vertebra adjacent to the implantation's location of the implant (2) to be affixed. In certain embodiments of anchor (1), for example as shown in FIG. 1, the anterior end has at least one chamfer (18) or a bevel facilitating the penetration of anchor (1) into the vertebra. In some embodiments, this anterior end can comprise a cutout, for example in the form of a notch, facilitating the penetration of the anterior end into the vertebral endplates. Also note that the inner edges of the notch may or may not be sharpened. Generally, since the anterior end is the one designed to penetrate into the vertebral endplate and may guide the rest of anchor (1), it is preferred that it be made so as to facilitate penetration into the bone tissue. In certain embodiments, this anterior end may thus comprise at least one point. Thus, the figures of the present application show an anterior end configured substantially into the shape of a point (as further explained elsewhere in this disclosure). It is understood that this end can be sharpened (or ground), but that since bone tissue can be relatively resistant, it is preferable to preserve the integrity of this anterior end. Thus, as can be particularly seen in FIG. 1, for example, the anterior end preferably has a chamfer on each of the faces of plate (10) and the lateral sides of the plate are beveled so as to reduce the width of the anterior end. Preferably, these bevels terminate at a distance from one another and the anterior end is therefore terminated by a plane or curved surface which is relatively sharp. On the other hand, as previously mentioned, it is preferable for anchor (1) to penetrate easily into the vertebrae without risking splitting them beyond the dimensions of anchor (1). Thus the lateral sides (or edges) of plate (10) (of the body in general) will preferably be flat, as shown in most of the figures. Hence, in general, the lateral sides of the plate (10) of the anchor (1) preferably are flat, so as to avoid splitting the vertebrae.

As mentioned above, so as to enhance an anchor's ability to hold an implant (2) against a vertebra, various embodiments provide for it to be stopped against at least one surface of the implant that it is intended to affix, so as to hold the implant against the vertebral endplate, preferably firmly pressed against it. In various embodiment of anchoring device (1), the body accordingly comprises at least one retaining stop (14). Retaining stop (14) (preferably has at least one stop surface oriented facing the anterior end. Preferably, this surface is oriented approximately perpendicular to the longitudinal axis and is facing the anterior end, whether it is positioned at the posterior end or further towards the front. This retaining stop (14) is designed to cooperate with at least one stop surface of a complementary stop (25) provided on implant (2) that device (1) is designed to affix, in order to hold implant (2) against the vertebra in which anchoring device (1) is designed to be anchored. In various embodiments, stop (25) preferably comprises at least one stop surface oriented facing the posterior end (i.e., toward the periphery of the implant), in order to cooperate optimally with retaining stop (14). These cooperating stop surfaces can have various configurations, for example, flat, curved, prismatic, and so on. Note that retaining stop (14) is preferably at the posterior end, as most of the figures of the present application show. In many configurations, retaining stop (14) is positioned at the level of (i.e., at or in the vicinity of) the posterior end so that it is located at, or near to, the entrance to passage (21) in the implant, abutting the complementary surface of stop (25) of the implant. This surface of the complementary stop (25) may, for example, be a surface of the peripheral wall of the implant, but it may preferably be formed by a recess, so that stop (14) doesn't protrude from (or extend beyond) the implant when anchor (1) is fully inserted therein. Furthermore, it is understood that stop (14) can be further toward the front of the anchor, so that it can be found inside passage (21), for example, as long as a complementary stop surface (25) of the implant is suitably positioned. The position of retaining stop (14) at the level of the posterior end, however, in many embodiments has the advantage of offering a good hold of the implant, particularly when the anchor is configured to contact the implant from the entrance of the passage up to the outlet. In addition, this posterior position may be preferred when configuring the implant (2) and the anchor (1) to facilitate an intentional withdrawal of the anchor, as discussed for various configurations elsewhere in this disclosure.

In certain embodiments of anchor (1), retaining stop (14) comprises at least one part protruding from at least one of the faces and/or sides (or edges) of the anchor (1). For example, the retaining stop (14) may comprise at least one projecting lug. For example, retaining stop (14) comprises two projecting lugs on a same face of anchoring device (1), in particular the convex face. In other configurations, at least one projecting lug can be provided on any face and/or sides (or edges), or at least one lug can be provided on each face and/or sides (or edges), or there can be any other variant in the same spirit. In certain embodiments of anchor (1), retaining stop (14) comprises at least one projecting lug on at least one lateral side or edge of the body of anchoring device (1). Preferably, at least one lug will be positioned on each of the 2 lateral sides, so as to improve the hold, As these example configurations of retaining stop (14) show, the term "projecting lug" used here should not be interpreted in a limiting manner, and the precise form of the lug can vary, for example between a small plate offering planar stop surfaces and a small stud offering curved stop surfaces, or any other variant, although some particular shapes may have various advantages, for example in terms of an efficient hold or of a voluntary withdrawal of the anchor. In addition, retaining stop (14) can have various orientations, so as to hold anchor (1) in the implant and hold the implant tight against the vertebra in an optimal manner. Several different retaining stops (14) can also be provided, positioned at different places on anchor (1). In some embodiments of anchor (1) and implant (2), the shapes of retaining stop (14) and complementary stop (25) can be arranged so that stop (14) of the anchor is mated with or locked to stop (25) of the implant, for example by locking lugs engaging a recess. In the case of anchors (1) with two curved plates connected by an uncurved portion or in the case of a single plate with a curved portion (hook-shaped, such as in publications FR 2,879,436, WO 2006/120505 and US 2006/0136063, each of which is incorporated herein by reference, particularly in the case of fixation of prostheses), this portion can serve as a retaining stop, cooperating with a shaft or at least one surface situated at the entrance of passage (21), for example. Anchoring device (1) is removable in numerous embodiments and can be implanted in the vertebrae and mated with the implant after it is installed between the vertebrae, which allows possible adjustment of the position of the implant between the vertebrae before definitive fixation by anchor (1). In some embodiments, the retaining stop can be used to pull the anchor (1) to remove it from the vertebrae, and the implant if necessary (e.g., in the case of a curved hook or a grip resource (141) providing a way to pull on the anchor as mentioned above).

It should be noted that the withdrawal stops may be positioned at various locations on the plate (10) (at least on one side and/or at least one edge and at various positions along the longitudinal axis). Preferably, these withdrawal stops (15) will not be disposed so close to the posterior end that a deep recess realized (spared) from the outlet of passage (21) to form complementary surfaces receiving these stops (15) is required. Depending on the position of the withdrawal stops (15), these complementary surfaces may be formed in various places on the implant. For example, in the case of withdrawal stops (15) close to the posterior end, the complementary surfaces may be formed by recesses, created in a wall of passage (21), for example near the lateral sides of the passage. Withdrawal stops (15) disposed further from the posterior end can engage a surface outside the passage (at its outlet), but more posterior stops are preferred because bringing the branches close to each other will allow a disengagement more easily with such stops than with stops further away from the posterior end.

In certain embodiments of anchor (1), the body may be configured with notches (16) oriented to oppose the withdrawal of device (1) once it is implanted in a vertebra. Preferably, these notches will be present only along the portion of the body of anchor (1) that is designed to emerge from the passage when the anchor is fully inserted in the implant. As can be particularly seen from the non-limiting examples shown in FIGS. 1C, 2C and 6B, these notches (16) can vary in number, size and shape. Such notches serve to stabilize the anchor into the bone and prevent the anchor from withdrawing from the bone, especially when bone growth has filled the space between the notches. In some embodiments of the anchor (1), it can be provided, near the rear end of the plate (10), for at least one portion of thickness greater than the thickness of the rest of the plate (10), limiting the clearance of the device in the passage (21) of the implant (2).

In certain embodiments, the ability to readily withdraw the anchor is preferred, and in those embodiments notches (16) or structures allowing growth of bone through the anchors, such as holes or enlarged slots would be generally undesirable. Certain embodiments described herein comprise at least one mechanism allowing removal of anchor (1), and in those embodiments the size of these openings and/or slot may be limited so that they can play their role of holding anchor (1), with bone growth, without impeding withdrawal of anchor (1) by means described herein. Likewise, the shapes and sizes of notches (16) can also be adapted so as to oppose spontaneous withdrawal of anchor (1) while permitting intentional withdrawal by means of the mechanisms described herein. These embodiments are thus not necessarily exclusive, and depend on the sizes of openings and/or of the slot (11) and/or the shapes and sizes of notches (16).

In certain embodiments, anchor (1) (and/or implant) comprise(s) a withdrawal mechanism, such as at least one grip resource (141) for example, facilitating the intentional withdrawal of the anchor from the implant and the vertebra using an anchor extraction tool, if necessary. The tool for extracting anchoring device (1) can have various forms and can for example, comprise at least one shaft curved at its end (like a hook) so as to penetrate into a recess and allow the withdrawal of the anchor by pulling on a shaft. For example, in certain embodiments, retaining stop (14) may be configured with a catch to facilitate withdrawal of anchor (1). In some of these embodiments, such a catch can be obtained by making at least one retaining stop (14, 140), in contact with a complementary stop (25) of implant (2) provides for a free space (141) accessible by a tool. Complementary stop (25) or a nearby area of implant (2) may be configured with a space or gap that allows inserting an anchor extraction tool to pull on retaining stop (14). The withdrawal stops (15) are intended to be disengagable from their mating surface of the implant through a pressure exerted on at least one of the branches to bring them closer to each other, thanks to the presence of the slot (11). It can therefore be provided, for example, as a withdrawal mechanism, a grip resource (141), for example such as housing on each of the branches, to allow a tool configured as a clamp, for example with bent ends to penetrate the housings, enabling to pinch the two branches and pull on the anchor. It is therefore understood that various embodiments of the present invention have the advantage of easy removal of the anchor (and therefore the implant), with a small congestion, while securing a good stability of the anchor.

In certain embodiments, anchoring device (1) comprises a mechanism that will assist stabilizing it in passage (21) in the implant. In certain embodiments, for example, a curved anchor is provided to pass through a straight passage of the implant, without deformation of the anchor (1) in spite of its curvature. These embodiments of implants (2) with straight passage (21) are easier and less expensive to make than the embodiments of implant (2) with curved passage (21). However, for a curved anchor to pass through the straight passage, the height of passage must be at least slightly greater than the thickness of plate (10) in the embodiments of anchors with horizontal orientation (curved in the direction of the plate depth), or greater than the width of plate (10) in the embodiments of anchors with vertical orientation (curved in the direction of the plate width). It is preferable, though, that the anchor has little or no play in passage (21) of implant (2), at least to prevent movements of the anchor (and/or the implant) that will tend to make the anchor come out of the vertebrae. As noted elsewhere in this disclosure, the body of the anchor in some configurations can have various radii of curvature between the two ends (anterior and posterior). In certain embodiments, the curvature of anchoring device (1) at the posterior end can be configured to engage wall of passage (21) sufficiently to improve the hold of anchoring device (1) on implant (2). In certain embodiments, the curved plate (10) of the body comprises a portion near the posterior end which surfaces, preferably substantially planar, limit the play of the device in passage (21) of implant (2) by being slightly thicker than the rest of plate (10). It is understood that the thickened portions close to the posterior end generally correspond at most to the entire length of passage (21), but they are preferably shorter, since the insertion of the anchor through passage (21) could be inhibited if they were too long. An instrument (e.g., 3, 4, 5) (described elsewhere in the disclosure) for inserting anchors (1) into the vertebrae through an implant is a potential object of the invention, and therefore it is preferable for anchors (1) to be configured to pass through this instrument (3, 4). Thus, preferably a thickened portion, possibly planar, on a part of the length of the anchor, will not impede guidance of the anchor into and through the instrument. Thus, in various embodiments, the anchor may be stabilized in the passage by means of at least one thickened stabilization portion, typically disposed on both branches (12, 13) of the anchor and preferably close to the lateral edges of plate (10), with a thickness greater than that of the rest of plate (10). Stabilization portion should not prevent retaining stops (14) from being stopped on their complementary stop (25) in the implant, so when these retaining stops are created on one of the faces of the plate, the stabilization portion preferably will thus be positioned on the face opposite the one comprising retaining stops (14), which will improve their function of stop. During insertion of various configurations of anchor (1), the stabilization portion may impede passage of the anchor if the increase in thickness is too abrupt. Thus, stabilization portion may comprise at least one chamfer or beveled surface, for example where it meets the plate, substantially toward the anterior end, forming a slope so as to provide a progressive increase in thickness up to the optimal thickness that presses anchor (1) in passage (21) and thus limits its play. Note also that the thickness of thickened portion(s), called stabilizing portions, preferably will still be slightly less than the height of passage (21), so as to limit play without completely eliminating it. Nevertheless, in certain variants, this thickness (and/or height) will be equal to or even somewhat greater than the height of passage (21) (and/or depth of the groove, respectively), notably in the case of intersomatic cages whose material (such as PEEK, for example) allows a slight deformation.

A single anchoring device (1) may be used to anchor an implant (2) in a vertebra, but in most applications at least two devices preferably will be used to affix an implant (2) in the 2 adjacent vertebrae between which it is implanted (at least one anchor for each vertebra). As previously mentioned, another potential object of the invention is an anchoring system for the implant comprising two anchoring devices (1), either identical to each other, or different, or complementary to each other, at least one of which being configured according to one of the embodiments described in the present application. Thus, any of the various combinations of any of the embodiments of anchors and features described herein whatsoever are within the scope of the invention, as well as any combination (for example for two different vertebrae) of one anchor according to one of these embodiments with an osseous anchoring device of another type, such as for example the type of one of the embodiments described in the above cited prior applications of the assignee of the present application (as long as the circumstances of the implantation allow such combination).

Implants:

Intervertebral implants (2) comprising at least one passage (21) designed to receive anchoring device (1), such as a slit crossing a portion of the implant, a conduit, or another type of channel arranged to receive anchoring device (1), are also within the scope of the invention. Preferably, such implants are configured to receive at least one anchoring device (1) comprising at least one curved and rigid plate, so as to allow the passage of this anchoring device (1) through the passage (21) without deformation despite the curvature of the device (1). In most configurations, passage (21) crosses implant (2) from the periphery of the implant (2) to an upper or lower surface of implant (2), along a preferably rectilinear and oblique trajectory suited to the curvature of anchoring device (1) and the desired fixation of the implant, as discussed in detail elsewhere in this disclosure. The present application does not describe intervertebral discs in detail, but rather only describes various embodiments of intersomatic cages designed for an arthrodesis. The person skilled in the art will nevertheless understand after appreciating this disclosure that anchoring device (1) configured with various features and various combinations of features according to the invention may be used with a prosthesis comprising at least one posterior part configured to receive anchor (1) as described herein, it being understood that the designation as posterior is relative to the context of the specific circumstances of the implantation (e.g., the approach taken in the implantation and/or the design of the prosthesis). For example, intervertebral prostheses are known whose vertebral contact plates have a sufficient height to offer a peripheral wall in which it is possible to create a passage such as described herein for the insertion of the anchoring device. Likewise, intervertebral prostheses are known comprising two plates and a mobile core between the plates and, in which a peripheral wall of one of the plates limits the movements of the core. Therefore, the invention can be adapted to this type of prosthesis, by making at least one passage (21) in the wall, crossing said wall from a peripheral surface to a vertebral contact surface (lower or upper) of the plate without hindering the movements of the various parts of the prostheses, such as the core, for example. In various embodiments, the passage (21) in the plate need not cross the plate from a peripheral wall of the plate, but instead may cross the plate from one side to the other side (i.e., the upper surface to the lower surface, or vice versa), according an oblique axis (straight or curved) extending from a peripheral area of the prosthesis itself to a vertebral endplate, and the retaining stops (e.g., 14, 140) and/or withdrawal stops (e.g., 15, 150) of anchor (1) can be adapted to make contact with the upper or lower surfaces of the plates (directly or via stop surfaces arranged within the plate). For example, publications FR 2,879,436, WO 2006/120505 and US 2006/0136063, each of which is incorporated herein by reference (filed by the assignee of this application), show a straight anchor with a retaining stop formed by a curved portion (hook-shaped) at the posterior end of the anchor configured to engage a stem near the edges of plates, and this general approach can be adapted to the embodiments disclosed herein after fully appreciating this disclosure. The anchor (1) of the present invention may, for example, be curved and/or comprise at least one slot (11) and/or one or more retaining stops (e.g., 14, 140) and/or one or more withdrawal stops (e.g., 15, 150), for use with such prostheses, and additional features and/or combinations of features described herein may be adapted to such use. In cases where the anchor is designed to cross through a plate of a prosthesis, the term "posterior" "part" or "portion", or the term "peripheral wall" may be used to designate a portion near the periphery of the plate and accessible from a peripheral area of the prosthesis.

Accordingly, certain embodiments of the present invention also concern an intervertebral disc prosthesis created with the means described generally for implant (2). Various types of intervertebral disc prostheses are known and no detail will be given here, except that it may for example comprises at least two plates articulated together (for example via articulation surfaces of the plates and/or an intermediate core) and at least one of which comprises at least one passage (21). Intersomatic cages configured in accordance with the present invention also can have various forms, including configurations notably different from the illustrative examples represented in the figures of the present application. However, the present application also concerns intersomatic (interbody) cages for example as described in the present application, because they are particularly adapted to the problems of invasiveness and stability, and the use of anchors described in the present application can be particularly advantageous in combination with such cages. The description herein gives several non-limiting variants of embodiment in reference to the attached figures, but after fully appreciating this disclosure it will be understood that various implants devised in accordance with the present invention, at least when it concerns a combination of an implant with at least one anchor, may have other forms without departing from the spirit and scope of the invention.

Thus, in the present application, reference is made generally to an intervertebral implant to designate both cages and prostheses, and also osteosynthesis plates. When particular embodiments of intersomatic cages require reference to specific technical features of cages, however, reference may be made to an intersomatic cage rather than to an intervertebral implant.

Various intervertebral implants (2) described herein comprise a body (20), generally with at least one peripheral wall, a posterior portion of which (in accordance with the conventions adopted in this description) comprises at least one passage (21) of suitable dimensions to receive at least one anchoring device (1) configured according to the invention. As explained elsewhere herein, the passage is may be straight to avoid the complex and expensive machining of a curved passage. However, with an implant separable into two parts at the passage joinable together, it is easier to create a curved passage. Moreover, it is possible to manufacture implants, such as intersomatic cages, by molding. It is then possible to more easily produce implants having a curved passage, for example by using a mold with a curved insert. In addition, certain recent techniques allow curved machining, especially in solid materials (for example metals). Therefore it is possible, particularly in the case of intervertebral disc prostheses whose plates are made of metal, to create a curved passage designed to receive the curved anchor without much additional expense and burden over machining a straight passage. If passage (21) in the implant is curved, its height can be generally equal to (or very slightly greater than) the thickness of anchor plate (10). If passage (21) is rectilinear (straight), its height preferably will be at least slightly greater than the thickness of the curved anchor to permit it to pass without deformation of anchor (1) despite its curvature and its rigidity, as discussed elsewhere in the present application. This technical feature of a curved passage (21) within the implant allows many embodiments of objects such as implants and anchoring devices and/or systems in which the implant comprise a curved passage and in which the anchor is curved and comprises at least one slot (11). These particular objects (i.e., any of these embodiments comprising or associated with a curved passage in the implant) may be configured to solve the problems of stability of the fixation of implant and/or of invasiveness.

In some embodiments (not shown), passage (21) may have an entrance with an oblique orientation, in which the width of the passage is neither oriented parallel to the plane of the disc space, nor oriented parallel to the axis of the spine, but intermediate and forming an angle with these reference orientations (which are shown in most of the figures). In these embodiments, it is preferable to have two anchors (1) implanted in the same vertebra, and these anchors (1) preferably have a curvature in the thickness of the plate and one or more radius (or radii) of curvature shorter than generally used for anchors which may be associated with implants having an entrance of the passage oriented horizontally (in the plane of the disc space), so that the anchor has a curvature sufficient to provide a good hold despite its oblique orientation. This oblique orientation may be useful in various circumstances to address the problem of the stability of the anchor and the implant when faced with various constraints of the implantation. Some embodiments may provide, for example, two such anchors associated with an implant comprising at least two passages with such oblique orientation directed toward the same vertebra, but with opposite orientation one in relation to other (fir example, one entrance inclined 45° to the right, and the other inclined 45° to the left). However, horizontal orientations of the passage are generally preferred, in particular for an easier use, notably with an instrumentation such as described in the present application.

The use of an anchor comprising a curved plate can be particularly advantageous with an osteosynthesis plate, in particular in the case of the disc space between vertebrae L5 and S1, because the orientation of the sacrum toward the back of the spine makes it generally difficult to access this area, even by an anterior approach. In general, even with a curved anchor (1), it is preferable to use an approach axis of the instrumentation that is oblique (not perpendicular to the vertebrae) at the level of the sacrum, because of the orientation of the latter toward the back of the spine. The contact surface with the implant at the anterior end of the instrumentation may be inclined with respect to its longitudinal axis (antero-posterior according to the convention used in the present application) for allowing an optimal contact with the osteosynthesis plate. Nevertheless, the approach axis may be substantially perpendicular to the osteosynthesis plate in some circumstances and the instrumentation will then be adapted to this approach axis. Furthermore, it is also possible to use an anchor comprising a straight plate, so as to allow this implantation in various circumstances (e.g., oblique path or path perpendicular to the vertebrae). The instrumentation will thus be adapted according to the shape of the anchor and the approach axis chosen. Implants devised with various features according to the invention may include osteosynthesis plates comprising a passage (21). The posterior part or peripheral wall may then correspond to an osteosynthesis plate itself, forming a wall between the exterior and interior of the disc space. An anchor according to one of the embodiments described herein is then inserted into the passage along an approach axis substantially perpendicular to the osteosynthesis plate (and the axis of the spine at the level of the disc space concerned). The passages (21) in the plate can be arranged to be placed at the disc space or vertebral body level and lead to the endplates or directly in the periphery of the vertebral bodies. The orientation of the entrances of the passages (21) may be oblique as explained above. These fixation plates can be further fixed against the vertebrae with conventional screws, in addition to at least one anchor as described herein.

It is noted that, in a general manner, passages, holes, notches, stops, recesses, lugs, and other elements of the various objects of the invention (anchors, anchor systems, implants, and instruments) may be formed by various methods, such as machining, drilling, casting, welding, etc., and the examples given herein are not to be construed restrictively.

As noted elsewhere herein, the anchor (1) preferably comprises at least one slot (11) on at least one posterior portion of the plate (10). An implant can be fixed by means of several anchors, and it will therefore comprise several passages (21). Preferably, there will be two passages (21) each oriented toward a different one of the vertebrae between which the implant must be implanted. Thus, in certain embodiments, peripheral wall comprises two passages (21) each oriented toward one of the upper and lower surfaces of implant (2) (vertebral contact surfaces of the implant), so as to anchor anchoring device (1) in each of the vertebrae between which implant (2) is designed to be implanted. Passage (21) of an anchor (1) is created in wall of the implant so as to emerge on the vertebrae contact surface of the implant.

Various embodiments of the invention concern an intervertebral implant (2) comprising a body (20) having at least one part, called posterior, and at least one passage (21) configured to accommodate at least one device (1) for anchoring according to the invention, so as to allow the passage of this rigid anchoring device (1) without distortion despite its curvature. The passage (21) in these embodiments passes through the implant (2) from the periphery to a top or bottom surface, typically along a rectilinear and oblique path adapted to the curvature of the anchoring device (1), which is intended to be inserted substantially in the plane of the implant (2), so as to orient the anchoring device (1) during insertion in the direction of the endplate of one of the vertebrae between which the implant (2) is intended to be implanted. To retain the anchor (1) but allow the withdrawal of the anchor, which is facilitated by the presence of the slot (11) thereon, the passage (21) has at least one surface complementary to at least one withdrawal stop (e.g., 15, 150) of the anchoring device (1). Note that this complementary surface of the implant which receives the withdrawal stop (e.g., 15, 150) is generally formed in the passage (21) of the implant, preferably in the vicinity of its entry (or in the posterior peripheral wall) or its outlet (to a vertebral contact surface) or close to this outlet. This surface will be provided depending on the position of the withdrawal stop (e.g., 15, 150) on the anchoring device (1). Several surfaces may be provided for receiving a plurality of withdrawal stops (e.g., 15, 150) of the anchoring device (1). Preferably, there is at least one withdrawal stop (e.g., 15, 150) on each of the branches (e.g., 12, 13) of the anchoring device (1), but several withdrawal stops can be provided on each branch. The stops are generally provided near the posterior end of the plate (10) since these are the rear ends of the branches that can approach each other most easily thanks to the slot. The invention also relates to a combination of various embodiments of the implants described in this application with various embodiments of the anchors described in this application. Such a combination makes it possible to respond in particular to the problem(s) of invasiveness and/or stability in various circumstances attendant to a particular implantation. The invention may also involve an implant system with two or more implants, with or without anchoring devices. In particular, in the case of an implementation of cage by a posterior approach, two intersomatic cages are generally arranged parallel to each other on either side of the sagittal plane. During a transforaminal implantation, it is expected in general only one cage, preferably of larger dimensions, will be implanted obliquely or perpendicularly to the sagittal plane.

In certain embodiments, the peripheral wall of implant (2) comprises two superposed passages (21) or offset passages if the encumbrance constraints allow it, each oriented toward one of the upper and lower surfaces, so as to anchor anchoring device (1) in each of the vertebrae between which implant (2) is designed to be implanted. In other embodiments, implant (2) comprises only one passage (21). Embodiments of prostheses similarly may have only one plate that comprises a passage (21), and the other plate does not.

Figure 3A:
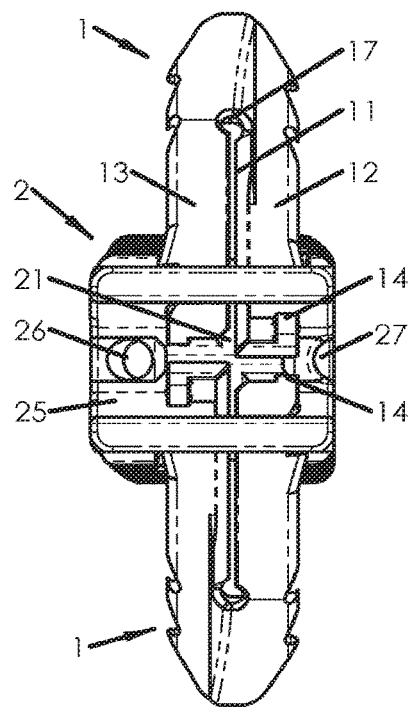
FIGS. 3A and 3B show perspective views of various embodiments of interbody cages equipped with two anchoring devices and FIGS. 3C, 3D, 3E and 3F are respectively a perspective view, a side view, a perspective view and a side view of various embodiments of anchoring devices.
Figure 3B:
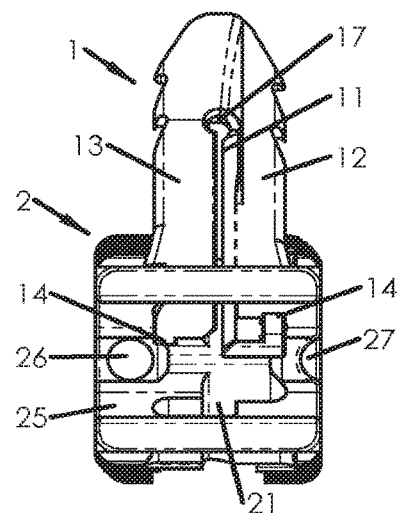
Figure 3C:
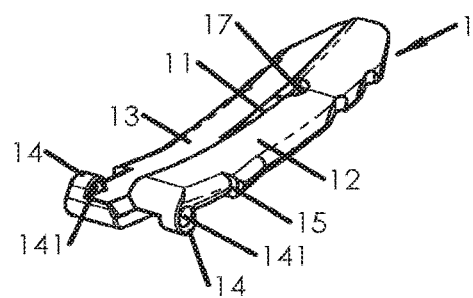
Figure 3D:
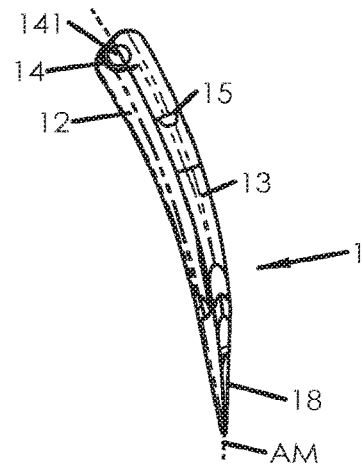
Figure 3E:
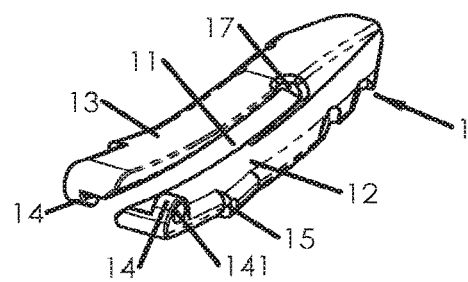
Figure 3F:
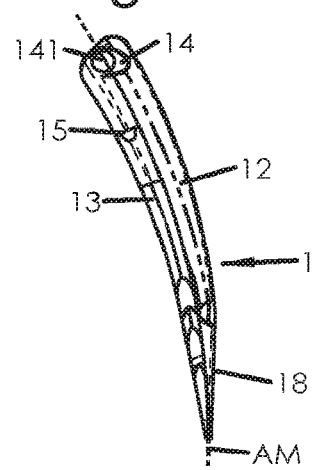

According to various embodiments of the anchor (1) or anchors (1) for use with the implant, the passage for the implant may have various forms, including at its entrance in the posterior part. In the case of anchors whose branches (12, 13) are symmetrical, for example such as those of embodiments corresponding to the examples shown in FIGS. 1A, 2A and 5A, the entrance of the passage preferably is substantially rectangular (possibly with rounded corners) for the plate to pass through it. Such a rectangular passage also may be suitable for some anchors whose branches are not symmetrical, for example like those of the embodiments corresponding to the examples shown in FIGS. 4A and 4C. However, for some anchor embodiments with asymmetrical branches, for example such as those of embodiments corresponding to examples shown in FIGS. 3A and 3B, the passage preferably will be adapted to the fact that the branches are shifted (offset) relative to the other. In some of these embodiments, the anterior end of the anchor, at least to the point where the branches will diverge, may be thinner (less thick) than the anchors of other embodiments, as mentioned above. However this solution is not necessarily completely sufficient. Alternatively or additionally, it is possible to adapt the passage to the anchor and vice versa, as detailed above. FIG. 3B shows a non-limiting and illustrative example of certain embodiments where the mutual adaptation of the anchor to the implant minimizes the overall invasiveness. Instead of enlarging the passage to allow insertion of the anchor, some embodiments of the anchor are provided with an offset at its front end so as to pass more easily and the passage (21) has only a central portion (for example as shown in the lower passage of FIG. 3B which is not equipped with an anchor) suited for the passage of the part of the anchor forming the junction between the offset portions (at the front of the anchor), while the rest of the passage is adjusted to the shapes and dimensions of the anchor (for example as shown on the upper passage of FIG. 3B which equipped with an anchor). Note also that FIGS. 3A and 3B represent examples of two different alternatives. Indeed, the example in FIG. 3A, the implant comprises an upper passage and a lower passage. The upper passage is configured to receive an anchor of the type shown in FIG. 3E for example (whose right branch is lower than the left branch). Similarly, the lower passage of the implant of FIG. 3A is configured to receive an anchor of the type shown in FIG. 3E for example (whose right branch is lower than the left branch). Thus, the implant is arranged so that the branches of its anchors are offset, which implies less design constraints on the implant, in its height. However, the example in FIG. 3B, the upper passage is configured to receive an anchor of the type shown in FIG. 3E for example (whose right branch is lower than the left arm) while the lower passage is configured to receive an anchor of the type shown in FIG. 3C for example (the right branch of which is higher than the branch on the left). This configuration imposes more constraints on the design of the height of the implant, but less in its width, including the possibility of providing a grip resource (26) closer to the passages. Note that the positions and/or orientations and/or dimensions of the stops is (are) still fit to minimize the invasiveness of the examples in FIGS. 3A and 3B. It is generally provided a retaining stop on the longest branch which is the offset towards the middle of the implant (taken in its height) than on the branch shifted to the upper or lower surface of the implant. Various stops on the sides or edges can also be arranged, as explained above. Note also that, in all cases, the portion of the center of the passage (in width) is preferably arranged to allow a sufficient approximation of the two arms to allow the release of withdrawal stops (15). Before anchoring device (1) is implanted to hold implant) in position, there is sometimes a risk that the implant (2) will move in the disc space. In certain embodiments, therefore, at least one of the (upper and/or lower) vertebral contact surfaces of implant (2) may comprises notches (22) avoiding or limiting movement of implant (2) between the vertebrae (e.g., opposing sliding of the implant (2) between the vertebrae). In the case of an intervertebral disc prosthesis, it is also possible to provide stabilization means on the surfaces designed to be in contact with the vertebrae, such as notches or fins or any type of structure preventing it from moving between vertebrae, so as to ensure (or improve) the stability of the prostheses before its fixation by anchoring device (1). According to different embodiments, these notches (22) or other stabilization means can have different orientations. For example, notches (22) can be substantially parallel to one another and all oriented perpendicular to the implant insertion axis, or notches (22) can, on the contrary, have different orientations on different portions of implant (2), so as to prevent movement in various directions, for example such as a chevron pattern, relatively optimal for opposing movements in most directions, and, in particular, movements perpendicular to the anteroposterior axis in these examples of cages with lateral insertion (i.e., movements along an axis in a sagittal or para-sagittal plane of the spine).

It is noted that in various figures of this application, examples of cages represented include notches on their entire or almost entire vertebral contact surfaces, but not on the peripheral wall of the cage. The posterior part of the vertebral contact surfaces of the cage has no notches in these examples. However, it is possible in various embodiments to provide notches on this and other peripheral parts, provided they do not interfere with the various stops, ribs, and/or other elements and features that may be configured on these implants and/or the anchors that may be associated with them.

Figure 9A:
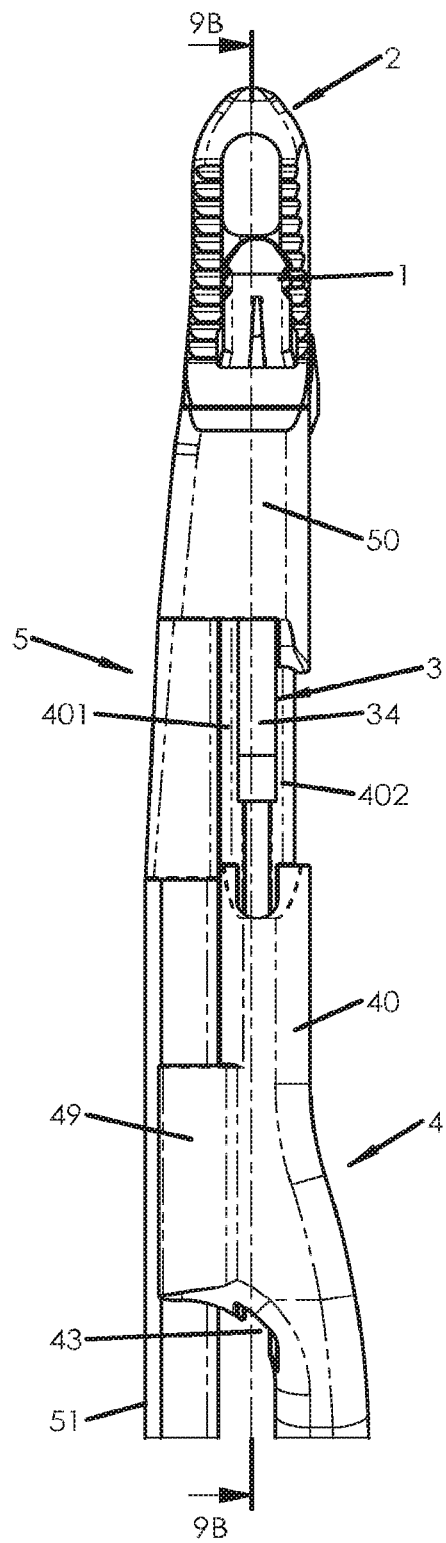
FIGS. 9A and 9B show respectively a top view and a sectional view along plane 9B-9B of FIG. 9A, an end to some embodiments of instrumentation for implantation of interbody cages and anchoring devices, provided with an embodiment of cage, a holder for anchoring device and an anchoring device.
Figure 9B:
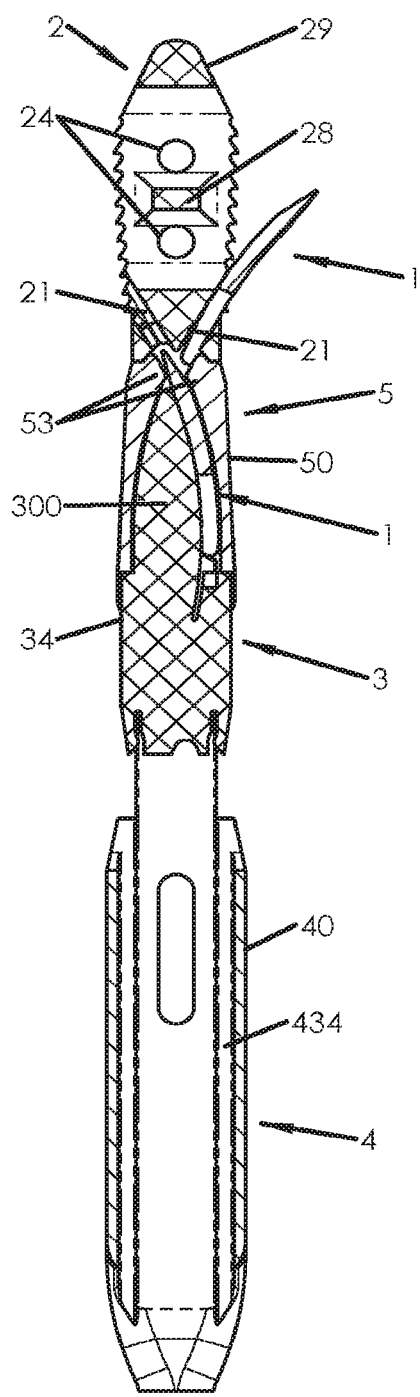

In some embodiments, the intervertebral implant (2) comprises an interbody cage. Typically, the cage comprises a body (2) which may be traversed by at least one hole (23, 24). For such a cage, the peripheral wall can thus define a cavity, opened on the upper and lower surfaces of the implant (those in contact with the vertebrae) designed to receive a bone tissue graft or a substitute. Although an intersomatic cage can comprise a cavity in its center defined by its wall, as shown in the figures of the present application, a cage may also consist of a solid piece without an inner cavity in other configurations within the scope of the invention. This type of cage can be designed to be used at least in pairs, for example, so as to define a cavity between the cages such as is known in the prior art. Moreover, in the case of cages with at least one cavity, and as particularly visible in certain examples shown in FIGS. 1, 2C, and 2, openings (24) can be created in wall of the implant (the lateral walls in the examples shown), so as to also permit the growth of bone tissue transversely through the disc space (i.e., through the cage, parallel to the vertebral endplates). The holes (23, 24) preferably traverse through the body and pass through not only between the upper and lower faces, but also the lateral faces. For example, the illustrative and not limiting examples of FIGS. 1B, 2A, 3A and 3B, the body (20) is traversed not only by vertical holes (23) (between the upper and lower surfaces) but also by horizontal holes (24) (between the side surfaces). The interbody cage (2) may therefore be with or without a central recess, especially if several interbody cages (2) must be located in the same intervertebral space. Such cages are typically used to contain bone (graft) that will grow within the intervertebral space and allow a fusion (arthrodesis) of two vertebrae between which it is implanted. It is also known to use a substitute instead of a bone graft. In all cases, the purpose of the cage (2) is to restore or maintain a space between the vertebrae. Before the growth of the graft and spinal fusion, the cage (2) should remain in place in the disc space and various embodiments of the present invention facilitate its immobilization. Similarly, a prosthesis should typically be fixed to the vertebral endplates in all cases. In certain embodiments, the intersomatic cage may comprise a reinforcement (28) crossing its cavity from side to side to reinforce the walls of cage (2), for example as shown in FIGS. 5B, 5C and 9B. The cavity is preferably equipped with a reinforcement (28) to solidify the implant. This reinforcement can have different shapes and orientations and can be oriented along the axis of insertion of cage (2) between the vertebrae (e.g., the longitudinal axis of the body), but it will preferably be transverse, thus connecting the inner walls of the cavity between the lateral faces (substantially perpendicular to the longitudinal axis of the body of the implant). This transverse orientation allows reinforcing the cage in the direction which might be the most fragile and generally allows it not to interfere with the passage of anchors. In various embodiments, the reinforcement can have a lower height than the rest of the cage. This lower height of the reinforcement with respect to the rest of the cage permits the cage to take on various possible irregularities in the shapes of the vertebral endplates and to avoid completely dividing the graft or substitute contained in the cavity of the cage. The reinforcement may or may not be provided with notches. On the other hand, in certain embodiments, a part of passage (21) emerges into cavity. Generally, the wall can be dimensioned as a function of passage (21), and passage (21) will be dimensioned and oriented as a function of anchoring device (1) in order to orientate and hold this device in the direction of the vertebra into which the anchoring device must be affixed. Moreover, the orientation can be chosen as a function of the desired fixation, as mentioned elsewhere herein (for example, by means of the curves selected for the anchors). Note, however, that the implant dimensions vary as a function of the vertebrae between which they are designed to be implanted and that the dimensions of the anchoring device can also be adapted to those of the implant as a function of those vertebrae.

The form of the implant, even at the level of passage (21), is not limiting, as long as it allows at least one anchor (1) to be introduced. For example, cage (2) represented in the figures of the present application and particularly visible in FIGS. 5B and 5C, has a substantially oblong periphery. The shape of the body, in particular with its anterior end, may have a shape such as, for example, the shape of a bull-nose (bullet or mortar). Generally, the posterior end of the cage, which comprises the passage (21), may have a wall substantially straight and near which the cage will be held by an instrument (3, 4, 5). Even in these examples, however, it is not necessary that the wall be generally planar in this area. In particular, the present invention preferably provides that the entrance of the passage is equipped with surfaces (25) complementary to the retaining stops (14), which may involve non-planar forms. Thus, in some embodiments, the posterior part of the implant (2) which comprises the passage (21) for the anchoring device (1) includes, around the passage (21), at least one housing which surfaces (25) are configured to accommodate at least one retaining stop (14) of the anchoring device (1) without the latter protruding from the body (20) of the implant (2). The anchor (1) is provide for not protruding from the spine (at least), but even not to protrude too much from the implant (because this could injure the tissues, providing hanging or gripping structures tending to move the anchor out of the implant or interfere with insertion of a second anchor). Thus, the anchor (1) is preferably set to not protrude at all from the implant, as shown in FIG. 5B for example. On the other hand, in some embodiments, the posterior part which includes the passage (21) for the anchoring device (1) comprises, around the passage (21), at least one housing whose surfaces (25)

are configured to provide access to grip means (141) of the anchoring device (1), for grasping with the end of a tool for the withdrawal of the anchor by moving the two legs (12, 13) towards each other to disengage one or more withdrawal stops (e.g., 15, 150). Note that in various illustrated intersomatic cages, the substantially oblong shape has a slight curve (especially visible in the top views), but again, this shape is not restrictive with respect to the scope of the invention even if it's preferred for any applications. Various figures of the present application show that various shapes of intersomatic cages may have a peripheral wall including a planar side face (or surface), and a slightly convex superior and inferior side faces (or surfaces), a substantially flat posterior face surface), and a curved front face (or surface), but again, this shape is not restrictive with respect to the scope of the invention. However, the shape such as a bull-nose (bullet or mortar), visible in FIGS. 5B and 5C, for example, is particularly adapted to an implantation of the cage through a posterior or transforaminal pathway. A convex shape of the superior and/or inferior surface(s) is advantageous for matching the shape of the vertebral endplates. It is indeed preferable that the shape of the implant be selected according to the shape of vertebrae between which it will be implanted and to the axis of the anatomical pathway foreseen for its implantation. In certain embodiments, at least one portion, for example situated around the center of the implant, along the longitudinal axis (L) (which may correspond to anteroposterior or oblique axis of the spine), is thicker than the rest of the implant, so as to take on the shape of the vertebrae. Preferably, the surfaces of the implant are adapted to the anatomy of the vertebrae. However, a symmetric shape is generally preferred for the implant to allow turning it upside down (i.e., the superior face disposed at the bottom and the inferior face disposed at the top) and/or use it according to different implantation types.

As mentioned above, some embodiments relate to an intervertebral implant (2) which is actually a cage. Such a cage preferably has a body (20) elongated along a longitudinal axis. It is preferably traversed by at least one hole (23, 24) and comprises at least two side faces, an upper surface, a bottom surface, a rear part and a front part. The shapes and dimensions of the body (20) are preferably configured for implantation by a posterior or transforaminal of the implant (2). The dimensions identified here as being configured for or adapted to implantations through posterior and transforaminal approaches have implications which are relatively clear for the skilled person. However, for clarity and in a purely illustrative and not limiting manner, the following size ranges can be cited: For a cage for a posterior implementation, a shorter body (20) is generally provided than for transforaminal implantation since the latter often implies that the cage is positioned obliquely between the vertebrae and should cover a longer area. Thus, for a cage for a posterior implementation, a range of lengths of about 22 to 26 mm is provided while a range of lengths of about 32 to 34 mm is provided for a cage intended for a transforaminal implantation. Conversely, for problems of invasiveness of the operation, the dimensions in height and width are critical. Cages whose width is only of the order of 10 or 11 mm are particularly advantageous, in particular with anchors as described in the present application. Moreover, according to the intervertebral height desired to be restored or maintained by the cage, one can choose one (or more) cage (s) from a range of height (or thickness), for example from as small as 7.5 mm to 14 mm for the minimum height (e.g., located at the posterior face). Since the cage has often its upper and lower surfaces not parallel to impose an angle to the vertebrae, 14 mm minimum height gives such a height of 17 mm maximum.

Generally, the shape of implant (2) can vary and the shape of the end of instrument (3, 4, 5) that will be in contact with implant (2) can consequently vary in various embodiments. Preferably, the body (20) comprises, in the vicinity of the posterior part, at least one fastener or grip resource (26, 27) for an implantation instrument. The grip resource (26, 27) can be on the posterior part and/or a lateral face, preferably both for offering leverage between these two locations, which facilitates the manipulation of the implant (notably for a pivotal motion as detailed hereafter). Implant (2) of various embodiments can in fact have different shapes consistent with the implant having at least one passage (21) suitable for insertion of anchoring device (1) and preferably a fastener (or grip resource or attachment resources) (26, 27) designed to cooperate with one end of an implantation instrument. Fastener (26, 27) can, depending on the various particular embodiments, be associated with a particular shape of the implant near this fastener (26, 27) to provide good cooperation with the instrument, or even have a particular shape cooperating with a complementary shape of the instrument. For example, the instrument can comprise a contact surface following the shape of the implant. Indeed, the posterior portion of the implant is preferably configured for allowing the use of instrumentation. It can be seen for example on FIGS. 1B, 2A, 3A and 3B that the surfaces (25) around the entrance of passage are flat surfaces inclined towards the entrance of passage (21). This shape allows the retaining stops (14) not to protrude from the implant, but also allows that an instrument (5) with a complementary shape offers a contact which is well distributed on the posterior portion of the implant, which facilitates the manipulation of the implant (notably for a pivotal motion as detailed hereafter).

In certain situations, notably depending on the vertebrae between which implant (2) must be implanted, it is desirable for implant (2) to impose, accommodate, or correct lordosis, kyphosis, or even scoliosis, in addition to maintaining the space between the vertebrae. Certain embodiments therefore provide that the mean planes passing through the upper and lower surfaces of implant (2) (e.g., of the cage or at least one of the plates of the prosthesis) form an angle in at least one direction imposing, accommodating, or correcting lordosis, kyphosis, or scoliosis with respect to the vertebrae between which implant (2) is implanted. This general approach is described, for example, in applications FR 2,869,528 (and WO 2005/104996 and US 2005/0246024) and FR 2,879,436 (and WO 2006/120505 and US 2006/0136063), each of which is incorporated herein by reference, in particular concerning the technical features allowing such inclination of the mean planes of the implants (i.e., thanks to an angle between the mean planes of at least one plate or between the contact vertebral surfaces of a cage, and/or thanks to an asymmetric nucleus and/or to an offset position of the nucleus). Reference to the mean plane reflects herein that the (upper and lower) vertebral contact surfaces are not necessarily planar, since they can be provided with notches or can be convex or even concave; therefore a mean plane is intended to reflect the general orientation that a vertebra resting on the surface will take. For example, several of the intersomatic cages (2) shown in the figures of the present application are lordosis-inducing cages—they are designed to be inserted laterally and their portion intended to be positioned on the anterior side of the vertebrae is thicker than the opposite portion. The upper and lower surfaces (whether convex or flat, and whether or not fitted with notches) are not parallel but are inclined and diverge from each other in the direction of the front end. Thus, the dimensions of the body, between the upper and lower surfaces are larger near the front end than near the rear end of the implant and used to impose a lordosis when implanted through a posterior or transforaminal. Surfaces can also diverge laterally so that the dimensions are more important on one side face than another. Thus, a lordosis adapted to a transforaminal implantation can be obtained and/or a scoliosis may be imposed or corrected.

Although certain embodiments have the mean planes passing through the upper and lower surfaces of implant (2) forming an angle, straight cages can be provided, which typically would thus be symmetrical and have the medial planes passing through the upper and lower surfaces of implant (2) configured substantially parallel to one another. Depending on the desired implantation route for the implant, an angle may be imposed in various directions. For kyphosis and lordosis, this direction is anteroposterior with regard to the spine, with either a thinning of the implant toward the front of the spine to impose kyphosis, or a thinning of the implant toward the rear of the spine to impose lordosis. To impose scoliosis, the mean planes passing through the upper and lower surfaces must form an angle along the other direction of the plane of the disc space (along a frontal or coronal direction, i.e., along an axis oriented mediolaterally with respect to the spine) with a thinning of the implant toward the right or the left, depending on the desired effect. In general, concerning the interbody cages of the present invention which are intended for a posterior or transforaminal implantation, cages imposing a lordosis are preferred because this configuration avoids that the cage moves towards the part of the spine from which it has been implanted.

In certain embodiments, an example of which is shown on FIG. 5B, at least one part of at least one of the superior and inferior surfaces comprises at least one bevel. For example, the body (20) of implant (2) comprises, at the level of an anterior part (using the direction conventions noted elsewhere herein, thus opposite the posterior part comprising the passage (21) for the anchor), at least one beveled portion (29), for example such as at least one chamfer on at least one peripheral portion of at least one of its upper and lower surfaces, so as to facilitate the insertion of implant (2) between the vertebrae. Note that the beveled portion (29) on at least one of the superior and inferior surfaces should not be too large compared to the dimensions of the body (for example having a length less than one third the length of the implant) for leaving a sufficiently large contact surface of the superior and inferior surfaces with the vertebral endplates. For example, one may have only a portion of the junction between, on the one hand, at least one of the superior and inferior surfaces and, on the other hand, the anterior part of the cage, which is beveled (for example the anterior third in the case of an interbody cage).

As is particularly visible in the example of the intersomatic cage of FIGS. 5B and 5C, the anterior end of the cage has substantially the shape of the point of a shell (bull-nose, mortar), to optimize the penetration of the cage between the vertebrae, especially when the space between said vertebrae is insufficient. Chamfer or bevel (29) may be present on both the lower and upper surfaces of implant (2). This chamfer (29) or beveled profile facilitates implanting implant (2) by conferring to it a somewhat lower height on its attack side (the one designed to be inserted first) than on the rest of the cage. In addition, it is also possible to bevel the side faces at the front end of the implant such that it has a bull-nose shape facilitating its penetration between the vertebrae. On the other hand, it is possible to bevel at least a portion of the junctions of at least some of the side faces with the top and bottom surfaces. In particular, it is sometimes desired to insert the implant in an orientation rotated 90° about its longitudinal axis relative to the final position (that in which the upper and lower surfaces are in contact with adjacent vertebrae). Indeed, as explained above, the dimensions of the cage for implantation through a posterior or transforaminal approach may be such that the dimensions of the cage in height are greater than the width of the cage. It may therefore be desirable to first insert the cage with its lateral faces disposed towards the top and bottom of the spine (the upper and lower faces find themselves arranged laterally of the spine), and then rotate the cage to restore the height of the intervertebral space to the desired value (obtained by the fact that the height of the cage has the selected value). One thus inserts the implant in an orientation rotated 90° about its longitudinal axis relative to the final position, then pivots it to place it in its final position in the disc space. In this type of implantation, it may be desirable that at least a portion of at least some of the junctions between the side faces and upper and lower surfaces is beveled to facilitate rotation of the implant between the vertebrae. Bevels or rounded shapes or forms for the cage may thus be provided, even if it is not this type of implantation which is planned, but it is generally preferred that a cage provides a maximum contact area for a given size and therefore has selected junctions that are not too rounded. It is then preferable to provide such bevels when this rotation is intended during the implantation, for an insertion of the implant (2) in a position rotated 90° about its longitudinal axis relative to the final position, where the upper and lower surfaces are in contact with the adjacent vertebrae between which the implant (2) is designed to be implanted. In general, it is sufficient that only some of the junctions are tapered (beveled), such as a single junction of the two junctions between the side faces and the upper surface and a single junction of the two junctions between the side faces and the bottom surface. One preferably chooses the junctions that are opposite each other (the left-bottom junction opposite the right-top junction, for example), such as seen in FIG. 1B for example. In addition, it is sufficient, in general, and particularly when the upper and lower surfaces are inclined with respect to each other (e.g., when the implant is thinner at its rear end to its front end), that only a portion of these junctions is beveled. Indeed, it is sufficient to bevel only the portion at the level of which the cage is the thickest, such as seen in FIG. 1B for example.

As explained in this disclosure, the various configurations or embodiments of implants (2) preferably will be adapted to the configurations or embodiments of anchors (1), in particular for the retaining stops (14) and/or the withdrawal stops (15). Thus, in certain embodiments, the implant comprises, preferably near the passage (21), at least one surface (25) generally facing the outside of implant (2) and forming a stop arranged for cooperating with at least one retaining stop (14) of anchoring device (1), such that once anchoring device (1) is fully anchored in a vertebra through passage (21), the implant (2) is pressed against said vertebra. This arrangement allows that the anchoring device impacted in a vertebra presses the implant (2) against the vertebra, without protruding from the periphery of the spine. As mentioned elsewhere herein, for various configurations of the anchor, the surface(s) (25) may be situated above and/or below the passage, to receive lugs projecting above and/or below the anchor, or on the lateral sides of passage (21) so as to receive two projecting lugs on the sides of the body of anchoring device (1), or any combination of these possibilities. These surfaces (25) are preferably provided offset compared to the rest of the walls of the implant, that is to say in the thickness of the implant (2) (e.g., in a housing), so that the retaining stop (14) of the anchor (1) does not protrude from the implant (2). Indeed, the anchor (1) should not protrude from at least the periphery of the spine, but it is particularly advantageous not to protrude too much from the implant or not to protrude (project) at all. Thus, a reliable fixation is obtained with a high proportion of the anchor planted in the vertebra while a small proportion remains in the implant and a null or almost null proportion protrudes from the rear of the implant. Preferably, there will be 2 stops in each case. Preferably, stop (25) is a recess, the bottom of which forms the stop surface, with depth sufficient to receive retaining stop (14) without it protruding from peripheral wall (28). In certain embodiments, the implant comprises at least one withdrawal stop (212) having at least one stop surface generally facing the anterior end of the anchoring device inserted in passage (21), this withdrawal stop (212) cooperating with at least one withdrawal stop (e.g., 15, 150) of anchor (1), in order to oppose the withdrawal of anchoring device (1) from implant (2).

Instrumentation:

In certain embodiments, an instrumentation (3, 4, 5) may be used to insert implant (2) between the vertebrae and to guide anchoring devices (1) into the implant (2) and drive the anchoring devices (1) into the vertebrae. The invention may relate to the combination of elements (3, 4, 5) of the instrumentation and to each instrument individually, such as an impactor (4), an adapter or holder (3) and a guide (5). Such instrumentation (3, 4, 5), illustrative and non-limiting examples of which are shown in FIGS. 7A, 7B, 7C, 8A, 8B, 8C, 9A and 9B, is intended for the implantation, between the vertebrae, of an intervertebral implant (2) according to the invention and for implantation, in at least one of these vertebrae, of at least one anchoring device (1) according to the invention. The instrumentation preferably includes at least one holder (3) (or adapter or rack or charger) having a body (300) which width is less than the width of said anchor (1) and comprising at least one guiding surface (30) having at least one radius of curvature substantially identical to at least one radius of curvature of a plate (10) of an anchoring device (1), to accommodate and guide the latter during implantation. In addition, the instrumentation preferably includes at least one impactor (4) comprising a head (40) adapted to receive the holder (3) and having two arms (401, 402) of length greater than the length of the body (300) of the holder (3) and spaced apart by a distance greater than or equal to the width of the body (300) of the holder, so as to allow to push, by sliding the impactor (4) along the holder (3), the anchoring device (1) accommodated on the holder (3). Finally, the instrumentation preferably also comprises at least one guide (5) of elongate shape along a longitudinal axis extending between a first end, called gripping end, for holding the implant (2), and a second end, called pushing end, the gripping end having a head (50) equipped at its end with at least one gripping resource (56, 57) intended to cooperate with at least one grip resource (26, 27) of the implant (2), the head (50) being traversed by a longitudinal passageway leading to the implant and of shape and dimensions adapted to accommodate at least partially the body (300) of the holder (3) and the arms (401, 402) of the impactor (4), the passageway comprising at least one surface (53) for guiding said anchoring device (1), complementary to the guiding surface (30) of the holder (3), for guiding said anchoring device (1) between these two guiding surfaces (30, 53) during sliding of the impactor (4) along the holder (3) into the head (50) of the guide (5). With such arrangement of the holder (3) and the guide (5), in combination with the arrangement of the guide (5) holding the implant (2) around the entrance of the passage (21) in the implant (2), a channel guiding the anchor (1) within the instrumentation and into the implant (2) is formed. Such channel has the advantage of allowing a reliable guiding of the anchor (1) avoiding the risk of an incorrect implantation and/or of damaging the anchor or the implant by the insertion of the anchor. Such channel is preferably uninterrupted and thus avoids griping of the anchor by a protruding structure during the implantation.

The impactor preferably comprises at least one longitudinal body (41), such as a rod for example, which is intended to be disposed parallel to the body (51) of the longitudinal guide (5). The body (51) of the guide (5) is preferably also in the form of a rod or a tube. It preferably comprises a handle for holding it and allows to hold the implant at the level of its head (50). The impactor (4) is arranged so that the arms (401, 402) at its head (40) come into the passageway of the head (50) of the guide (5) for pushing at least one anchor (1) through the passage of an implant mounted on the gripping end of the guide (5). The impactor (4) preferably has, at the opposite end to that provided with arms, a pusher (42) on which one can push or knock so as to make the anchor penetrate into the vertebrae through the implant. Preferably, the impactor (4) has guide means (49) for guiding the sliding of the impactor (4) along the longitudinal axis of the guide (5). These guide means (49) can comprise, for example, at least one tab (preferably two legs) not parallel to the longitudinal axis of the impactor and which extends to the guide (5), for example at its longitudinally extended body (51) and surrounds it at least partially or otherwise tracks it, thereby guiding the sliding of the impactor (4) along the longitudinal axis of the guide (5), for example, as particularly seen in FIGS. 8A, 8B and 8C.

In some embodiments, the gripping end for holding the implant that is at the end of the guide (5) comprises at least one gripping resource (56, 57) comprising an end of a rod (56) sliding in the body (51) of the guide (5) when actuated by a handle or knob (52). The body is then generally a tube in which the rod (56) is movable, for moving into and out of a housing (26) of the implant (2) forming a grip resource of the implant. In some embodiments, the rod (56) has a threaded end cooperating with an internal thread of the housing (26) for securing the implant (2) when the rod is actuated by the handle or knob (52).

In some embodiments, the gripping resource (56, 27) of the guide comprises, on the one hand, one end of a rod (56) sliding in the body (51) of the guide (5) when it is actuated by a handle or knob (52) into and out of a housing (26) of the implant (2) forming a grip resource of the implant, and, on the other hand, a lug (57) arranged to be engaged in a second grip resource (27) on a side face of the body (20) of the implant (2) and allowing to act as a lever arm for positioning the implant (2) between the vertebrae. Preferably, the second grip resource (27) comprises a housing (270) for receiving a stud of the tab (57) of the guide, so as to improve the grip of the implant (2) by the instrumentation. Such a second grip resource (27) may for example comprise a groove (27) receiving the tab (57) and equipped with a housing (270) for the stud, as particularly seen in 1B, 2A, 3A, 3B, 5C, 8A, 8B and 8C. One can provide only the second grip resource (27) formed by the groove and the housing for receiving the lug and tab, but it is generally preferred to combine both resources for ease of manipulation of the implant, particularly if it is desired to do an implantation with 90° rotation around the longitudinal axis of the guide. Note that the rod (56) of the guide may have an orientation which is not parallel to the axis of the guide along the entire length of the rod (such as seen in FIGS. 8A and 8C) and that the housing (26) in the implant receiving this rod will have a complementary orientation (such as shown in FIG. 5C). Such an orientation may be obtained by a rod (56) provided with flexibility or with an elbow or joint. In some embodiments, the rod and housing are threaded, but preferably not and it is rather preferred to provide a second grip resource (27) for a good grip and lever arm.

In some embodiments, the gripping end of the guide (5) has shapes complementary to the posterior part of the implant (5), with at least one surface oriented in a plane not perpendicular to the longitudinal axis of the guide and passing through two axes perpendicular to the longitudinal axis of the guide (5), to facilitate rotation of the implant around the longitudinal axis. Indeed, as mentioned previously, the surface (25) around the passage of the implant may form a housing in which the retaining stops will not protrude from the implant. This type of arrangement, by providing that the (or each) surface (25) is oriented in a plane not perpendicular to the longitudinal axis of the implant and passing through two axes perpendicular to said longitudinal axis, provides support to facilitate the rotation of the implant by relieving the forces exerted on the gripping means (56, 57).

In some embodiments, the head (40) of the impactor is traverses by a passageway capable of completely accommodating at least one holder (3) and to allow its removal through the end of the head which is opposite to that equipped with the two arms (401, 402). Moreover, in some embodiments, such as seen in FIGS. 7A, 7B and 7C, the holder (3) has, at its end opposite to that guiding the anchoring device (1), a housing (32) (or notch) arranged to accommodate the front of the guiding end of another holder (3), which may have an inverse orientation. Thus, if one wishes to install two anchors through the passages of an implant, one could mount a first holder (3) holding a first anchor (1) on the arms of the impactor and then impact the anchor through the implant mounted on the guide. Then one moves the impactor backward, with the first holder (3) which will have slid along the arms, and then puts on a second holder (3), in an orientation opposite to that of the first if the implant has two passages with opposite orientations. The second holder, holding a second anchor (1) is then mounted on the arms of the impactor, and pushes the first holder back in the head (40) of the impactor. By impacting the second anchor, the second holder pushes the first holder inside of the impactor's head by itself sliding along the arm. The impactor is then removed and contains the two holders (3) that can be removed, for example by an opening (43) provided at the opposite side of the head of the impactor (the side opposite to that provided arms), such as seen in FIG. 9A. The head of the impactor is therefore preferably a passageway capable of completely accommodating at least one holder (3) to allow for removal at the end of the head which is opposite to that equipped with two arms (401, 402). Note that a lateral window can be provided on the head to help remove the holders.

In some embodiments, such as visible for example in FIGS. 7A, 7B and 7C, the holder comprises, on each of the upper and lower surfaces of its body (300), which are spaced apart by a distance greater than or equal to the height of arms (401, 402) of the impactor (4), a plate (34) of width greater than that of the body (300), to stabilize the holder (3) on the arms (401, 402) of the impactor (4). In some embodiments, the head of the impactor (4) has, in the passageway that crosses it, two grooves (434) to accommodate the edges of the plate (34), such as particularly shown in FIG. 9B. Preferably, the width of the plate is less than that of the anchoring device (1). Preferably, the plates end by flexible tabs (340) provided with a boss to pinch the impactor's arm (4), so as to stabilize the holder on the impactor when preparing instrumentation.

In some embodiments, such as shown in FIGS. 7A, 7B and 7C, the holder (3) has at least one ridge (31) on which the slot (11) of the anchor (1) can be fitted, so that the anchor is then maintained more reliably, for example waiting to get the holder on the impactor and the impactor in the head of the guide (5). This ridge is preferably formed by an edge of a front portion between the guide surface (30) and a plate (34) of the holder. The anchor then rests on the guide surface (30) which maintains it horizontally and is retained by the ridge retains it laterally (the plate (340) of the holder may also be capable of maintaining the anchor horizontally). This ridge (31) is preferably disposed between two surfaces oriented with an angle between them which is adapted to the size and shape of the slot (11) of the anchor (1). Preferably, these surfaces are complementary to the slot (11) or form a structure to block the anchor on it, for example in the manner of a Morse taper.

Methods:

Other potential objects of the present invention relate to various embodiments of methods of preparing for an implantation of, and/or methods for implanting, intervertebral implant (2) into an intervertebral space and for preparing the fixation of, and/or for fixing, the implant to at least one vertebra. These methods may comprise a step of assembling the implant (2) onto a guide (5), a step of mounting the anchor (1) on a holder (3), a step of mounting the holder on the impactor, and a step of placing the impactor (4) relative to the guide, for example up to a penetration, at least partial, of the holder in the head of the guide (5). These various steps can be implemented in different orders, thanks to the arrangement of various objects of the invention, as described in various embodiments discussed in the present application.

In various embodiments, these methods for preparing the implantation may comprise:
  providing an anchoring device (1) in accordance with an embodiment discussed in this present application;
  providing an spinal implant (2) in accordance with an embodiment discussed in this present application;
  providing an implantation instrument (3, 4, 5) in accordance with an embodiment discussed in this present application;
  gripping the spinal implant (2) and/or anchor with the implantation instrument (3, 4, 5);

In various embodiments, these methods for preparing the implantation may further comprise a step of introducing at least one anchoring device (1) within the instrument (3, 4, 5).

In various embodiments, these methods for implanting a spinal implant (i.e., for inserting the implant within a disc space or onto vertebrae) may comprise the steps of the methods for preparing the implantation and may further comprise:
  inserting the spinal implant (2) in an intervertebral space between adjacent vertebrae of a spinal column (or onto adjacent vertebrae of a spinal column in the case of an osteosynthesis plate);

presenting the anchoring device (1) along an approach axis that is substantially perpendicular to the axis of the spine (at the level of the adjacent vertebrae);

using the impactor (4) of the implantation instrument (3, 4, 5), inserting the anchoring device (1) through the guide head (53) of the guide (5) of the implantation instrument (3, 4, 5) and through the passage (21) in the implant (2), with the anchoring device (1) traversing at least a portion of the implant (2); and using the impactor (4) of the implantation instrument (3, 4, 5), fully inserting the anchoring device (1) through the implant (2) and implanting at least part of the anchoring device (1) in one of the adjacent vertebrae.

Note that, in the case of several anchors for an implant, the step of mounting the anchor on the holder and of implanting the anchor can be repeated, for example with a step of positioning the second holder with an inverse orientation compared to the first holder.

Most technical problems solved by various technical features described in the present application may be related to the problem(s) of stability and/or invasiveness mentioned in the preamble of this present disclosure. After appreciating this disclosure, a person of skill in the art may design various embodiments combining the technical features described in this application.

Each of these technical features or of these elements, described in at least one embodiment or configuration and discussed below, may be isolated from other technical features of the object concerned by (or the objects concerned by and/or associated with) said embodiment or configuration (and thus concerning the same or another element) and/or may be combined with any other technical feature described herein, in various embodiments or configurations, unless explicitly stated otherwise, or unless these features are incompatible and/or their combination is not functional, in particular because the structural adaptations that may be required by such isolation or combination of features are directly derivable from the appreciation of the functional considerations provided by the present disclosure.

After fully appreciating this disclosure, a person skilled in the art will understand that numerous embodiments and/or configurations in various other specific forms are possible and within the scope of the invention. Consequently, the present embodiments and/or configurations should be considered as non-limiting illustrative examples that may be modified and still be within the scope of the attached claims, and the invention should not be limited to the details provided above.

The invention claimed is:

1. An implant insertion instrument comprising:
an anchor holder comprising a body including a length and a width and at least one guiding surface configured to guide a curved vertebral anchor into an implant;
an elongate guide comprising a first end including a handle and a second end including a guide head, the guide head including an implant interface and a slot forming a passage through the guide head, the slot to receive the anchor holder; and
an impactor configured to couple alongside the elongate guide, the impactor comprising a pusher end coupled to an impactor head via a longitudinal body, the impactor head including a pair of arms configured to engage the curved vertebral anchor on either side of the anchor holder,
wherein the slot in the guide head traverses the guide head and includes a size and a shape to accommodate at least a portion of the anchor holder and the pair of arms of the impactor head within the passage.

2. The implant insertion instrument of claim 1, wherein the slot in the guide head includes an anchor surface complementary to the at least one guiding surface to assist in guiding the curved vertebral anchor into a passage in a proximal end of the implant.

3. The implant insertion instrument of claim 2, wherein the pair of arms of the impactor head engage the curved vertebral anchor to advance the curved vertebral anchor through the anchor holder and guide head into the passage in the implant upon advancement of the impactor in reference to the elongate guide.

4. The implant insertion instrument of claim 1, wherein the implant interface includes a pair of gripping features, at least one of the pair of gripping features extending past a distal end of the guide head to engage the implant.

5. The implant insertion instrument of claim 4, wherein at least one of the pair of gripping features is a threaded rod to secure the implant to the distal end of the guide head.

6. The implant insertion instrument of claim 5, wherein the threaded rod of the pair of gripping features extends proximally along the elongate guide to a knob on a proximal side of the handle.

7. The implant insertion instrument of claim 6, wherein the pair of gripping features includes a lug disposed in a fixed position within the guide head.

8. The implant insertion instrument of claim 6, wherein the pair of gripping features includes tab extending from a lateral side of the guide head to engage a groove in a lateral side of the implant.

9. The implant insertion instrument of claim 1, wherein the impactor head includes at least one guide tab extending transverse to the pair of arms to guide the impactor along an elongate body of the elongate guide.

* * * * *